(12) United States Patent
Nell et al.

(10) Patent No.: US 9,095,582 B2
(45) Date of Patent: Aug. 4, 2015

(54) SUBSTITUTED ARYLOXAZOLES AND THEIR USE

(71) Applicant: BAYER INTELLECTUAL PROPERTY GmbH, Monheim (DE)

(72) Inventors: Peter Nell, Wuppertal (DE); Walter Hübsch, Wuppertal (DE); Barbara Albrecht-Küpper, Wülfrath (DE); Jorg Keldenich, Wuppertal (DE); Alexandros Vakalopoulos, Hilden (DE); Frank Süssmeier, Wuppertal (DE); Katja Zimmermann, Düsseldorf (DE); Dieter Lang, Velbert (DE); Daniel Meibom, Leverkusen (DE)

(73) Assignee: Bayer Intellectual Property GmbH, Monheim (DE)

(*) Notice: Subject to any disclaimer, the term of this patent is extended or adjusted under 35 U.S.C. 154(b) by 0 days.

(21) Appl. No.: 13/893,344

(22) Filed: May 14, 2013

(65) Prior Publication Data

US 2014/0162981 A1 Jun. 12, 2014

Related U.S. Application Data

(62) Division of application No. 12/671,019, filed as application No. PCT/EP2008/005833 on Jul. 17, 2008, now Pat. No. 8,440,700.

(30) Foreign Application Priority Data

Jul. 27, 2007 (DE) .................. 10 2007 035 367

(51) Int. Cl.
| | | |
|---|---|---|
| *C07D 413/14* | (2006.01) | |
| *A61K 31/443* | (2006.01) | |
| *A61K 31/4439* | (2006.01) | |
| *C07D 413/12* | (2006.01) | |
| *C07D 419/14* | (2006.01) | |
| *A61K 31/695* | (2006.01) | |
| *A61K 45/06* | (2006.01) | |
| *C07F 7/10* | (2006.01) | |

(52) U.S. Cl.
CPC ........... *A61K 31/4439* (2013.01); *A61K 31/695* (2013.01); *A61K 45/06* (2013.01); *C07D 413/12* (2013.01); *C07D 413/14* (2013.01); *C07D 419/14* (2013.01); *C07F 7/10* (2013.01)

(58) Field of Classification Search
CPC .......................... C07D 413/14; A61K 31/443
USPC ........................................ 546/271.4; 514/340
See application file for complete search history.

(56) References Cited

U.S. PATENT DOCUMENTS

| | | | |
|---|---|---|---|
| 4,052,510 A | 10/1977 | Simpson et al. | |
| 5,670,525 A | 9/1997 | Urbahns et al. | |
| 5,889,002 A | 3/1999 | Nielsen et al. | |
| 6,191,280 B1 | 2/2001 | Hamprecht et al. | |
| 6,586,441 B2 | 7/2003 | Borroni et al. | |
| 6,632,823 B1 | 10/2003 | Vernier et al. | |
| 6,693,102 B2 | 2/2004 | Stasch et al. | |
| 6,706,717 B2 | 3/2004 | Barrish et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,045,631 B2 | 5/2006 | Rosentreter et al. | |
| 7,078,417 B2 | 7/2006 | Rosentreter et al. | |
| 7,109,218 B2 * | 9/2006 | Rosentreter et al. | 514/332 |
| 7,129,255 B2 | 10/2006 | Rosentreter et al. | |
| 7,135,486 B1 | 11/2006 | Rosentreter et al. | |
| 7,173,036 B2 | 2/2007 | Sircar et al. | |
| 7,173,037 B2 | 2/2007 | Alonso-Alija et al. | |
| 7,186,716 B2 | 3/2007 | Wei et al. | |
| 7,674,825 B2 | 3/2010 | Alonso-Alija et al. | |
| 7,692,017 B2 | 4/2010 | Dinsmore et al. | |
| 7,705,043 B2 | 4/2010 | Alonso-Alija et al. | |
| 7,709,504 B2 | 5/2010 | Krahn et al. | |
| 7,781,470 B2 | 8/2010 | Alonso-Alija et al. | |
| 7,825,255 B2 | 11/2010 | Rosentreter et al. | |
| 7,855,219 B2 | 12/2010 | Rosentreter et al. | |
| 7,932,259 B2 | 4/2011 | Nakazato et al. | |
| 7,951,811 B2 | 5/2011 | Nakazato et al. | |
| 2003/0232860 A1 | 12/2003 | Harada et al. | |
| 2004/0162427 A1 | 8/2004 | Rosentreter et al. | |

(Continued)

FOREIGN PATENT DOCUMENTS

| | | |
|---|---|---|
| EP | 0 608 565 A1 | 12/1993 |
| JP | 09-132529 | 5/1997 |

(Continued)

OTHER PUBLICATIONS

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al.: A1-, A2A- and A3-subtype adenosine receptors modulate intraocular pressure in the mouse, British Journal of Pharmacology, 2001, 134:241-245.

Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

(Continued)

*Primary Examiner* — Patricia L Morris
(74) *Attorney, Agent, or Firm* — Karen B. King

(57) ABSTRACT

The present application relates to novel substituted aryloxazole derivatives, to processes for their preparation, to their use for the treatment and/or prophylaxis of diseases and to their use for preparing medicaments for the treatment and/or prophylaxis of diseases, preferably for the treatment and/or prevention of cardiovascular and metabolic disorders.

5 Claims, No Drawings

(56) References Cited

U.S. PATENT DOCUMENTS

| | | | |
|---|---|---|---|
| 2004/0176446 | A1 | 9/2004 | Alonso-Alija et al. |
| 2005/0182105 | A1 | 8/2005 | Nirschi et al. |
| 2005/0227972 | A1 | 10/2005 | Rosentreter et al. |
| 2005/0250774 | A1 | 11/2005 | Ono et al. |
| 2006/0264432 | A1 | 11/2006 | Rosentreter et al. |
| 2007/0066630 | A1 | 3/2007 | Palani et al. |
| 2007/0213372 | A1 | 9/2007 | Rosentreter et al. |
| 2007/0293670 | A1 | 12/2007 | Nakazato et al. |
| 2008/0167321 | A1 | 7/2008 | Kamboj et al. |
| 2008/0269300 | A1 | 10/2008 | Erguden et al. |
| 2009/0221649 | A1 | 9/2009 | Krahn et al. |
| 2010/0009973 | A1 | 1/2010 | Rhodes et al. |
| 2010/0022544 | A1 | 1/2010 | Nell et al. |
| 2010/0048641 | A1 | 2/2010 | Nell et al. |
| 2010/0069363 | A1 | 3/2010 | Nell et al. |
| 2010/0093728 | A1 | 4/2010 | Nell et al. |
| 2011/0207698 | A1 | 8/2011 | Meibom et al. |
| 2011/0294718 | A1 | 12/2011 | Lerchen et al. |
| 2011/0294719 | A1 | 12/2011 | Lerchen et al. |

FOREIGN PATENT DOCUMENTS

| | | |
|---|---|---|
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | 02/48115 A2 | 6/2002 |
| WO | 02/50071 A1 | 6/2002 |
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V., 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Triniethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyano-pyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using α,β—Unsaturated Nitriles: Facile Synthesis of Pyridine Derivatives," Synthesis Communications, Jul. 1981, pp. 531-533.

Klotz, et al."Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Olah, et al.:"Cloning, Expression, and Characterization of the Unique Bovine A1 Adenosine Receptor," Journal of Biological Chemistry, May 25, 1992, 267(15):10764-10770.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Poulsen, et al.:"Adenosine Receptors: New Opportunities for Future Drugs," Bioorganic & Medicinal Chemistry, Jan. 8, 1998, 6(6): 619-641.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

(56) References Cited

OTHER PUBLICATIONS

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Ruhe, et al.:"Use of Antioxidant Nutrients in the Prevention and Treatment of Type 2 Diabetes," Journal of the American College of Nutrition, 2001, 20(5): 363S-369S.

Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan:"The Most Common Chemical Replacements in Drug-Like Compounds," J Chem. Inf. Comput. Sci., 2002, 42:103-108.

Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski, et al.:"Biological Role of Chromium," Diabetologia Polska, 2003, 10(3):365-370, English language abstract retrieved from EMBASE Accession No. 2004016455.

Vasudevan A. et al., "Aminopiperidine indazoles as orally efficacious melanin concentrating hormone receptoer-1 antagonists," Bioorg. Med. Chem. Lett. 2005, 15 (23), 5293-5297.

Vippagunta, et al.:"Dystalline Solids," Advanced Drug Delivery Reviews, May 16, 2001, 48(1):3-26.

West:"Solid State Chemistry and its Applications," Wiley, New York, 1988, pp. 358 & 365.

Ye, et al.:Organic Synthesis with α-Diazocarbonyl Compounds, Chem. Rev. 1994, 94:1091-1160.

Yu, et al:"Physical Characterization of Polymorphic Drugs: An Integrated Characterization Strategy," Pharmaceutical Science & Technology Today, Jun. 1998, 1(3):118-127.

Zhu, G. et al., "Design and synthesis of pyridine-pyrazolopyridine-based inhibitors of protein kinase B/Akt," Bioorg. Med. Chem. 2007, 15 (6), 2441-2452.

U.S. Appl. No. 12/697,000, filed Jan. 29, 2010.

U.S. Appl. No. 13/210,889, filed Aug. 16, 2011.

* cited by examiner

SUBSTITUTED ARYLOXAZOLES AND THEIR USE

The present application relates to novel substituted aryloxazole derivatives, to processes for their preparation, to their use for the treatment and/or prophylaxis of diseases and to their use for preparing medicaments for the treatment and/or prophylaxis of diseases, preferably for the treatment and/or prevention of cardiovascular and metabolic disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via G, proteins), a decrease of the intracellular cAMP concentration is observed (preferably after direct prestimulation of adenylate cyclase by forskolin). Correspondingly, A2a and A2b agonists (coupling preferably via G proteins) leads to an increase and A2a and A2b antagonists to a decrease of the cAMP concentration in the cells. In the case of A2 receptors, a direct prestimulation of adenylate cyclase by forskolin is of no benefit.

In humans, the activation of A1 receptors by specific A1 agonists results in a rate-dependent lowering of the heart rate, without any effect on blood pressure. Thus, selective A1 agonists may be suitable inter alia for the treatment of angina pectoris and atrial fibrillation.

The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In adipocytes, the activation of A1 and A2b receptors leads to an inhibition of lipolysis. Thus, the selective or combined action of A1 and A1/A2b agonists on lipid metabolism results in a lowering of free fatty acids and triglycerides. In turn, in patients suffering from metabolic syndrome and in diabetics, reduced lipids lead to lower insulin resistance and improved symptoms.

The abovementioned receptor selectivity can be determined by the effect of the substances on cell lines which, after stable transfection with the corresponding cDNA, express the receptor subtypes in question [see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference].

The effect of the substances on such cell lines can be monitored by biochemical measurement of the intracellular messenger cAMP [see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference].

The "adenosin-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of the adenosine ligands of this type of structure have the disadvantage that their action is not really receptor-specific, that their activity is less than that of natural adenosine or that they have only very weak activity after oral administration. Thus, they are mainly used only for experimental purposes.

WO 01/25210, WO 02/070484 and WO 02/070485 disclose substituted 2-thio- or 2-oxy-3,5-dicyano-4-phenyl-6-aminopyridines as adenosine receptor ligands for the treatment of disorders. WO 03/053441 describes specifically substituted 2-thio-3,5-dicyano-4-phenyl-6-aminopyridines as selective ligands of the adenosine A1 receptor, and WO 2006/027142 claims substituted phenylaminothiazole derivatives as dual adenosine A1/A2b agonists for the treatment of hypertension and other cardiovascular disorders. However, it was found that some of these compounds have disadvantages with respect to their physicochemical properties, such as, for example, their solubility and/or formulability, or with respect to their in vivo properties, such as, for example, their pharmacokinetic behavior, their dose-activity relationship and/or their path of metabolism.

Furthermore, WO 01/62233 discloses various pyridine and pyrimidine derivatives and their use as adenosine receptor modulators. Substituted 3,5-dicyanopyridines as calcium-dependent potassium channel openers for the treatment of urological disorders are claimed in EP 1 302 463-A1. WO 2004/054505 claims the use of aminocyanopyridine derivatives as MK 2 inhibitors for the treatment of TNFα-mediated disorders. The use of 4-aryl- or 4-heteroaryl-substituted aminocyanopyridines as androgen receptor modulators is described in US 2005/0182105.

It was an object of the present invention to provide novel compounds which act as selective agonists of the adenosine A1 receptor or as selective dual agonists of the adenosine A1 and A2b receptor and which, as such, are suitable for the treatment and/or prevention in particular of cardiovascular disorders such as hypertension, angina pectoris, myocardial infarction, heart failure and atrial fibrillation, of metabolic syndrome, of diabetes and dyslipidemias and also for the protection of organs during transplantations and surgical interventions, and which additionally have an improved therapeutic profile compared to the compounds known from the prior art.

The present invention provides compounds of the formula (I)

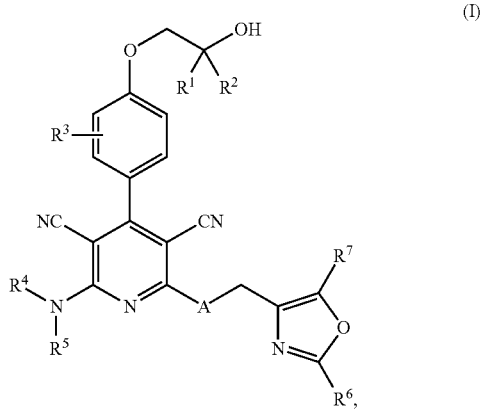

in which
A represents O or S,
$R^1$ represents hydrogen or $(C_1-C_4)$-alkyl,
$R^2$ represents hydrogen or $(C_1-C_4)$-alkyl which may be substituted by hydroxyl, $(C_1-C_4)$-alkoxy or up to three times by fluorine
or
$R^1$ and $R^2$ are attached to one another and together with the carbon atom to which they are attached form a cyclopropane or cyclobutane ring,
$R^3$ represents hydrogen, halogen or $(C_1-C_4)$-alkyl,
$R^4$ and $R^5$ are identical or different and independently of one another represent hydrogen or $(C_1-C_6)$-alkyl which may be mono- or disubstituted by identical or different substituents from the group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle,
where the heterocycle mentioned contains one or two ring heteroatoms from the group consisting of N, O and S and for its part may be mono- or disubstituted by identical or different substituents from the group consisting of $(C_1-C_4)$-alkyl, hydroxyl, oxo and $(C_1-C_4)$-alkoxy,
or
$R^4$ and $R^5$ together with the nitrogen atom to which they are attached form a 4- to 7-membered heterocycle which contains a further ring heteroatom from the group consisting of N, O and S and which may be mono- or disubstituted by identical or different substituents from the group consisting of $(C_1-C_4)$-alkyl, hydroxyl, oxo and $(C_1-C_4)$-alkoxy,
and either (i)
$R^6$ represents $(C_6-C_{10})$-aryl or 5- to 10-membered heteroaryl having up to three ring heteroatoms from the group consisting of N, O and S, which radicals may in each case be mono- to trisubstituted by identical or different substituents from the group consisting of halogen, nitro, cyano, $(C_1-C_4)$-alkyl, trifluoromethyl, hydroxyl, $(C_1-C_4)$-alkoxy, difluoromethoxy, trifluoromethoxy, mono-$(C_1-C_4)$-alkylaminocarbonyl, $(C_1-C_4)$-alkoxycarbonyl and carboxyl,
and
$R^7$ represents hydrogen, fluorine, chlorine, $(C_1-C_4)$-alkyl, trifluoromethyl, $(C_1-C_4)$-alkoxycarbonyl, carboxyl or phenyl, where
$(C_1-C_4)$-alkyl may be substituted by hydroxyl or $(C_1-C_4)$-alkoxy
and
phenyl may be substituted by halogen, cyano, $(C_1-C_4)$-alkyl or trifluoromethyl,
or (ii)
$R^6$ represents hydrogen or $(C_1-C_4)$-alkyl
and
$R^7$ represents phenyl or 5- or 6-membered heteroaryl having up to two ring heteroatoms from the group consisting of N, O and S, which radicals may in each case be mono- or disubstituted by identical or different substituents from the group consisting of halogen, cyano, $(C_1-C_4)$-alkyl and trifluoromethyl,
or the salts, solvates and solvates of the salts thereof.

Compounds according to the invention are the compounds of the formula (I) and the salts, solvates and solvates of the salts thereof, the compounds which are encompassed by the formulae (I) and are mentioned in the formulae below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

For the purposes of the invention, $(C_1-C_6)$-alkyl and $(C_1-C_4)$-alkyl are straight-chain or branched alkyl radicals having 1 to 6 and 1 to 4 carbon atoms, respectively. Preference is given to a straight-chain or branched alkyl radical having 1 to 4 carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

For the purposes of the invention, $(C_1-C_4)$-alkoxy represents a straight-chain or branched alkoxy radical having 1 to 4 carbon atoms. The following radicals may be mentioned by way of example and by way of preference: methoxy, ethoxy, n-propoxy, isopropoxy, n-butoxy and tert-butoxy.

For the purposes of the invention, $(C_1-C_4)$-alkoxycarbonyl represents a straight-chain or branched alkoxy radical having 1 to 4 carbon atoms, which is attached via a carbonyl group. The following radicals may be mentioned by way of example and by way of preference: methoxycarbonyl, ethoxycarbonyl, n-propoxycarbonyl, isopropoxycarbonyl and tert-butoxycarbonyl.

For the purposes of the invention, mono-$(C_1-C_4)$-alkylamino represents an amino group having a straight-chain or branched alkyl substituent having 1 to 4 carbon atoms. The following radicals may be mentioned by way of example and by way of preference: methylamino, ethylamino, n-propylamino, isopropylamino, n-butylamino and tert-butylamino.

For the purposes of the invention, mono-$(C_1-C_4)$-alkylaminocarbonyl represents an amino group which is attached via a carbonyl group and has a straight-chain or branched alkyl substituent having 1 to 4 carbon atoms. The following radicals may be mentioned by way of example and by way of preference: methylaminocarbonyl, ethylaminocarbonyl, n-propylaminocarbonyl, isopropyl-aminocarbonyl, n-butylaminocarbonyl and tert-butylaminocarbonyl.

For the purposes of the invention, di-$(C_1-C_4)$-alkylamino represents an amino group having two identical or different straight-chain or branched alkyl substituents having in each case 1 to 4 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino and N-tert-butyl-N-methylamino.

For the purposes of the invention, $(C_6-C_{10})$-aryl represents an aromatic carbocycle having 6 or 10 ring carbon atoms. Preferred aryl radicals are phenyl and naphthyl.

For the purposes of the invention, a 4- to 7-membered heterocycle represents a saturated heterocycle having a total of 4 to 7 ring atoms which contains one or two ring heteroatoms from the group consisting of N, O and S and which is attached via a ring carbon atom or, if appropriate, via a ring nitrogen atom. Preference is given to a 4- to 6-membered heterocycle having one or two ring heteroatoms from the group consisting of N and O. The following radicals may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Preference is given to azetidinyl, pyrrolidinyl, tetrahydrofuranyl, piperidinyl, piperazinyl, tetrahydropyranyl and morpholinyl.

For the purposes of the invention, an azetidino, pyrrolidino, piperidino or morpholino radical is an azetidine, pyrrolidine, piperidine and morpholine ring, respectively, which is attached via the respective ring nitrogen atom.

For the purposes of the invention, 5- to 10-membered heteroaryl represents a mono- or, if appropriate, bicyclic aromatic heterocycle (heteroaromatic) having a total of 5 to 10 ring atoms which contains up to three identical or different ring heteroatoms from the group consisting of N, O and S and which is attached via a ring carbon atom, or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to two ring heteroatoms from the group consisting of N, O and S, such as, for example, furyl, thienyl, thiazolyl, oxazolyl, isothiazolyl, isoxazolyl, pyrazolyl, imidazolyl, pyridyl, pyrimidinyl, pyridazinyl, pyrazinyl.

For the purposes of the invention, halogen includes fluorine, chlorine, bromine and iodine. Preference is given to chlorine or fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three, identical or different substituents. Very particularly preferred is substitution by one or two identical or different substituents.

For the purposes of the present invention, preference is given to compounds of the formula (I) in which
A represents O or S,
$R^1$ represents hydrogen or methyl,
$R^2$ represents hydrogen, methyl, hydroxymethyl, methoxymethyl or trifluoromethyl,
$R^3$ represents hydrogen, fluorine or methyl,
$R^4$ represents hydrogen or $(C_1-C_4)$-alkyl which may be mono- or disubstituted by identical or different substituents from the group consisting of hydroxyl, $(C_1-C_4)$-alkoxy, amino, mono-$(C_1-C_4)$-alkylamino, di-$(C_1-C_4)$-alkylamino, carboxyl and a 4- to 6-membered heterocycle, where the heterocycle mentioned contains one or two ring heteroatoms from the group consisting of N and O and for its part may be mono- or disubstituted by identical or different substituents from the group consisting of methyl, hydroxy and methoxy, $R^5$ represents hydrogen or methyl or $R^4$ and $R^5$ together with the nitrogen atom to which they are attached form a 4- to 6-membered heterocycle which may contain a further ring heteroatom from the group consisting of N and O and which may be mono- or disubstituted by identical or different substituents from the group consisting of methyl, hydroxyl and/or methoxy, and either (i)

$R^6$ represents phenyl, pyridyl or thienyl which may in each case be mono- to trisubstituted by identical or different substituents from the group consisting of fluorine, chlorine, cyano, $(C_1-C_4)$-alkyl, trifluoromethyl, $(C_1-C_4)$-alkoxy, trifluoromethoxy, mono-$(C_1-C_4)$-alkylaminocarbonyl, $(C_1-C_4)$-alkoxycarbonyl and carboxyl, and $R^7$ represents hydrogen, $(C_1-C_4)$-alkyl, trifluoromethyl, $(C_1-C_4)$-alkoxycarbonyl, carboxyl or phenyl which may be substituted by fluorine or chlorine, or (ii)

$R^6$ represents hydrogen and $R^7$ represents phenyl which may be mono- or disubstituted by identical or different substituents from the group consisting of fluorine, chlorine, cyano, methyl and trifluoromethyl, and their salts, solvates and solvates of the salts.

In the context of the present invention, particular preference is given to compounds of the formula (I) in which A represents O or S, $R^1$ represents hydrogen or methyl, $R^2$ represents hydrogen, methyl, hydroxymethyl or trifluoromethyl, $R^3$ represents hydrogen or fluorine, $R^4$ represents hydrogen or $(C_1-C_4)$-alkyl which may be mono- or disubstituted by identical or different substituents from the group consisting of hydroxyl, amino, methylamino, ethylamino, dimethylamino and diethylamino, $R^5$ represents hydrogen or methyl or $R^4$ and $R^5$ together with the nitrogen atom to which they are attached form an azetidino, pyrrolidino or piperidino ring, each of which may be substituted by hydroxyl, or a morpholino ring, $R^6$ represents phenyl or thienyl which may in each case be mono- or disubstituted by identical or different substituents from the group consisting of fluorine, chlorine, methyl, trifluoromethyl, methoxy and carboxyl, and $R^7$ represents hydrogen, methyl, trifluoromethyl, methoxycarbonyl or carboxyl, and their salts, solvates and solvates of the salts.

The specific radical definitions given in the respective combinations or preferred combinations of radicals are, independently of the particular given combinations of radicals, also replaced by any radical definitions of other combinations.

Particular preference is given to combinations of two or more of the preferred ranges mentioned above.

In the context of the present invention, the compounds mentioned below are especially preferred 2-amino-6-({[2-(3-chloro-4-fluorophenyl)-1,3-oxazol-4-yl]methyl}sulfanyl)-4-[4-(2-hydroxy-ethoxy)phenyl]pyridine-3,5-dicarbonitrile;

2-amino-6-({[2-(3,4-difluorophenyl)-1,3-oxazol-4-yl]methyl}sulfanyl)-4-[4-(2-hydroxyethoxy)-phenyl]pyridine-3,5-dicarbonitrile;

2-amino-6-({[2-(4-fluoro-3-methylphenyl)-1,3-oxazol-4-yl]methyl}sulfanyl)-4-[4-(2-hydroxy-ethoxy)phenyl]pyridine-3,5-dicarbonitrile;

2-amino-6-({[2-(4-chlorophenyl)-1,3-oxazol-4-yl]methyl}sulfanyl)-4-(4-{[(2S)-2,3-dihydroxypropyl]oxy}phenyl)pyridine-3,5-dicarbonitrile;

2-amino-6-({[2-(4-chlorophenyl)-1,3-oxazol-4-yl]methyl}sulfanyl)-4-(4-{[(2R)-2,3-dihydroxypropyl]oxy}phenyl)pyridine-3,5-dicarbonitrile;

2-amino-4-(4-{[(2S)-2,3-dihydroxypropyl]oxy}phenyl)-6-({[2-(4-fluorophenyl)-5-methyl-1,3-oxazol-4-yl]methyl}sulfanyl)pyridine-3,5-dicarbonitrile;

2-amino-6-({[2-(4-chlorophenyl)-5-methyl-1,3-oxazol-4-yl]methyl}sulfanyl)-4-(4-{[(2S)-2,3-dihydroxypropyl]oxy}phenyl)pyridine-3,5-dicarbonitrile;

2-amino-4-(4-{[(2S)-2,3-dihydroxypropyl]oxy}phenyl)-6-({[2-(2-fluorophenyl)-5-methyl-1,3-oxazol-4-yl]methyl}sulfanyl)pyridine-3,5-dicarbonitrile;

2-amino-4-(4-{[(2R)-2,3-dihydroxypropyl]oxy}-phenyl)-6-({[2-(4-methoxyphenyl)-5-methyl-1,3-oxazol-4-yl]methyl}sulfanyl)pyridine-3,5-dicarbonitrile;

2-amino-6-({[2-(4-chloro-3-methylphenyl)-1,3-oxazol-4-yl]methyl}sulfanyl)-4-(4-{[(2R)-2,3-dihydroxypropyl]oxy}phenyl)pyridine-3,5-dicarbonitrile;

4-{4-[({6-amino-3,5-dicyano-4-[4-(2-hydroxy-2-methylpropoxy)phenyl]pyridin-2-yl}thio)methyl]-5-methyl-1,3-oxazol-2-yl}benzoic acid;

2-amino-4-(4-{[(2R)-2,3-dihydroxypropyl]oxy}phenyl)-6-({[2-(4-fluorophenyl)-1,3-oxazol-4-yl]-methyl}sulfanyl)pyridine-3,5-dicarbonitrile;

2-amino-6-{[2-(4-chlorophenyl)-1,3-oxazol-4-yl]methoxy}-4-[4-(2-hydroxyethoxy)phenyl]-pyridine-3,5-dicarbonitrile;

2-amino-6-{[2-(3,4-difluorophenyl)-1,3-oxazol-4-yl]methoxy}-4-[4-(2-hydroxyethoxy)phenyl]-pyridine-3,5-dicarbonitrile;

2-({[2-(4-chlorophenyl)-1,3-oxazol-4-yl]methyl}sulfanyl)-4-[4-(2-hydroxyethoxy)phenyl]-6-(pyrrolidin-1-yl)pyridine-3,5-dicarbonitrile;

2-({[2-(4-chlorophenyl)-1,3-oxazol-4-yl]methyl}sulfanyl)-4-[4-(2-hydroxyethoxy)phenyl]-6-[(2-hydroxyethyl)amino]pyridine-3,5-dicarbonitrile;

2-({[2-(4-chlorophenyl)-1,3-oxazol-4-yl]methyl}sulfanyl)-6-{[(2R)-2,3-dihydroxypropyl]amino}-4-[4-(2-hydroxyethoxy)phenyl]pyridine-3,5-dicarbonitrile;

2-({[2-(4-chlorophenyl)-1,3-oxazol-4-yl]methyl}sulfanyl)-4-[4-(2-hydroxyethoxy)phenyl]-6-[(3R)-3-hydroxypyrrolidin-1-yl]pyridine-3,5-dicarbonitrile;

2-{[2-(4-chlorophenyl)-1,3-oxazol-4-yl]methoxy}-4-[4-(2-hydroxyethoxy)phenyl]-6-[(2-hydroxy-ethyl)amino]pyridine-3,5-dicarbonitrile and 2-{[2-(4-chlorophenyl)-1,3-oxazol-4-yl]methoxy}-6-(3-hydroxyazetidin-1-yl)-4-[4-(2-hydroxy-ethoxy)phenyl]pyridine-3,5-dicarbonitrile and their salts, solvates and solvates of the salts.

In the context of the present invention, the compounds mentioned below are very particularly preferred 2-amino-6-({[2-(3,4-difluorophenyl)-1,3-oxazol-4-yl]methyl}sulfanyl)-4-[4-(2-hydroxyethoxy)-phenyl]pyridine-3,5-dicarbonitrile;

2-amino-6-({[2-(4-chlorophenyl)-1,3-oxazol-4-yl]methyl}sulfanyl)-4-(4-{[(2S)-2,3-dihydroxypropyl]oxy}phenyl)pyridine-3,5-dicarbonitrile;

2-amino-6-({[2-(4-chlorophenyl)-1,3-oxazol-4-yl]methyl}sulfanyl)-4-(4-{[(2R)-2,3-dihydroxypropyl]oxy}phenyl)pyridine-3,5-dicarbonitrile;

2-amino-6-({[2-(4-chlorophenyl)-5-methyl-1,3-oxazol-4-yl]methyl}sulfanyl)-4-(4-{[(2S)-2,3-dihydroxypropyl]oxy}phenyl)pyridine-3,5-dicarbonitrile;

2-amino-6-{[2-(4-chlorophenyl)-1,3-oxazol-4-yl]methoxy}-4-[4-(2-hydroxyethoxy)phenyl]-pyridine-3,5-dicarbonitrile;

2-({[2-(4-chlorophenyl)-1,3-oxazol-4-yl]methyl}sulfanyl)-4-[4-(2-hydroxyethoxy)phenyl]-6-[(2-hydroxyethyl)amino]pyridine-3,5-dicarbonitrile;

2-({[2-(4-chlorophenyl)-1,3-oxazol-4-yl]methyl}sulfanyl)-4-[4-(2-hydroxyethoxy)phenyl]-6-[(3R)-3-hydroxypyrrolidin-1-yl]pyridine-3,5-dicarbonitrile and 2-{[2-(4-chlorophenyl)-1,3-oxazol-4-yl]methoxy}-6-(3-hydroxyazetidin-1-yl)-4-[4-(2-hydroxy-ethoxy)phenyl]pyridine-3,5-dicarbonitrile and their salts, solvates and solvates of the salts.

The present invention furthermore provides a process for preparing the compounds of the formula (I) according to the invention, characterized in that a compound of the formula (II)

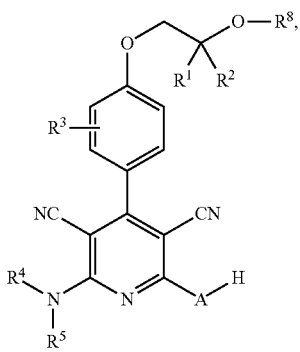

in which A, $R^1$, $R^2$, $R^3$, $R^4$ and $R^5$ each have the meanings given above,
and
$R^8$ represents hydrogen or a temporary hydroxyl protective group
is reacted in an inert solvent in the presence of a base with a compound of the formula (III)

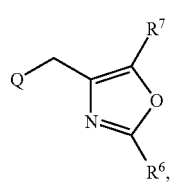

in which $R^6$ and $R^7$ have the meanings given above and
Q represents a suitable leaving group, preferably halogen, in particular chlorine, bromine or iodine, or represents mesylate, tosylate or triflate,
or alternatively, if A represents O, a compound of the formula (IV)

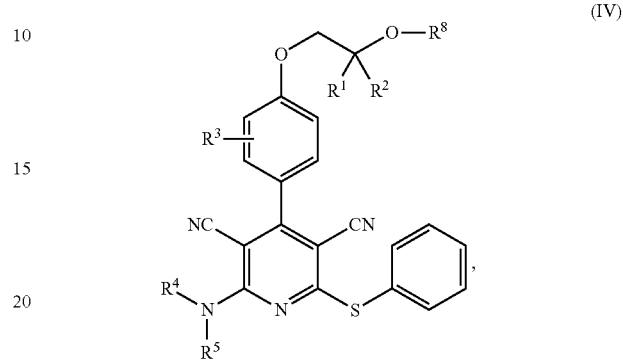

in which $R^1$, $R^2$, $R^3$, $R^4$, $R^5$ and $R^8$ each have the meanings given above
is reacted in an inert solvent in the presence of a base with a compound of the formula (V)

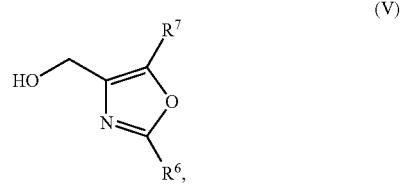

in which $R^6$ and $R^7$ have the meanings given above,
any protective groups present are then removed and the resulting compounds of the formula (I) are, if appropriate, converted with the appropriate (i) solvents and/or (ii) bases or acids into their solvates, salts and/or solvates of the salts.

In this process, if expedient or required, any functional groups present in the compounds of the formulae (II) or (IV) or in the radicals $R^2$, $R^4$ and/or $R^5$— such as, in particular, amino, hydroxyl and carboxyl groups—may also be present in temporarily protected form. Here, the introduction and removal of such protective groups is carried out by customary methods known to the person skilled in the art [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protective groups is present, the removal may be carried out, if appropriate, simultaneously in a one-pot reaction, or in separate reaction steps.

Preferred amino protective groups are tert-butoxycarbonyl (Boc) or benzyloxycarbonyl (Z). Suitable for protecting carboxyl groups are in particular the corresponding methyl, ethyl or tert-butyl esters. For a hydroxyl function, the protective group used is preferably benzyl or a silyl group, such as trimethylsilyl, tert-butyldimethylsilyl or dimethylphenylsilyl. If a 1,2- or 1,3-diol grouping is present, preference is given to using a ketal derived from symmetric ketones such as acetone or cyclohexanone (1,3-dioxolane or 1,3-dioxane) as common protective group.

In an exemplary manner, the process described above can be illustrated by reaction Schemes 1 and 2 below:
Scheme 1
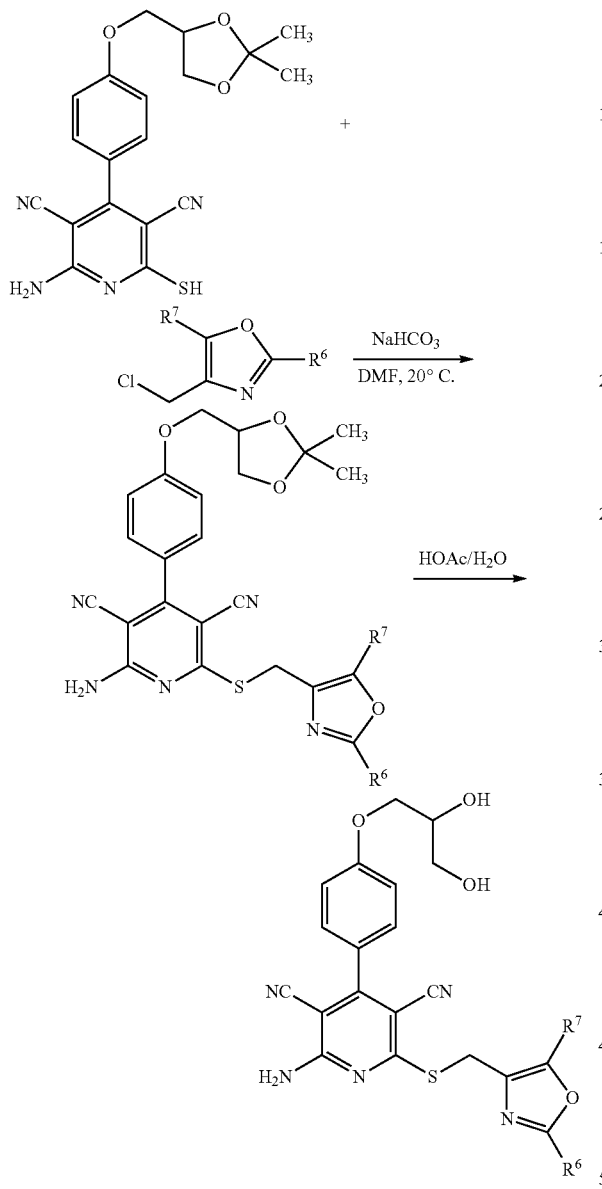
Scheme 2
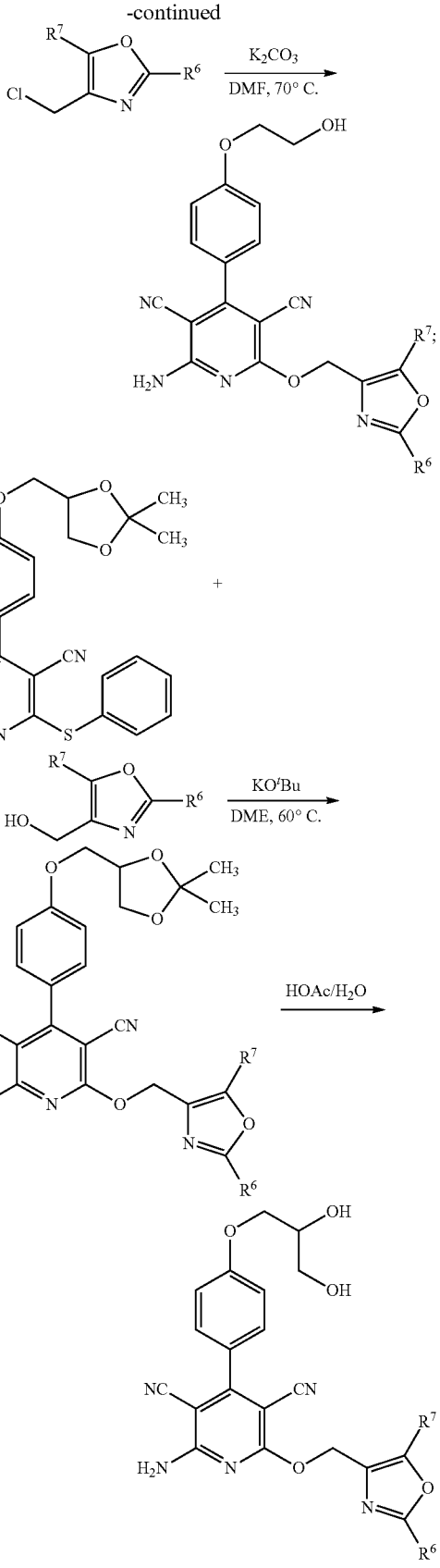
Suitable solvents for the reaction (II)+(III) are all organic solvents which are inert under the reaction conditions. These include ketones, such as acetone and methyl ethyl ketone, acyclic and cyclic ethers, such as diethyl ether, methyl tert-butyl ether, 1,2-dimethoxy ethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. It is also possible to use mixtures of the solvents mentioned above. Preference is given to using dimethylformamide.

Suitable bases for this reaction are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates, such as potassium carbonate and sodium bicarbonate.

Here, the base can be employed in an amount of from 1 to 10 mol, preferably from 1 to 5 mol, in particular from 1 to 3 mol, per mole of the compound of the formula (II).

The reaction (II)+(III) is generally carried out in a temperature range of from −78° C. to +140° C., preferably in the range of from −20° C. to +100° C., in particular at from 0° C. to +60° C. (for A=S) or from +20° C. to +100° C. (for A=O). The reaction can be carried at atmospheric, elevated or reduced pressure (for example in the range of from 0.5 to 5 bar). In general, the reaction is carried out at atmospheric pressure.

Suitable inert solvents for the reaction (IV)+(V) are in particular acyclic and cyclic ethers, such as diethyl ether, methyl tert-butyl ether, 1,2-dimethoxyethane, tetrahydrofuran and dioxane, hydrocarbons, such as benzene, toluene, xylene, hexane and cyclohexane, or dipolar solvents, such as dimethylformamide (DMF), dimethyl sulfoxide (DMSO), N-methylpyrrolidinone (NMP) and pyridine. It is also possible to use mixtures of these solvents. Preference is given to using 1,2-dimethoxyethane.

Suitable bases for this reaction are in particular alkali metal alkoxides, such as sodium methoxide or potassium methoxide, sodium ethoxide or potassium ethoxide, or sodium tert-butoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, per mole of the compound of the formula (V).

The reaction (IV)+(V) is generally carried out in a temperature range of from −20° C. to +120° C., preferably at from +20° C. to +100° C. The reaction can be carried out at atmospheric, elevated or reduced pressure (for example in the range of from 0.5 to 5 bar). In general, the reaction is carried out at atmospheric pressure.

Analogously to methods known from the literature, compounds of the formula (II) in which A represents S and $R^4$ and $R^5$ represent hydrogen can be prepared, for example, by reacting aldehydes of the formula (VI)

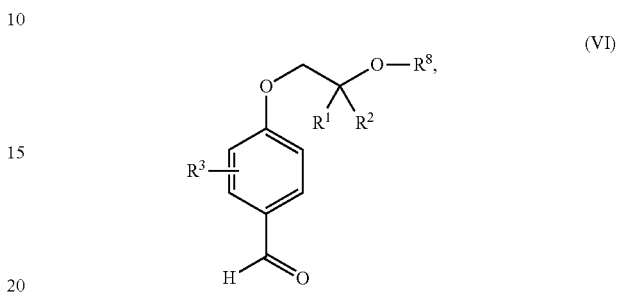

in which $R^1$, $R^2$, $R^3$ and $R^8$ each have the meanings given above in the presence of a base with two equivalents of cyanothioacetamide [see Scheme 3; cf., for example, Dyachenko et al., *Russ. J. Chem.* 33 (7), 1014-1017 (1997), 34 (4), 557-563 (1998); Dyachenko et al., *Chemistry of Heterocyclic Compounds* 34 (2), 188-194 (1998); Qintela et al., *Eur. J. Med. Chem.* 33, 887-897 (1998); Kandeel et al., *Z. Naturforsch.* 42b, 107-111 (1987); Reddy et al., *J. Med. Chem.* 49, 607-615 (2006); Evdokimov et al., *Org. Lett.* 8, 899-902 (2006)].

Scheme 3

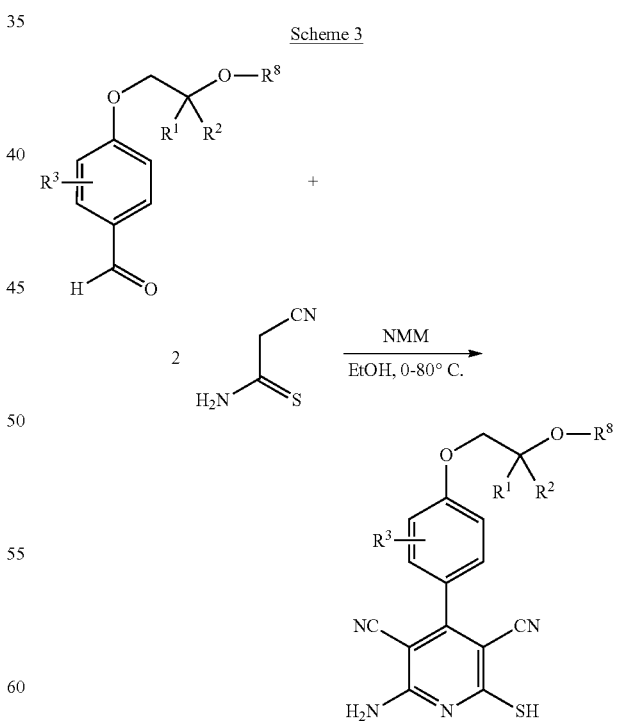

Compounds of the formula (II) in which A represents S can also be prepared from compounds of the formula (IV) by reaction with an alkali metal sulfide. This preparation method is illustrated by the formula Scheme below:

Scheme 4

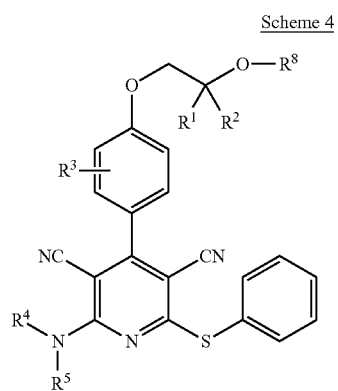

Na₂S →

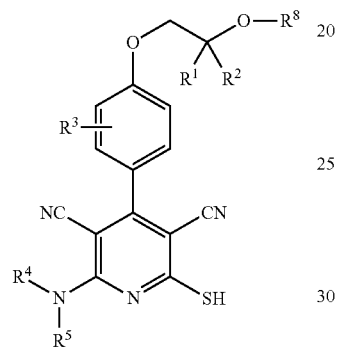

The alkali metal sulfide used is preferably sodium sulfide in an amount of from 1 to 10 mol, preferably from 1 to 8 mol, in particular from 1 to 5 mol, per mole of the compound of the formula (IV).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or dipolar solvents, such as acetonitrile, pyridine, dimethylformamide, dimethyl sulfoxide or n-methylpyrrolidinone. Water is likewise suitable for use as solvents. It is also possible to use mixtures of the solvents mentioned above. The preferred solvent is dimethylformamide.

The reaction is generally carried out in a temperature range of from 0° C. to +180° C., preferably in the range of from +20° C. to +120° C., in particular at from +40° C. to +100° C. The reaction can be carried out at atmospheric, elevated or reduced pressure (for example in the range of from 0.5 to 5 bar). In general, the reaction is carried out under atmospheric pressure.

Compounds of the formula (IV) in which at least one of the two radicals $R^4$ and $R^5$ does not represent hydrogen can be prepared by converting compounds of the formula (IVa)

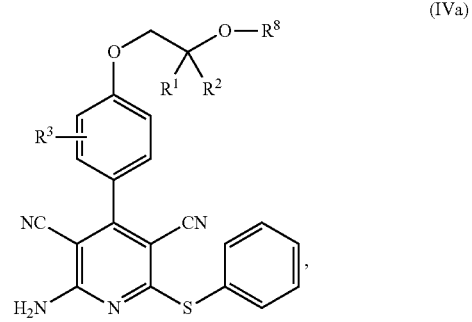

(IVa)

in which $R^1$, $R^2$, $R^3$ and $R^8$ each have the meanings given above initially with copper(II) chloride and isoamyl nitrite in a suitable solvent into compounds of the formula (VII)

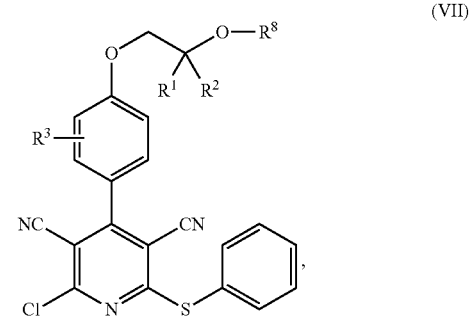

(VII)

in which $R^1$, $R^2$, $R^3$ and $R^8$ each have the meanings given above, followed by reaction with a compound of the formula (VIII)

$$R^{4A}\underset{H}{\overset{}{N}}R^{5A},$$

(VIII)

in which $R^{4A}$ has the meaning of $R^4$ given above,
$R^{5A}$ has the meaning of $R^5$ given above,
but at least one of the two radicals does not represent hydrogen,
to give compounds of the formula (IVb)

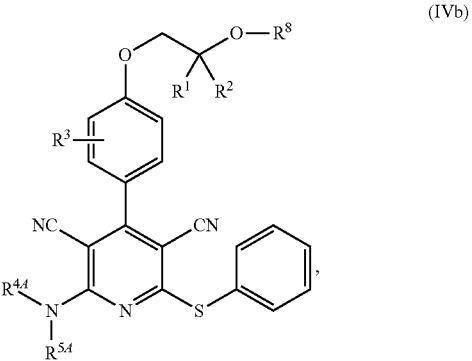

(IVb)

in which $R^1$, $R^2$, $R^3$, $R^{4A}$, $R^{5A}$ and $R^8$ each have the meanings given above;

if appropriate, these can then be converted with the aid of an alkali metal sulfide as described above into corresponding compounds of the formula (II) in which A represents S and at least one of the two radicals $R^4$ and $R^5$ does not represent hydrogen. This process can be illustrated by the reaction Scheme below:

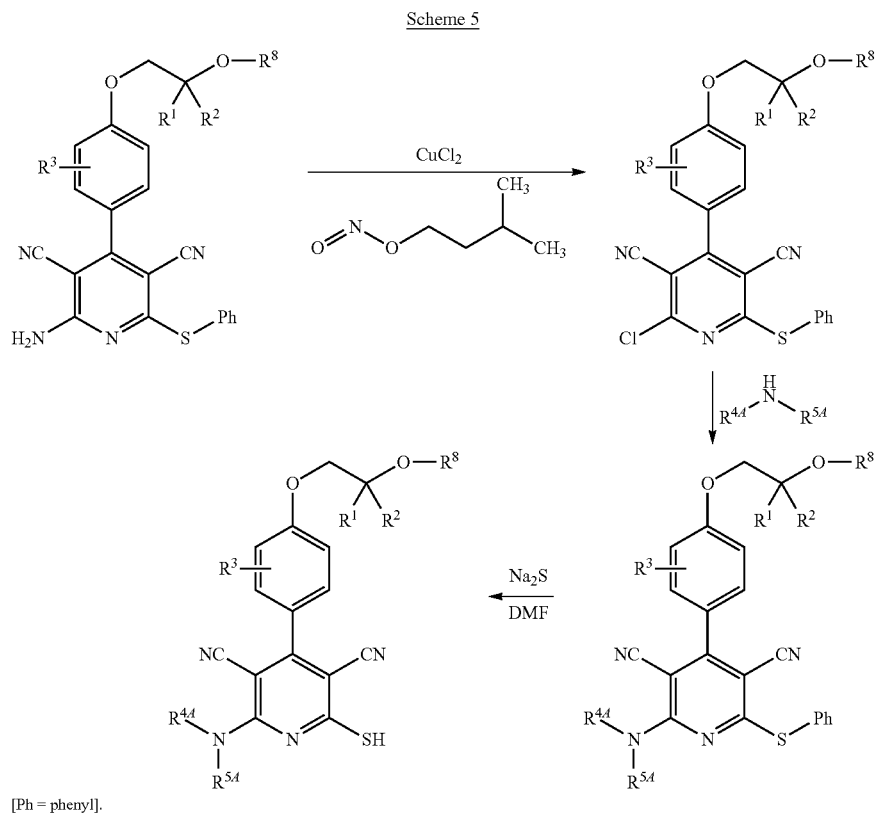

Scheme 5

[Ph = phenyl].

The process step (IVa)→(VII) is generally carried out using a molar ratio of from 2 to 12 mol of copper(II) chloride and from 2 to 12 mol of isoamyl nitrite per mole of the compound of the formula (IVa).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of these solvents. Preferred solvents are acetonitrile and dimethylformamide.

The reaction is generally carried out in a temperature range of from −78° C. to +180° C., preferably in a range of from +20° C. to +100° C., in particular at from +20° C. to +60° C. The reaction can be carried out at atmospheric, elevated or reduced pressure (for example in the range of from 0.5 to 5 bar). In general, the reaction is carried out at atmospheric pressure.

The process step (VII)+(VIII)→(IVb) is generally carried out using a molar ratio of from 1 to 8 mol of the compound of the formula (VIII) per mole of the compound of the formula (VII).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulfoxide. Water is likewise suitable for use as solvent. It is also possible to use mixtures of these solvents. The preferred solvent is dimethylformamide.

The reaction is generally carried out in a temperature range of from 0° C. to +180° C., preferably in a range of from +20° C. to +120° C., in particular at from +20° C. to +100° C. The reaction can be carried out at atmospheric, elevated or reduced pressure (for example in the range of from 0.5 to 5 bar). In general, the reaction is carried out at atmospheric pressure.

The compounds of the formula (IVa) can be prepared from compounds of the formula (VI) analogously to processes described in the literature [cf., for example, Kambe et al., *Synthesis*, 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)].

The compounds of the formula (VIII) are either commercially available, known to the person skilled in the art or preparable by customary methods.

If appropriate, it is also possible to convert compounds of the formula (I) in which $R^4$ and $R^5$ both represent hydrogen analogously to the reaction sequence (IVa)→(VII)→(IVb) into the corresponding compounds in which at least one of the two radicals R⁴ and R⁵ does not represent hydrogen, where, if appropriate, a temporary protection of other functional groups is expedient. This process variant is illustrated in the reaction Scheme below:

Scheme 6

Scheme 7

For this process route, the reaction parameters, such as solvents, reaction temperatures and molar ratios, described above for the sequence (IVa)→(VII)→(IVb) are used in an analogous manner Compounds of the formula (II) in which A represents O can be obtained from compounds of the formula (IV) by heating with an alkali metal hydroxide. This preparation method is illustrated by the reaction Scheme below:

The alkali metal hydroxide used is preferably excess sodium hydroxide or potassium hydroxide. Suitable solvents are in particular alcohols, such as methanol, ethanol, n-propanol, isopropanol, n-butanol and tert-butanol, and also mixtures thereof with water. The reaction is generally carried out in a temperature range of from +20° C. to +120° C., preferably at from +50° C. to +100° C.

The compounds of the formula (III) are commercially available, known from the literature or preparable by methods known from the literature. By reacting amides with a 1,3-dihaloacetone, for example, it is possible to obtain 2-substituted oxazole derivatives (see Scheme 8):

Scheme 8

2,5-Disubstituted oxazole derivatives according to formula (III) can be prepared analogously to processes known from the literature, for example as described in an exemplary manner in reaction Scheme 9 below:

Scheme 9

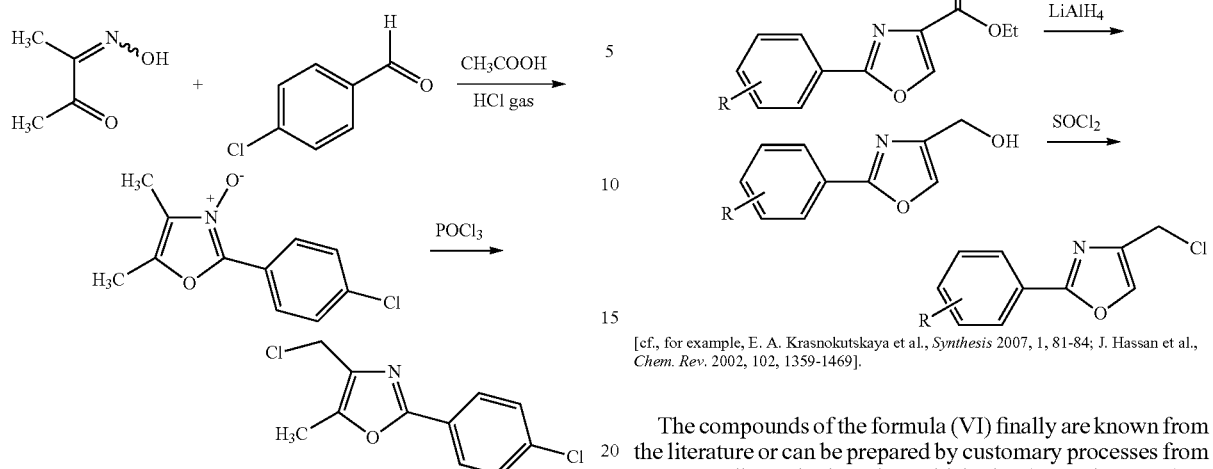

[cf., for example, Y. Goto et al., *Chem. Pharm. Bull.* 1971, 19, 2050-2057].

Oxazole derivatives substituted in the 5-position according to formula (III) can be obtained, for example, by reduction and subsequent halogenation of corresponding oxazole-4-carboxylic esters which for their part are accessible by acylation of α-isocyanatoacetates (see Scheme 10):

Scheme 10

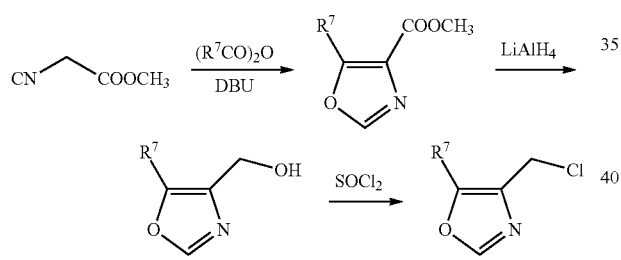

[cf., for example, M. Suzuki et al., *J. Org. Chem.* 1973, 38, 3571-3575].

2-Aryloxazole derivatives according to formula (III) can also be obtained via palladium-catalyzed coupling of arylboronic acids with 2-iodooxazole-4-carboxylic esters as shown in an exemplary manner in Scheme 11:

Scheme 11

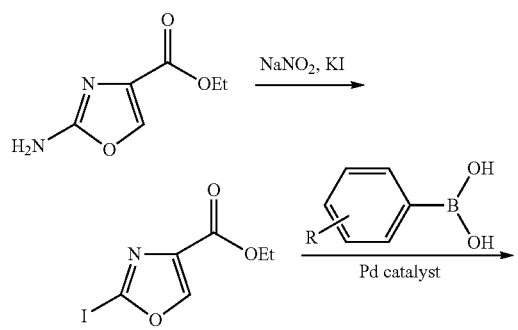

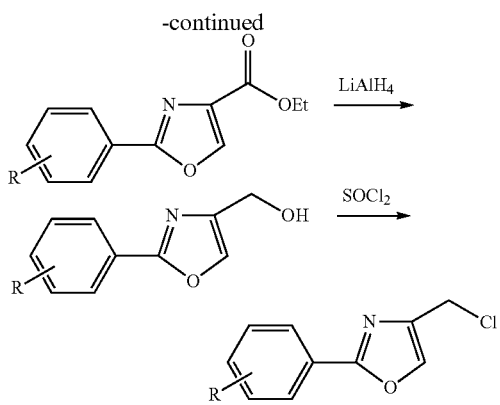

[cf., for example, E. A. Krasnokutskaya et al., *Synthesis* 2007, 1, 81-84; J. Hassan et al., *Chem. Rev.* 2002, 102, 1359-1469].

The compounds of the formula (VI) finally are known from the literature or can be prepared by customary processes from corresponding 4-hydroxybenzaldehydes (see Scheme 12):

Scheme 12

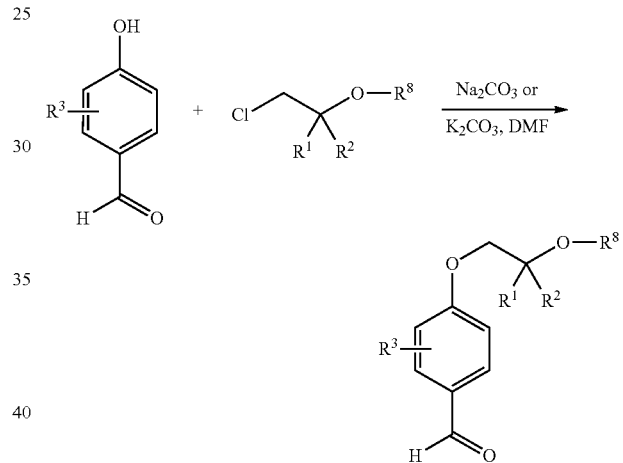

Surprisingly, the compounds according to the invention have an unforeseeable useful pharmacological activity spectrum and are therefore particularly suitable for the prophylaxis and/or treatment of disorders, in particular cardiovascular disorders.

Compared to the substances known from the prior art, the compounds according to the invention have an improved property profile such as, for example, increased solubility in aqueous/organic solvent systems relevant for the formulation, a longer pharmacokinetic half-life after oral administration and/or increased metabolic stability.

The pharmacological activity of the compounds according to the invention can be explained by their action as potent, selective ligands at adenosine A1 and/or A2b receptors. Here, they act as selective A1 agonists or as selective dual A1/A2b agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Depending on their respective structure, the compounds according to the invention act as full or as partial adenosine receptor agonists. Here, partial adenosine receptor agonists are defined as receptor ligands which trigger a functional response at adenosine receptors which is less than that triggered by full agonists (such as, for example, adenosine itself). Accordingly, partial agonists have a lower activity with respect to receptor activation than full agonists.

The compounds of the formula (I), on their own or in combination with one or more other active compounds, are suitable for the prophylaxis and/or treatment of various disorders such as, for example, in particular hypertension and other disorders of the cardiovascular system (cardiovascular disorders), for cardioprotection following damage of the heart and for metabolic disorders.

In the context of the present invention, disorders of the cardiovascular system or cardiovascular disorders are to be understood as including, in addition to hypertension, for example the following disorders: peripheral and cardial vascular disorders, coronary heart disease, coronary restenosis, such as, for example, restenosis after balloon dilation of peripheral blood vessels, myocarcial infarction, acute coronary syndrome, acute coaronary syndrome with ST elevation, acute coronary syndrome without ST elevation, stable and unstable angina pectoris, myocardial insufficiency, Prinzmetal's angina, persistent ischemic dysfunction ("hibernating myocardium"), transient postischemic dysfunction ("stunned myocardium"), heart failure, tachycardias, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, impaired peripheral circulation, increased levels of fibrinogen and LDL of low density and also increased concentrations of plasminogen activator inhibitor 1 (PAI-1), in particular hypertension, coronary heart disease, acute coronary syndrome, angina pectoris, heart failure, myocardial infarction and atrial fibrillation.

In the context of the present invention, the term heart failure includes both acute and chronic manifestations of heart failure, and also specific or related forms of the disease, such as acute decompensated heart failure, right-sided heart failure, left-sided heart failure, global failure, ischemic cardiomyopathy, dilative cardiomyopathy, congenital heart defects, valvular defects, heart failure as a result of valvular defects, mitral stenosis, mitral insufficiency, aortic stenosis, aortic insufficiency, tricuspid stenosis, tricuspid insuffuciency, pulmonary stenosis, pulmonary insufficiency, combined valvular defects, myocarditis, chronic myocarditis, acute myocarditis, viral myocarditis, diabetic heart failure, alcohol-toxic cardiomyopathy, cardial storage diseases and also diastolic and systolic heart failure.

The compounds according to the invention are furthermore also particularly suitable for reducing the myocard region affected by an infarct, and also for the prophylaxis of secondary infarcts.

Furthermore, compounds according to the invention are particularly suitable for the prophylaxis and/or treatment of thromboembolic disorders, reperfusion damage after ischemia, micro- and macrovascular damage (vasculitis), arterial and venous thromboses, edemas, ischemias, such as myocardial infarction, stroke and transitory ischemic attacks, for cardioprotection during coronary artery bypass grafting (CABG), primary percutaneous-transluminal coronary angioplasties (PTCAs), PTCAs after thrombolysis, rescue-PTCA, heart transplantations and open heart operations, and also for organ protection during transplantations, bypass operations, catheter examinations and other surgical interventions.

Further indications for which the compounds according to the invention may be used are, for example, the prophylaxis and/or treatment of disorders of the urogenital system, such as, for example, in irritable bladder, erectile dysfunction and female sexual dysfunction, but in addition also the prophylaxis and/or treatment of inflammatory disorders, such as, for example, asthma and inflammatory dermatoses, of disorders of the central nervous system and neurodegenerative disorders (stroke, Alzheimer's disease, Parkinson's disease, dementia, epilepsy, depressions, multiple sclerosis), of pain, and also of neoplastic diseases and nausea and emesis associated with cancer therapies.

A further indication is, for example, the prophylaxis and/or treatment of disorders of the respiratory tract, such as, for example, asthma, chronic-obstructive pulmonary diseases (COPD, chronic bronchitis), pulmonary emphysema, bronchiectasias, cystic fibrosis (mucoviscidosis) and pulmonary hypertension, in particular pulmonary arterial hypertension.

Finally, the compounds according to the invention are also suitable for the prophylaxis and/or treatment of metabolic disorders such as, for example, diabetes, in particular diabetes mellitus, gestation diabetes, insulin-dependent diabetes and non-insulin-dependent diabetes, diabetic sequelae, such as, for example, retinopathy, nephropathy and neuropathy, metabolic disorders, such as, for example, metabolic syndrome, hyperglycemia, hyperinsulinemia, insulin resistance, glucose intolerance and obesity (adipositas), and also arteriosclerosis and dyslipidemias (hypercholesterolemia, hypertriglyceridemia, elevated concentrations of postprandial plasma triglycerides, hypoalphalipoproteinemia, combined hyperlipidemias), in particular diabetes, metabolic syndrome and dyslipidemias.

The present invention furthermore provides the use of the compounds according to the invention for the treatment and/or prevention of disorders, in particular the disorders mentioned above.

The present invention also provides the use of the compounds according to the invention for preparing a medicament for the treatment and/or prevention of disorders, in particular the disorders mentioned above.

The present invention also provides a method for the treatment and/or prevention of disorders, in particular the disorders mentioned above, using an effective amount of at least one compound according to the invention.

The compounds according to the invention can be used alone or, if required, in combination with other active compounds. The present invention furthermore provides medicaments comprising at least one compound according to the invention and one or more further active compounds, in particular for the treatment and/or prevention of the disorders mentioned above.

Suitable active compounds for combinations are, by way of example and by way of preference: active compounds which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists) and analgesics such as for example aspirin.

The present invention provides in particular combinations comprising at least one of the compounds according to the invention and at least one lipid metabolism-modulating active compound, an antidiabetic, a hypotensive active compound and/or an antithrombotic agent.

Preferably, the compounds according to the invention can be combined with one or more lipid metabolism-modulating active compounds, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulphonylureas, biguanides, meglitinide derivatives, glucosidase inhibitors, inhibitors of dipeptidyl-peptidase IV (DDP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active compounds, by way of example and by way of preference from the group of the calcium antagonists, angiotensin AII antagonists, ACE inhibitors, renin inhibitors, beta-receptor blockers, alpha-receptor blockers, diuretics, aldosterone antagonists, mineralocorticoid receptor antagonists, ECE inhibitors and the vasopeptidase inhibitors;

antithrombotic agents, by way of example and by way of preference from the group of the platelet aggregation inhibitors or the anticoagulants;

vasopressin receptor antagonists;

organic nitrates and NO donors;

positive inotropically active compounds;

compounds which inhibit the degradation of cyclic guanosine monophosphate (cGMP) and/or cyclic adenosine monophosphate (cAMP), such as, for example, inhibitors of the phosphodiesterases (PDE) 1, 2, 3, 4 and/or 5, in particular PDE 5 inhibitors such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, for example, iloprost, beraprost and cicaprost;

calcium sensitizers, such as, by way of example and by way of preference, levosimendan;

potassium supplements;

NO- and heme-independent activators of guanylate cyclase, such as, in particular, compounds described in WO 01/19355, WO 01/19776, WO 01/19778, WO 01/19780, WO 02/070462 and WO 02/070510;

NO-independent, but heme-dependent stimulators of guanylate cyclase, such as, in particular, the compounds described in WO 00/06568, WO 00/06569, WO 02/42301 and WO 03/095451;

inhibitors of human neutrophile elastase (HNE), such as, for example, sivelestat and DX-890 (Reltran);

compounds which inhibit the signal transduction cascade, such as, for example, tyrosine kinase inhibitors, in particular sorafenib, imatinib, gefitinib and erlotinib; and/or compounds which moderate the energy metabolism of the heart, such as, for example, etomoxir, dichloroacetate, ranolazine and trimetazidine.

Lipid metabolism-modifying active compounds are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active compounds. Here, insulin and insulin derivatives include both insulins of animal, human or biotechnological origin and also mixtures thereof. The orally effective hypoglycemic active compounds preferably include sulphonylureas, biguanides, meglitinide derivatives, glucosidase inhibitors, DDP-IV inhibitors and PPAR-γ agonists.

In a preferred embodiment of the invention, the compounds according to the invention are administered in combination with insulin.

In a preferred embodiment of the invention, the compounds according to the invention are administered in combination with a sulphonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin or vildagliptin.

In a preferred embodiment of the invention, the compounds according to the invention are administered in combination with a PPAR-γ agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, renin inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, almesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a renin inhibitor, such as, by way of example and by way of preference, aliskiren, SPP-600 or SPP-800.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example, and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, glycerol nitrate, isosorbide mononitrate, isosorbide dinitrate, molsidomine or SIN-1, or in combination with inhalative NO.

In a preferred embodiment of the invention, the compounds according to the invention are administered in combination with a positive-inotropically active compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

For the purposes of the present invention, particular preference is given to combinations comprising at least one of the compounds according to the invention and one or more further active compounds selected from the group consisting of HMG-CoA reductase inhibitors (statins), diuretics, beta receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also to their use for the treatment and/or prophylaxis of the disorders mentioned above.

The present invention furthermore provides medicaments comprising at least one compound according to the invention, usually together with one or more inert nontoxic pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active compound, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used

Ex. Example
DBU 1,8-diazabicyclo[5.4.0]undec-7-ene
TLC thin-layer chromatography
DCI direct chemical ionization (in MS)
DME 1,2-dimethoxyethane
DMF N,N-dimethylformamide
DMSO dimethyl sulfoxide
EA ethyl acetate
EI electron impact ionization (in MS)
ESI electrospray ionization (in MS)
Et ethyl
EtOH ethanol
m.p. melting point
sat. saturated
h hour(s)
HOAc acetic acid
HPLC high-pressure, high-performance liquid chromatography
conc. concentrated
KO$^t$Bu potassium tert-butoxide
LC-MS liquid chromatography-coupled mass spectrometry
LDA lithium diisopropylamide
lit. literature (reference)
sol. solution
min minute(s)
MS mass spectrometry
NMM N-methylmorpholine
NMR nuclear magnetic resonance spectrometry
PBS phosphate-buffered saline
PEG polyethylene glycol
Ph phenyl
RP-HPLC reversed-phase HPLC
RT room temperature
R$_t$ retention time (in HPLC)
THF tetrahydrofuran
dil. dilute
aq. aqueous
HPLC and LC-MS Methods:

Method 1 (HPLC):
Instrument: Hewlett Packard Series 1050; column: Symmetry TM C18 3.9×150 mm; flow rate: 1.5 ml/min; mobile phase A: water, mobile phase B: acetonitrile; gradient:→0.6 min 10% B→3.8 min 100% B→5.0 min 100% B→5.5 min 10% B; stop time: 6.0 min; injection volume: 10 µl; diode array detector signal: 214 and 254 nm.

Method 2 (LC-MS):
MS instrument type: Micromass ZQ; HPLC instrument type: Waters Alliance 2795; column: Merck Chromolith SpeedROD RP-18e 100 mm×4.6 mm; mobile phase A: water+500 µl of 50% strength formic acid/1, mobile phase B: acetonitrile+500 µl 50% strength formic acid/1; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Methods 3 (LC-MS):
MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS):
Instrument: Micromass Quattro LCZ with HPLC Agilent Series 1100; column: Phenomenex Onyx monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 5 (LC-MS):
MS instrument type: Waters ZQ; HPLC instrument type: Waters Alliance 2795; column: Merck Chromolith RP-18e, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 6 (LC-MS):
Instrument: Micromass Quattro LCZ with HPLC Agilent Series 1100; column: Phenomenex Synergi 2.5µ MAX-RP 100A Mercury 20 mm×4 mm; mobile phase A: 1 l of water+ 0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 7 (LC-MS):
MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8 (LC-MS):
Instrument: Micromass Platform LCZ with HPLC Agilent Series 1100; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; flow rate: 0.8 ml/min; oven: 50° C.; UV detection: 210 nm.

Method 9 (LC-MS):
Instrument: Micromass Quattro LCZ with HPLC Agilent Series 1100; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 10 (LC-MS):
MS instrument type: Micromass ZQ; HPLC instrument type: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 11 (LC-MS):

MS instrument type: Micromass ZQ; HPLC instrument type: HP 1100 Series; UV DAD; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 210 nm.

Method 12 (LC-MS):

MS instrument type: Micromass ZQ; HPLC instrument type: Waters Alliance 2795; column: Merck Chromolith SpeedROD RP-18e 100 mm×4.6 mm; mobile phase A: water+500 μl 50% strength formic acid/1; mobile phase B: acetonitrile+500 μl 50%-ige formic acid/1; gradient: 0.0 min 10% B→7.0 min 95% B→9.0 min 95% B; flow rate: 0.0 min 1.0 ml/min→7.0 min 2.0 ml/min→9.0 min 2.0 ml/min; oven: 35° C.; UV detection: 210 nm.

Method 13 (LC-MS):

MS instrument type: M-40 DCI (NH$_3$); HPLC instrument type: HP 1100 with DAD detection; column: Kromasil 100 RP-18, 60 mm×2.1 mm, 3.5 μm; mobile phase A: 5 ml of HClO$_4$ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 14 (LC-MS):

Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 15 (LC-MS):

Instrument: Micromass Quattro Micro MS with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 16 (preparative HPLC):

HPLC instrument type: Abimed/Gilson Pump 305/306; Manometric Module 806; UV Knauer Variable Wavelength Monitor; column: Gromsil C18, 10 nm, 250 mm×30 mm; mobile phase A: 1 l of water+0.5 ml of 99% strength trifluoracetic acid, mobile phase B: 1 l of acetonitrile; gradient: 0.0 min 2% B→10 min 2% B→50 min 90% B; flow rate: 20 ml/min; volume: 628 ml of A and 372 ml of B.

Method 17 (HPLC):

HPLC instrument type: Agilent 1100 with DAD detection; column: Merck Chromolith SpeedROD RP-18e, 50 mm×4.6 mm; mobile phase A: 0.05% strength H$_3$PO$_4$, mobile phase B: acetonitrile; gradient: 0 min 5% B→2.5 min 95% B→3.0 min 95% B; flow rate: 5 ml/min; column temperature: 40° C.; UV detection: 210 nm.

Starting Materials and Intermediates

Example 1A

2-Amino-4-[4-(2-hydroxyethoxy)phenyl]-6-mercaptopyridine-3,5-dicarbonitrile

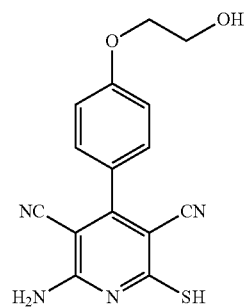

14.90 g (89.66 mmol) of 4-(2-hydroxyethoxy)benzaldehyde and 17.96 g (179.33 mmol) of cyanothioacetamide are initially charged in 280 ml of ethanol. 18.14 g (179.33 mmol) of 4-methylmorpholine are then added. The reaction mixture is heated under reflux for 4 h and then stirred at RT for a further 20 h. The resulting precipitate is filtered off with suction, washed with about 20 ml of ethanol and dried.

Yield: 9.90 g (35% of theory)

LC-MS (method 10): R$_t$=1.63 min; MS (ESIpos): m/z=313 [M+H]$^+$.

Example 2A 4-(2-Hydroxy-2-methylpropoxy)benzaldehyde

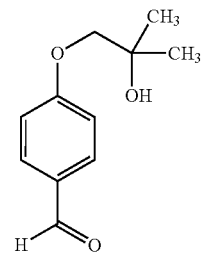

5.00 g (40.94 mmol) of 4-hydroxybenzaldehyde, 4.44 g (40.94 mmol) of 1-chloro-2-methyl-2-propanol and 6.08 g (57.32 mmol) of sodium carbonate are initially charged in 50 ml of dry DMF and stirred under reflux for 24 h. After cooling to RT, 20 ml of ethyl acetate and 20 ml of sat. aqueous sodium bicarbonate solution are added. The phases are separated, and the organic phase is dried over magnesium sulfate. After removal of the solvent, the residue is purified by column chromatography on silica gel 60 (mobile phase gradient: cyclohexane/ethyl acetate 5:1→1:1). This gives a reddish solid which is used without further purification for the subsequent step.

Yield: 4.40 g (50% of theory, 90% purity)

LC-MS (method 2): R$_t$=1.37 min; MS (ESIpos): m/z=195 [M+H]$^+$.

Example 3A

2-Amino-4-[4-(2-hydroxy-2-methylpropoxy)phenyl]-6-mercaptopyridine-3,5-dicarbonitrile

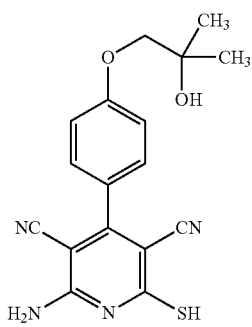 [SMILES: CC(C)(O)COc1ccc(-c2c(C#N)c(N)nc(S)c2C#N)cc1]

3.38 g (15.49 mmol) of the compound from Example 2A and 3.26 g (32.52 mmol) of cyanothioacetamide are initially charged in 50 ml of ethanol. 3.13 g (30.98 mmol) of 4-methylmorpholine are then added. With stirring, the mixture is heated at reflux for 6 h. After cooling to RT, the mixture is stirred at this temperature for 20 h. 50 ml of sat. aqueous sodium bicarbonate solution are then added, and the mixture is extracted four times with in each case 50 ml of ethyl acetate. The combined organic phases are dried over magnesium sulfate. After removal of the solvent, the residue is purified by column chromatography on silica gel 60 (mobile phase gradient: cyclohexane/ethyl acetate 2:1→1:4). The product obtained is used without further purification for the subsequent step.

Yield: 0.92 g (16% of theory, 90% purity)

$^1$H-NMR (400 MHz, DMSO-$d_6$): δ=13.00-12.91 (br. s, 1H), 8.09-7.78 (br. s, 2H), 7.46 (d, 2H), 7.09 (d, 2H), 4.68 (s, 1H), 3.79 (s, 2H), 1.22 (s, 6H).

LC-MS (method 2): $R_t$=1.46 min; MS (ESIpos): m/z=341 [M+H]$^+$.

Example 4A (2S)-1-Chloropropan-2-ol

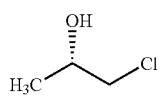

32.50 g (766.66 mmol) of lithium chloride are initially charged in 100 ml of THF. 18.75 ml (92.97 mmol) of 4.96 M hydrochloric acid are then added. The mixture is cooled to −30° C., and a solution of 5.40 g (92.97 mmol) of S-(−)-propylene oxide in 10 ml of THF is added dropwise. After the addition, the mixture is warmed to RT and stirred for 20 h. The precipitate formed is filtered off with suction, and the filtrate is subjected to fractional distillation (61 mbar, 30-40° C. head temperature). The product mixture obtained in this manner is used without further purification in the subsequent step.

Yield: 4.50 g (16% of theory, 32% purity)

$^1$H-NMR (400 MHz, DMSO-$d_6$): δ=5.01 (d, 1H), 3.85-3.74 (m, 1H), 3.49 (d, 2H), 1.12 (d, 3H).

The product contains about 10% of the regioisomer (2S)-2-chloropropan-1-ol:

$^1$H-NMR (400 MHz, DMSO-$d_6$): δ=5.18-5.12 (m, 1H), 4.11-4.03 (m, 1H), 3.49 (d, 2H), 1.41 (d, 3H).

Example 5A

4-{[(2S)-2-Hydroxypropyl]oxy}benzaldehyde

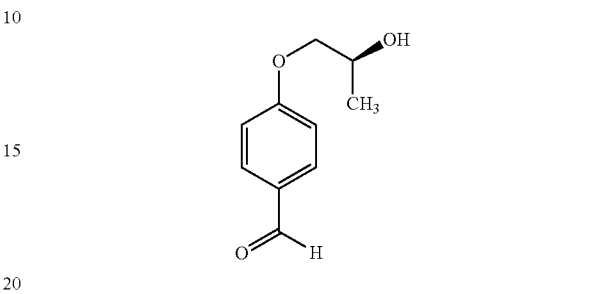

6.30 g (51.62 mmol) of 4-hydroxybenzaldehyde and 4.88 g (51.62 mmol) of the product from Example 4A are dissolved in 100 ml of dry DMF. 16.41 g (154.85 mmol) of sodium carbonate are added to the solution, and the mixture is stirred at 130° C. for 20 h. After cooling to RT, 100 ml of ethyl acetate and 50 ml of sat. aqueous sodium bicarbonate solution are added to the mixture. The mixture is extracted three times with in each case 50 ml of ethyl acetate. The combined organic phases are dried over magnesium sulfate. After removal of the solvent, the residue is purified by column chromatography on silica gel 60 (mobile phase gradient: cyclohexane/ethyl acetate 5:1→2:1).

Yield: 2.40 g (26% of theory)

$^1$H-NMR (400 MHz, DMSO-$d_6$): δ=7.86 (d, 2H), 7.13 (d, 2H), 4.95 (d, 1H), 4.02-3.92 (m, 1H), 3.91 (d, 2H), 1.16 (d, 3H).

LC-MS (method 2): $R_t$=1.19 min; MS (ESIpos): m/z=181 [M+H]$^+$.

The product contains about 10% of the regioisomer 4-[(1S)-2-hydroxy-1-methylethoxy]benzaldehyde.

Example 6A

4-{[(2S)-2-{[tert-Butyl(dimethyl)silyl]oxy}propyl]oxy}benzaldehyde

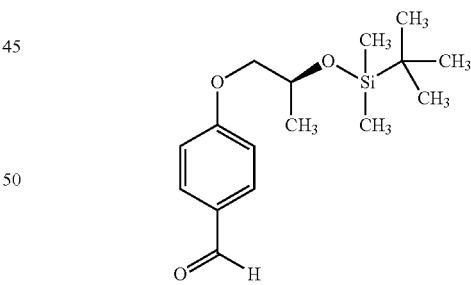

2.40 g (13.32 mmol) of the compound from Example 5A are initially charged in 60 ml of dry DMF, and 2.81 g (18.65 mmol) of tert-butyldimethylsilyl chloride and 1.72 g (25.30 mmol) of imidazole are added. The reaction mixture is stirred at RT for 20 h. About 30 ml of diethyl ether and 30 ml of sat. aqueous sodium bicarbonate solution are then added to the mixture. The phases are separated and the aqueous phase is extracted twice with in each case 30 ml of diethyl ether. The combined organic phases are dried over magnesium sulfate and the solvent is removed on a rotary evaporator. The residue is purified by column chromatography on silica gel 60 (mobile phase gradient: cyclohexane/ethyl acetate 50:1→10:1).

Yield: 1.95 g (50% of theory)

¹H-NMR (400 MHz, DMSO-d₆): δ=7.82 (d, 2H), 7.07 (d, 2H), 4.18-4.11 (m, 1H), 3.98 (dd, 1H), 3.87 (dd, 1H), 1.13 (d, 3H), 0.81 (s, 9H), 0.3 (s, 3H), 0.1 (s, 3H).

LC-MS (method 9): $R_t$=3.30 min; MS (ESIpos): m/z=295 [M+H]⁺.

The product contains about 10% of the regioisomer 4-[(1S)-2-{[tert-butyl(dimethyl)silyl]oxy}-1-methylethoxy] benzaldehyde.

Example 7A

2-Amino-4-(4-{[(2S)-2-{[tert-butyl(dimethyl)silyl]oxy}propyl]oxy}phenyl)-6-mercaptopyridine-3,5-dicarbonitrile

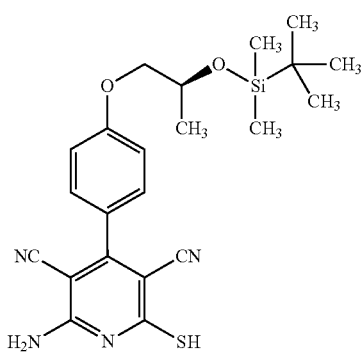 [SMILES: C[C@@H](COc1ccc(-c2c(C#N)c(N)nc(S)c2C#N)cc1)O[Si](C)(C)C(C)(C)C]

1.95 g (6.62 mmol) of the compound from Example 6A and 1.39 g (13.91 mmol) of cyanothioacetamide are initially charged in 27 ml of ethanol, and 1.34 g (13.24 mmol) of 4-methylmorpholine are added. The mixture is heated under reflux for 6 h (oil bath temperature 100° C.). The mixture is then stirred at RT for a further 20 h. After removal of the solvent on a rotary evaporator, the residue is purified directly by column chromatography on silica gel 60 (mobile phase gradient: dichloromethane/ethanol 50:1→5:1).

Yield: 1.30 g (29% of theory, 65% purity)

¹H-NMR (400 MHz, DMSO-d₆): δ=7.68-7.48 (br. s, 2H), 7.42 (d, 2H), 7.06 (d, 2H), 4.23-4.15 (m, 1H), 3.96 (dd, 1H), 3.88 (dd, 1H), 1.20 (d, 3H), 0.89 (s, 9H), 0.09 (s, 3H), 0.07 (s, 3H).

LC-MS (method 2): $R_t$=2.79 min; MS (ESIpos): m/z=441 [M+H]⁺.

The product contains about 10% of the regioisomer 2-amino-4-[4-[(1S)-2-{[tert-butyl(dimethyl)-silyl]oxy}-1-methylethoxy]phenyl]-6-mercaptopyridine-3,5-dicarbonitrile.

Example 8A

4-{[(4R)-2,2-Dimethyl-1,3-dioxolan-4-yl]methoxy}benzaldehyde

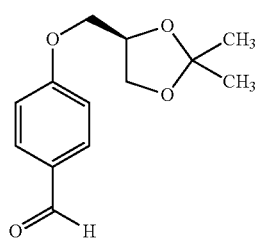 [SMILES: CC1(C)OC[C@@H](COc2ccc(C=O)cc2)O1]

31.2 g (255.4 mmol) of 4-hydroxybenzaldehyde are initially charged in 400 ml of dry DMF, and 105.7 g (766.1 mmol) of potassium carbonate and 50.0 g (332.0 mmol) of (S)-(−)-3-chloro-1,2-propanediol acetonide are added at RT. The mixture is stirred at 160° C. for 16 h. 4000 ml of water are then added, and the mixture is extracted three times with in each case 500 ml of ethyl acetate. The combined organic phases are washed in each case once with 500 ml water and 500 ml of sat. aqueous sodium chloride solution. After drying over magnesium sulfate, the solvent is removed on a rotary evaporator and the residue is purified by column chromatography on silica gel 60 (mobile phase gradient: ethyl acetate/petroleum ether 1:9→2:8).

Yield: 40.4 g (63% of theory)

¹H-NMR (400 MHz, DMSO-d₆): δ=9.90 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

LC-MS (method 13): $R_t$=3.97 min; MS (ESIpos): m/z=254 [M+NH₄]⁺.

Example 9A

4-{[(4S)-2,2-Dimethyl-1,3-dioxolan-4-yl]methoxy}benzaldehyde

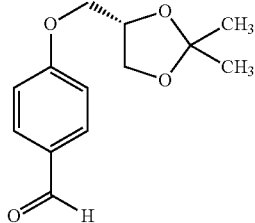 [SMILES: CC1(C)OC[C@H](COc2ccc(C=O)cc2)O1]

The title compound is prepared analogously to Example 8A from the appropriate starting materials.

Yield: 79% of theory

¹H-NMR (400 MHz, DMSO-d₆): δ=9.89 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

LC-MS (method 13): $R_t$=4.02 min; MS (ESIpos): m/z=254 [M+NH₄]⁺.

Example 10A

2-Amino-4-(4-{[(4R)-2,2-dimethyl-1,3-dioxolan-4-yl]methoxy}phenyl)-6-mercaptopyridine-3,5-dicarbonitrile

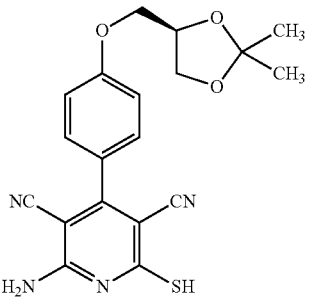 [SMILES: CC1(C)OC[C@@H](COc2ccc(-c3c(C#N)c(N)nc(S)c3C#N)cc2)O1]

40.4 g (171.0 mmol) of the compound from Example 8A and 34.2 g (342.0 mmol) of cyanothioacetamide are initially charged in 700 ml of ethanol. 34.5 g (342.0 mmol) of 4-methylmorpholine are added, and the reaction mixture is, with stirring, heated at reflux for 3 h. After cooling to RT, the mixture is stirred at this temperature for a further 16 h. The resulting precipitate is filtered off with suction, washed with about 100 ml of ethanol and dried in a drying cabinet. The product is used without further purification in the subsequent reactions.

Yield: 19.5 g (29% of theory)

$^1$H-NMR (400 MHz, DMSO-$d_6$): δ=7.63-7.31 (br. s, 2H), 7.41 (d, 2H), 7.09 (d, 2H), 4.49-4.38 (m, 1H), 4.15-3.99 (m, 2H), 3.78 (dd, 1H), 3.66 (dd, 1H), 2.77-2.68 (br. s, 1H), 1.37 (s, 3H), 1.32 (s, 3H).

LC-MS (method 9): $R_t$=1.95 min; MS (ESIpos): m/z=424 [M+H+ CH$_3$CN]$^+$.

Example 11A

2-Amino-4-(4-{[(4S)-2,2-dimethyl-1,3-dioxolan-4-yl]methoxy}phenyl)-6-mercaptopyridine-3,5-dicarbonitrile

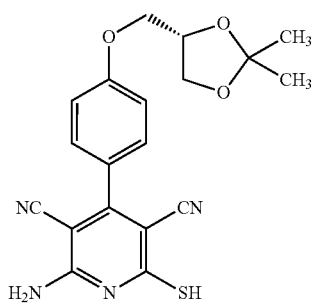 [SMILES: CC1(C)OC[C@H](COc2ccc(-c3c(C#N)c(N)nc(S)c3C#N)cc2)O1]

The title compound is prepared analogously to Example 10A from the compound from Example 9A.

Yield: 32% of theory $^1$H-NMR (400 MHz, DMSO-$d_6$): δ=7.69-7.37 (br. s, 2H), 7.42 (d, 2H), 7.10 (d, 2H), 4.48-4.39 (m, 1H), 4.15-4.02 (m, 2H), 3.78 (dd, 1H), 3.66 (dd, 1H), 2.77-2.68 (br. s, 1H), 1.37 (s, 3H), 1.31 (s, 3H).

LC-MS (method 2): $R_t$=1.75 min; MS (ESIpos): m/z=383 [M+H]$^+$.

Example 12A

3-Fluoro-4-(2-hydroxyethoxy)benzaldehyde

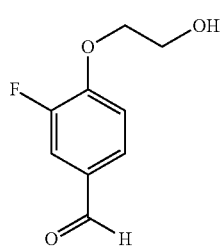 [SMILES: O=Cc1ccc(OCCO)c(F)c1]

5.00 g (35.69 mmol) of 3-fluoro-4-hydroxybenzaldehyde are dissolved in 50 ml of dry DMF. 5.35 g (42.82 mmol) of 2-bromoethanol and 19.73 g (142.74 mmol) of potassium carbonate are added. The reaction mixture is stirred at 150° C. for 10 h. The mixture is then filtered, and the filtrate is freed from the solvent on a rotary evaporator. The residue is taken up in 30 ml of ethyl acetate, and 20 ml of sat. aqueous sodium bicarbonate solution are added. The phases are separated and the organic phase is dried over magnesium sulfate. The solvent is removed on a rotary evaporator. The product obtained is used without further purification in the subsequent reaction.

Yield: 4.45 g (67% of theory)

LC-MS (method 3): $R_t$=1.39 min; MS (ESIpos): m/z=185 [M+H]$^+$.

Example 13A

2-Amino-4-[3-fluoro-4-(2-hydroxyethoxy)phenyl]-6-sulfanylpyridine-3,5-dicarbonitrile

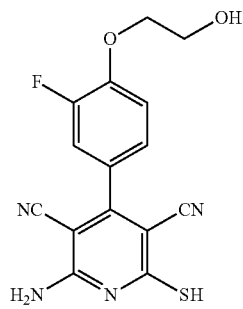

4.45 g (24.16 mmol) of the crude product from Example 12A and 4.84 g (48.33 mmol) of cyanothioacetamide are initially charged in 54 ml of ethanol and 4.89 g (48.33 mmol) of 4-methylmorpholine are added. The reaction mixture is stirred at +80° C. for 4 h. The mixture is then stirred at RT for 8 h. The solvent is removed on a rotary evaporator, and the residue is purified directly by column chromatography on silica gel 60 (mobile phase gradient: dichloromethane/ethanol 15:1→5:1). The product obtained is used without further purification in the subsequent reactions.

Yield: 2.65 g (28% of theory, purity about 90%)

LC-MS (method 3): $R_t$=1.62 min; MS (ESIpos): m/z=331 [M+H]$^+$.

Example 14A 4-(3,3,3-Trifluoro-2-hydroxypropoxy)benzaldehyde

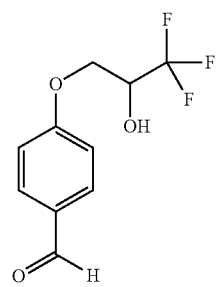 [SMILES: O=Cc1ccc(OCC(O)C(F)(F)F)cc1]

The title compound is prepared analogously to Example 12A from 4-hydroxybenzaldehyde and 3-bromo-1,1,1-trifluoropropan-2-ol.

Yield: 84% of theory

LC-MS (method 6): $R_t$=1.58 min; MS (ESIpos): m/z=235 [M+H]$^+$.

Example 15A

2-Amino-6-sulfanyl-4-[4-(3,3,3-trifluoro-2-hydroxypropoxy)phenyl]pyridine-3,5-dicarbonitrile

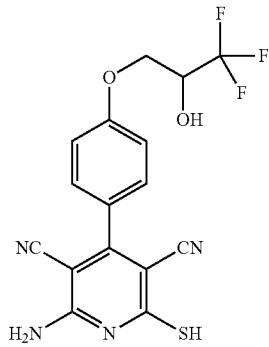 [SMILES: N#Cc1c(N)nc(S)c(C#N)c1-c1ccc(OCC(O)C(F)(F)F)cc1]

The title compound is prepared analogously to Example 10A from the compound from Example 14A. The product obtained is used without further purification in the subsequent reactions.

Yield: 26% of theory (56% purity)

LC-MS (method 3): $R_t$=1.98 min; MS (ESIpos): m/z=381 [M+H]$^+$.

Example 16A 4-(Chloromethyl)-2-(4-fluoro-3-methylphenyl)-1,3-oxazole

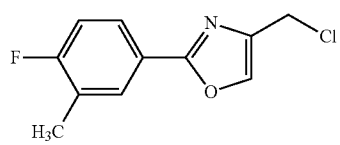

2.00 g (12.80 mmol) of 4-fluoro-3-methylbenzamide and 1.79 g (14.08 mmol) of 1,3-dichloro-acetone are stirred at 130° C. for 2 days. A melt is formed. The mixture is then cooled to RT, 3.0 ml of conc. sulfuric acid are added carefully at this temperature and the mixture is stirred for 15 min. The resulting suspension is poured into 20 ml of ice-water and stirred at RT overnight. The precipitate formed is filtered off and dried at 40° C. in a vacuum drying cabinet overnight.

Yield: 2.05 g (64% of theory, 90% purity)

LC-MS (method 7): $R_t$=2.05 min; MS (ESIpos): m/z=226 [M+H]$^+$.

The compounds listed in Table 1 are prepared analogously to Example 16A from the appropriate starting materials:

TABLE 1

| Example No. | Structure (Yield) | LC-MS: $R_t$ [min] (method); MS (ESI): m/z [M + H]$^+$ | $^1$H-NMR (400 MHz, DMSO-d$_6$): δ = |
|---|---|---|---|
| 17A | ![structure] (49% of theory) | 3.78 min (8); m/z = 228 [M]$^+$ | |
| 18A | ![structure] (58% of theory) | 2.29 min (7); m/z = 262 | |
| 19A | ![structure] (47% of theory) | 2.40 min (9); m/z = 230 | 8.31 (s, 1H), 7.98 (dt, 1H), 7.89-7.82 (m, 1H), 7.64 (q, 1H), 4.76 (s, 2H). |
| 20A | ![structure] (61% of theory) | 2.11 min (12); m/z = 212 | 8.29 (s, 1H), 8.03 (d, 1H), 8.02 (d, 1H), 7.41 (d, 1H), 7.39 (d, 1H), 4.75 (s, 2H). |
| 21A | ![structure] (38% of theory) | 2.41 min (9); m/z = 212 | 8.32 (s, 1H), 7.83 (d, 1H), 7.73 (d, 1H), 7.61 (q, 1H), 7.41 (d, 1H), 4.76 (s, 2H). |

TABLE 1-continued

| Example No. | Structure (Yield) | LC-MS: R$_t$ [min] (method); MS (ESI): m/z [M + H]$^+$ | $^1$H-NMR (400 MHz, DMSO-d$_6$): δ = |
|---|---|---|---|
| 22A | 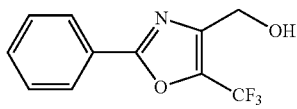 [SMILES: OCc1nc(-c2ccccc2)oc1C(F)(F)F]<br>(84% of theory) | 1.13 min (14); m/z = 194 | |

Example 23A

[2-Phenyl-5-(trifluoromethyl)-1,3-oxazol-4-yl]methanol

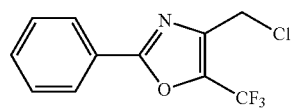

500 mg (1.94 mmol) of 2-phenyl-5-(trifluoromethyl)-1,3-oxazole-4-carboxylic acid are dissolved in 40 ml of dry THF and cooled to −10° C. 197 mg (1.94 mmol) of 4-methylmorpholine and 211 mg (1.94 mmol) of ethyl chloroformate are added. The reaction solution is stirred at −10° C. for 1 h. 3.9 ml (3.89 mmol) of a 1 M solution of lithium aluminum hydride in THF are then slowly added dropwise. The reaction mixture is stirred overnight and slowly allowed to warm to RT. The mixture is then once more cooled to 0° C., and 0.6 ml of water and 1.2 ml of 1 N aqueous sodium hydroxide solution are added carefully. The mixture is then stirred at RT overnight. After filtration, the solvent is removed on a rotary evaporator. The residue is used without further purification in the subsequent reaction.

Yield: 359 mg (58% of theory, 76% purity)

LC-MS (method 8): R$_t$=3.34 min; MS (ESIpos): m/z=244 [M+H]$^+$.

Example 24A 4-(Chloromethyl)-2-phenyl-5-(trifluoromethyl)-1,3-oxazole

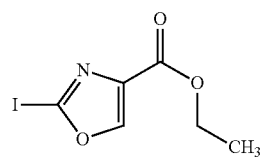

359 mg (1.137 mmol, 76% purity) of the compound from Example 23A are initially charged in 0.63 ml (8.64 mmol) of thionyl chloride. The reaction mixture is stirred at RT for 48 h. After concentration on a rotary evaporator, the residue is taken up in 10 ml of ethyl acetate and washed once with 5 ml of sat. aqueous sodium bicarbonate solution. The organic phase is dried over magnesium sulfate. After filtration, the solvent is removed on a rotary evaporator. The residue is purified by column chromatography on silica gel 60 (mobile phase gradient: cyclohexane/ethyl acetate 400:1→60:1). This gives a light-brown solid.

Yield: 148 mg (50% of theory)

LC-MS (method 7): R$_t$=2.34 min; MS (ESIpos): m/z=262 [M+H]$^+$.

Example 25A

Ethyl 2-iodo-1,3-oxazole-4-carboxylate

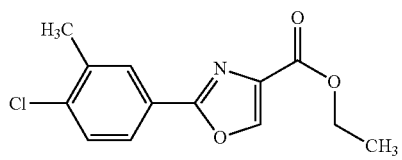 [SMILES: CCOC(=O)c1coc(-c2ccc(Cl)c(C)c2)n1]

2.00 g (12.81 mmol) of ethyl 2-amino-1,3-oxazole-4-carboxylate are added to a solution of 8.00 g (38.43 mmol) of p-toluenesulfonic acid dihydrate in 48 ml of acetonitrile. The suspension is cooled to 0° C., and a solution of 1.77 g (25.62 mmol) sodium nitrite and 5.32 g (32.02 mmol) potassium iodide in 7.2 ml of water is then added. The mixture is stirred at 0° C. for 10 min and, after warming to RT, further overnight. The mixture is then diluted with 200 ml of water. By addition of 1 M aqueous sodium bicarbonate solution, the pH is adjusted to 9. 24 ml of 2 M sodium thiosulfate solution are then added. The aqueous phase is extracted three times with in each case 30 ml of ethyl acetate. The combined organic phases are dried over magnesium sulfate. After filtration, the solvent is removed on a rotary evaporator. The residue is purified by column chromatography on silica gel 60 (mobile phase gradient: cyclohexane/ethyl acetate 300:1→2:1).

Yield: 0.97 g (28% of theory)

LC-MS (method 6): R$_t$=1.41 min; MS (ESIpos): m/z=268 [M+H]$^+$.

Example 26A

Ethyl 2-(4-chloro-3-methylphenyl)-1,3-oxazole-4-carboxylate 385 mg (1.44 mmol) of the compound from Example 25A and 319 mg (1.87 mmol) of 4-chloro-3-methylphenylboronic acid are initially charged in 12.7 ml of dry N-methyl-2-pyrrolidone. 105 mg (0.14 mmol) of bis(diphenylphosphino)ferrocenepalladium(II) chloride, 0.33 ml water and 940 mg (2.88 mmol) of cesium carbonate are then added. The reaction mixture is stirred at 50° C. for 4 h. The mixture is then cooled to RT, and 20 ml of ethyl acetate and 10 ml of water are added. The aqueous phase is extracted twice with in each case 20 ml of ethyl acetate. The combined organic phases are washed once with 10 ml of sat. aqueous sodium chloride solution and

Example 27A

[2-(4-Chloro-3-methylphenyl)-1,3-oxazol-4-yl]methanol

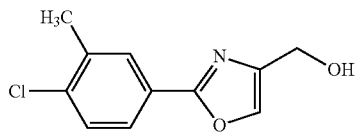

46 mg (1.22 mmol) of lithium aluminum hydride are initially charged in 8.0 ml of THF and cooled to 0° C. A solution of 161 mg (0.61 mmol) of the compound from Example 26A in 2.5 ml of THF is then added dropwise. The mixture is stirred at RT for 2 h. The reaction solution is then once more cooled to 0° C., and 0.2 ml of water and 0.4 ml of 1 N aqueous sodium hydroxide solution are added. The mixture is stirred at RT overnight. The precipitate formed is filtered off, and the filtrate is freed from the solvent using a rotary evaporator. The residue is used without further purification in the subsequent reaction.

Yield: 137 mg (70% of theory, 70% purity)

LC-MS (method 3): $R_t$=2.14 min; MS (ESIpos): m/z=224 [M+H]$^+$.

Example 28A 4-(Chloromethyl)-2-(4-chloro-3-methylphenyl)-1,3-oxazole

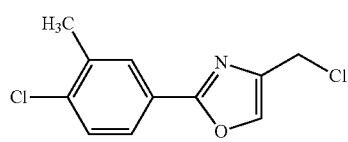

136 mg (0.61 mmol) of the compound from Example 27A are suspended in 2 ml of dichloromethane. The suspension is cooled to 0° C., and 49 µl (0.67 mmol) of thionyl chloride are added slowly. The reaction solution is stirred at RT overnight. The solvent is then removed on a rotary evaporator. The residue is used without further purification in the subsequent reactions.

Yield: 178 mg (42% of theory, 35% purity)

LC-MS (method 7): $R_t$=2.56 min; MS (ESIpos): m/z=242 [M+H]$^+$.

dried over magnesium sulfate. After filtration, the solvent is removed on a rotary evaporator. The residue is purified by preparative HPLC (column: YMC GEL ODS-AQ S-5/15 µm; mobile phase gradient: acetonitrile/water 10:90→95:5).

Yield: 162 mg (42% of theory)

LC-MS (method 7): $R_t$=2.19 min; MS (ESIpos): m/z=266 [M+H]$^+$.

Example 29A 2-(4-Chlorophenyl)-5-ethyl-4-methyl-1,3-oxazole 3-oxide

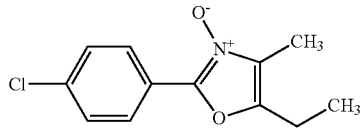 [SMILES: CCc1oc(-c2ccc(Cl)cc2)[n+]([O-])c1C]

1.00 g (8.69 mmol) of 2,3-pentanedione 2-oxime and 1.34 g (9.55 mmol) of 4-chlorobenzaldehyde are initially charged in 2 ml (34.94 mmol) of glacial acetic acid. With ice-cooling of the reaction mixture, hydrogen chloride gas is then introduced for 30 min. 10 ml of diethyl ether are then added to the reaction mixture. A precipitate is formed, which is filtered off with suction and washed twice with in each case 2 ml of diethyl ether. The precipitate is resuspended in about 5 ml of water, and the suspension is made basic using ammonia. The suspension is then extracted four times with in each case 10 ml of dichloromethane. The combined organic phases are dried over magnesium sulfate and the solvent is removed on a rotary evaporator. The residue is used without further purification in the subsequent reaction.

Yield: 1.6 g (76% of theory)

$^1$H-NMR (400 MHz, DMSO-d$_6$): δ=8.42 (d, 2H), 7.63 (d, 2H), 2.76 (q, 2H), 2.10 (s, 3H), 1.24 (t, 3H).

LC-MS (method 6): $R_t$=1.67 min; MS (ESIpos): m/z=238 [M+H]$^+$.

Example 30A 4-(Chloromethyl)-2-(4-chlorophenyl)-5-ethyl-1,3-oxazole

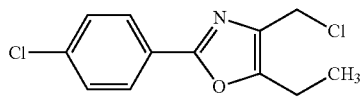

1.00 g (4.21 mmol) of the compound from Example 29A are dissolved in 15 ml of chloroform, and 1.4 ml (15.15 mmol) of phosphoryl chloride are added carefully. The mixture is heated to reflux and stirred at this temperature for 30 min. The mixture is then cooled to 0° C. and made slightly basic using ammonia. The reaction mixture is extracted three times with in each case 20 ml of ethyl acetate. The solvent is removed on a rotary evaporator and the residue is dried in a vacuum drying cabinet. The product is used without further purification in the subsequent reactions.

Yield: 1.2 g (84% of theory, 74% purity)

$^1$H-NMR (400 MHz, DMSO-d$_6$): δ=7.96 (d, 2H), 7.60 (d, 2H), 4.77 (s, 2H), 2.85 (q, 2H), 1.23 (t, 3H).

LC-MS (method 6): $R_t$=2.56 min; MS (ESIpos): m/z=256 [M+H]$^+$.

Example 31A 2-(4-Chlorophenyl)-4,5-dimethyl-1,3-oxazole 3-oxide

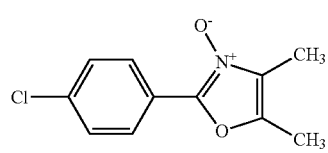

1.00 g (9.89 mmol) of diacetyl monooxime and 1.53 g (10.88 mmol) of 4-chlorobenzaldehyde are initially charged in 2 ml (34.94 mmol) of glacial acetic acid. With ice-cooling of the reaction mixture, hydrogen chloride gas is then introduced for 30 min. 10 ml of diethyl ether are then added to the reaction mixture. A precipitate is formed, which is filtered off with suction and washed twice with in each case 2 ml of diethyl ether. The precipitate is resuspended in about 5 ml of water, and the suspension is made basic using ammonia. The suspension is then extracted four times with in each case 10 ml of dichloromethane. The combined organic phases are dried over magnesium sulfate and the solvent is removed on a rotary evaporator. The residue is used without further purification in the subsequent reaction.

Yield: 1.85 g (84% of theory)

LC-MS (method 5): $R_t$=2.29 min; MS (ESIpos): m/z=224 [M+H]$^+$.

The compounds listed in Table 2 are prepared analogously to Example 31A from the appropriate starting materials:

TABLE 2

| Example No. | Structure (Yield) | LC-MS: $R_t$ [min] (method); MS (ESI): m/z [M + H]$^+$ |
|---|---|---|
| 32A | ![structure] (82% of theory) | 1.99 min (3); m/z = 242 |
| 33A | ![structure] (75% of theory) | 1.82 min (15); m/z = 258 |

Example 34A 4-(Chloromethyl)-2-(4-chlorophenyl)-5-methyl-1,3-oxazole

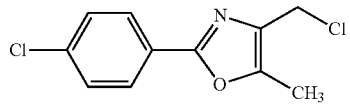

1.00 g (4.47 mmol) of the compound from Example 31A are initially charged in 15 ml of chloroform, and 1.5 ml (16.10 mmol) of phosphoryl chloride are added carefully. With stirring, the reaction mixture is heated at reflux for 30 min. The mixture is then cooled to 0° C. and made weakly basic by addition of ammonia. The mixture is extracted three times with in each case 20 ml of ethyl acetate. The combined organic phases are washed twice with in each case 5 ml of water and then dried over magnesium sulfate. The solvent is removed on a rotary evaporator. The residue is used without further purification in the subsequent steps.

Yield: 1.33 g (96% of theory, 78% purity)

$^1$H-NMR (400 MHz, DMSO-d$_6$): δ=7.95 (d, 2H), 7.60 (d, 2H), 4.77 (s, 2H), 2.44 (s, 3H).

LC-MS (method 3): $R_t$=2.80 min; MS (ESIpos): m/z=242 [M+H]$^+$.

The examples listed in Table 3 are prepared analogously to Example 34A from the appropriate starting materials:

TABLE 3

| Example No. | Structure (Yield) | LC-MS: $R_t$ [min] (method); MS (ESI): m/z [M + H]$^+$ |
|---|---|---|
| 35A | ![structure] (83% of theory) | 2.27 min (7); m/z = 260 |
| 36A | ![structure] (84% of theory) | 1.37 min (14); m/z = 276 |

Example 37A

Methyl 5-(4-chlorophenyl)-1,3-oxazole-4-carboxylate

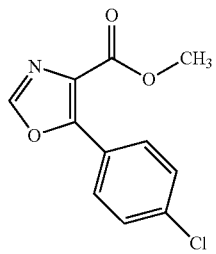 [SMILES: COC(=O)c1ncoc1-c1ccc(Cl)cc1]

1.40 g (8.00 mmol) of 4-chlorobenzoyl chloride, 1.00 g (10.09 mmol) of methyl isocyanatoacetate and 5.9 ml (42.39 mmol) of triethylamine are dissolved in 15 ml of dry THF and stirred at RT for 48 h. The solvent is then removed on a rotary evaporator. The residue is taken up in 20 ml of ethyl acetate and washed once with 5 ml of water. The organic phase is dried over magnesium sulfate and the solvent is removed on a rotary evaporator. The residue is suspended in 10 ml of cyclohexane and filtered off. It is then recrystallized from about 10 ml of methanol. This gives needle-shaped crystals which are dried in a drying cabinet at 50° C. A further product fraction is obtained by reprecipitation after recrystallization.

Yield: 0.85 g (45% of theory)

$^1$H-NMR (400 MHz, DMSO-d$_6$): δ=8.61 (s, 1H), 8.02 (d, 2H), 7.62 (d, 2H), 3.82 (s, 3H).

LC-MS (method 14): R$_t$=1.09 min; MS (ESIpos): m/z=238 [M+H]$^+$.

Example 38A

[5-(4-Chlorophenyl)-1,3-oxazol-4-yl]methanol

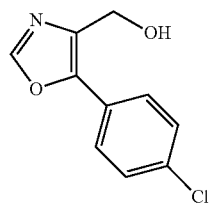 [SMILES: OCc1ncoc1-c1ccc(Cl)cc1]

166 mg (4.38 mmol) of lithium aluminum hydride are initially charged in 10 ml of dry THF and cooled to 0° C. A solution of 260 mg (1.09 mmol) of the compound from Example 37A in 10 ml of dry THF is added dropwise. After the addition has ended, the reaction solution is slowly warmed to RT and stirred at this temperature for 1 h. With stirring, the mixture is then heated at reflux for 2 h. The mixture is then cooled again to 0° C., 0.4 ml of water and 0.8 ml of 1 N aqueous sodium hydroxide solution are added carefully and the mixture is stirred at RT for 3 h. The precipitate formed is filtered off, and the filtrate is freed from the solvent on a rotary evaporator. The residue is used without further purification in the subsequent reaction.

Yield: 219 mg (82% of theory, 86% purity)

LC-MS (method 15): R$_t$=1.74 min; MS (ESIpos): m/z=210 [M+H]$^+$.

Example 39A 4-(Chloromethyl)-5-(4-chlorophenyl)-1,3-oxazole

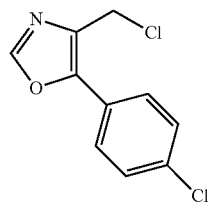 [SMILES: ClCc1ncoc1-c1ccc(Cl)cc1]

269 mg (0.77 mmol) of the compound from Example 38A are initially charged in 0.43 ml (5.85 mmol) of thionyl chloride. The reaction mixture is stirred at RT for 12 h, and excess thionyl chloride is then removed under reduced pressure. The residue is taken up in 5 ml of ethyl acetate and washed once with 2 ml of sat. aqueous sodium bicarbonate solution. The organic phase is dried over magnesium sulfate and the solvent is removed on a rotary evaporator. The product obtained is used without further purification in the subsequent reactions.

Yield: 145 mg (62% of theory, 76% purity)

LC-MS (method 14): R$_t$=1.21 min; MS (ESIpos): m/z=228 [M+H]$^+$.

Example 40A 2-(4-Chlorophenyl)-4-[(methoxymethoxy)methyl]-1,3-oxazole

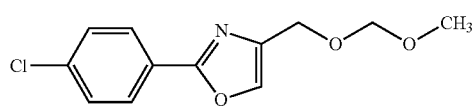 [SMILES: COCOCc1coc(-c2ccc(Cl)cc2)n1]

1.32 g (7.54 mmol) of [2-(4-chlorophenyl)-1,3-oxazol-4-yl]methanol (Example 100A) are initially charged in 18.5 ml of dry THF and cooled to 0° C., and 0.33 g (8.29 mmol) sodium hydride (60% strength in mineral oil) are added. The mixture is stirred at 0° C. for 10 min and then at RT for 1 h. The reaction mixture is again cooled to 0° C., and 0.69 ml (9.04 mmol) of chlorodimethyl ether is added. The mixture is stirred at 0° C. for 10 min and then at RT for 2 h. 5 ml of water are then added, and the reaction mixture is extracted three times with in each case 25 ml of ethyl acetate. The combined organic phases are dried over magnesium sulfate and the solvent is removed on a rotary evaporator. The product obtained is used without further purification in the subsequent reaction.

Yield: 1.70 g (87% of theory, 85% purity)

LC-MS (method 7): R$_t$=1.58 min; MS (ESIpos): m/z=220 [M+H]$^+$.

Example 41A 2-(4-Chlorophenyl)-4-[(methoxymethoxy)methyl]-1,3-oxazole-5-carbaldehyde

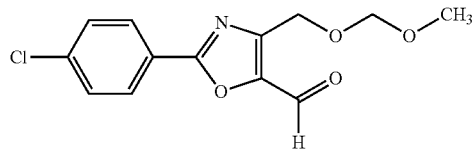

200 mg (0.91 mmol) of the crude product from Example 40A are initially charged in 3.5 ml of dry diethyl ether and cooled to −78° C. 0.63 ml (1.00 mmol) of a 1.6 M solution of n-butyllithium in hexane are slowly added dropwise. The reaction mixture is stirred at −78° C. for 1 h. 0.21 ml (2.74 mmol) of N,N-dimethylformamide is then slowly added dropwise. The mixture is allowed to warm to RT and stirred at RT for another 1 h. The mixture is then poured into about 3 ml of water. The mixture is extracted three times with in each case 10 ml of diethyl ether. The combined organic phases are dried over magnesium sulfate and the solvent is removed on a rotary evaporator. The residue is purified by column chromatography on silica gel 60 (mobile phase gradient: cyclohexane/ethyl acetate 20:1→2:1).

Yield: 161 mg (56% of theory, 79% purity)

LC-MS (method 6): $R_t$=1.74 min; MS (ESIpos): m/z=248 [M+H]$^+$.

Example 42A 2-(4-Chlorophenyl)-4-[(methoxymethoxy)methyl]-1,3-oxazole-5-carboxylic acid

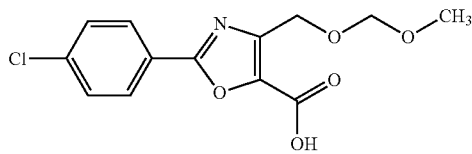 [SMILES: COCOCc1nc(-c2ccc(Cl)cc2)oc1C(=O)O]

556 mg (2.25 mmol) of the compound from Example 41A and 14.7 ml of dioxane are added to a suspension of 802 mg (4.72 mmol) of silver(I) nitrate in 2 ml of water. A solution of 193 mg (4.84 mmol) of sodium hydroxide in 7.8 ml of water is then added slowly. The mixture is stirred at RT for 3 h. The mixture is then filtered through Celite, which is washed with warm water. The filtrate obtained is acidified by addition of 1 N hydrochloric acid and extracted three times with in each case 20 ml of diethyl ether. The combined organic phases are dried over magnesium sulfate and the solvent is removed on a rotary evaporator. The residue is purified by preparative HPLC (column: YMC GEL ODS-AQ S-5/15 µm; mobile phase gradient: acetonitrile/water 10:90→95:5).

Yield: 138 mg (21% of theory, 92% purity)

LC-MS (method 3): $R_t$=1.93 min; MS (ESIpos): m/z=286 [M+Na]$^+$.

Example 43A

Methyl 2-(4-chlorophenyl)-4-[(methoxymethoxy)methyl]-1,3-oxazole-5-carboxylate

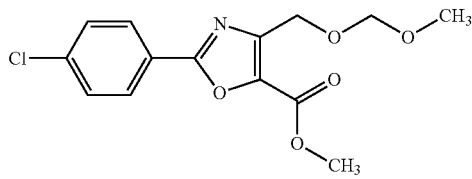 [SMILES: COCOCc1nc(-c2ccc(Cl)cc2)oc1C(=O)OC]

138 mg (0.52 mmol) of the compound from Example 42A are dissolved in 3 ml toluene and 2.5 ml of methanol. 0.4 ml (0.79 mmol) of a 2 M solution of trimethylsilyldiazomethane in hexane is then added dropwise. The mixture is stirred at RT for 10 min and the solvent is then removed on a rotary evaporator. The residue is used without further purification in the subsequent reaction.

Yield: 144 mg (90% of theory, 91% purity)

LC-MS (method 15): $R_t$=1.98 min; MS (ESIpos): m/z=300 [M+Na]$^+$.

Example 44A

Methyl 2-(4-chlorophenyl)-4-(hydroxymethyl)-1,3-oxazole-5-carboxylate

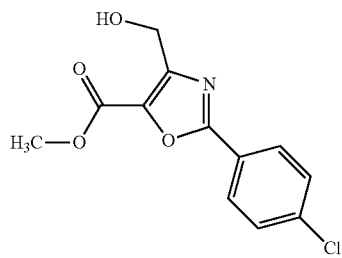 [SMILES: COC(=O)c1oc(-c2ccc(Cl)cc2)nc1CO]

144 mg (0.52 mmol) of the compound from Example 43A are initially charged in 0.5 ml of methanol, and 0.13 ml of 4 N hydrochloric acid are added. 3 drops of conc. hydrochloric acid are then added. The reaction mixture is stirred at RT for 8 h. The mixture is then diluted with about 5 ml of water and extracted three times with in each case 10 ml of diethyl ether. The combined organic phases are dried over magnesium sulfate and the solvent is removed on a rotary evaporator. The product obtained is used without further purification in the subsequent reaction.

Yield: 100 mg (81% of theory, 84% purity)

LC-MS (method 7): $R_t$=1.29 min; MS (ESIpos): m/z=234 [M+H]$^+$.

Example 45A

Methyl 4-(chloromethyl)-2-(4-chlorophenyl)-1,3-oxazole-5-carboxylate

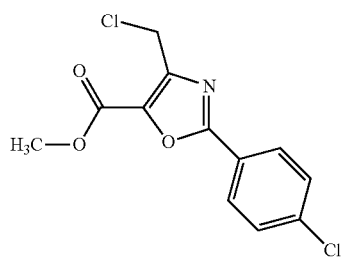 [SMILES: COC(=O)c1oc(-c2ccc(Cl)cc2)nc1CCl]

100 mg (0.43 mmol) of the compound from Example 44A, together with 0.24 ml (3.24 mmol) of thionyl chloride, are stirred at RT for 8 h. The excess thionyl chloride is removed under reduced pressure and the residue is taken up in about 5 ml of ethyl acetate. The mixture is washed once with 2 ml of sat. aqueous sodium bicarbonate solution. The organic phase is dried over magnesium sulfate and the solvent is removed under reduced pressure. The product obtained is used without further purification in the subsequent reactions.

Yield: 99 mg (92% of theory, 98% purity)

LC-MS (method 7): $R_t$=1.96 min; MS (ESIpos): m/z=252 [M+H]$^+$.

Example 46A

2-Amino-6-({[2-(4-chlorophenyl)-1,3-oxazol-4-yl]methyl}sulfanyl)-4-(4-{[(4R)-2,2-dimethyl-1,3-dioxolan-4-yl]methoxy}-phenyl)pyridine-3,5-dicarbonitrile

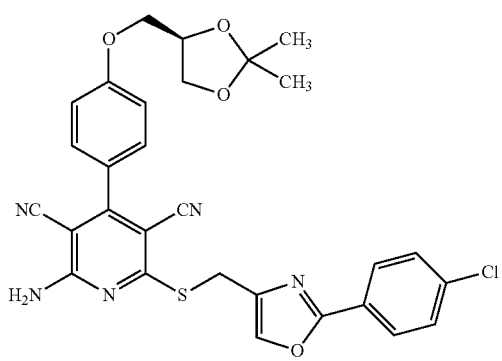 [SMILES: CC1(C)OC[C@@H](COc2ccc(-c3c(C#N)c(N)nc(SCc4coc(-c5ccc(Cl)cc5)n4)c3C#N)cc2)O1]

70 mg (0.18 mmol) of the compound from Example 10A and 46 mg (0.20 mmol) of the compound from Example 17A, together with 46 mg (0.55 mmol) of sodium bicarbonate, are suspended in 1.9 ml of dry DMF. The reaction mixture is stirred at RT for 20 h. On a rotary evaporator, the mixture is then freed from the solvent, and the residue is purified by preparative HPLC (column: YMC GEL ODS-AQ S-5/15 μm; mobile phase gradient: acetonitrile/water 10:90→95:5).

Yield: 79 mg (75% of theory)

$^1$H-NMR (400 MHz, DMSO-$d_6$): δ=8.37 (s, 1H), 8.30-8.01 (br. s, 2H), 7.97 (d, 2H), 7.60 (d, 2H), 7.48 (d, 2H), 7.12 (d, 2H), 4.48-4.40 (m, 1H), 4.42 (s, 2H), 4.16-4.03 (m, 3H), 3.78 (dd, 1H), 1.37 (s, 3H), 1.31 (s, 3H).

LC-MS (method 3): $R_t$=2.99 min; MS (ESIpos): m/z=574 [M+H]$^+$.

Example 47A

2-Amino-6-({[2-(4-chlorophenyl)-1,3-oxazol-4-yl]methyl}sulfanyl)-4-(4-{[(4S)-2,2-dimethyl-1,3-dioxolan-4-yl]methoxy}phenyl)pyridine-3,5-dicarbonitrile 150 mg (0.39 mmol) of the compound from Example 11A and 98 mg (0.43 mmol) of the compound from Example 17A, together with 99 mg (1.18 mmol) of sodium bicarbonate, are suspended in 2 ml of dry DMF. The reaction mixture is stirred at RT for 20 h. The mixture is then purified directly by preparative HPLC (column: YMC GEL ODS-AQ S-5/15 μm; mobile phase gradient: acetonitrile/water 10:90→95:5).

Yield: 147 mg (65% of theory)

$^1$H-NMR (400 MHz, DMSO-$d_6$): δ=8.37 (s, 1H), 8.29-7.91 (br. s, 2H), 7.97 (d, 2H), 7.61 (d, 2H), 7.47 (d, 2H), 7.12 (d, 2H), 4.48-4.39 (m, 1H), 4.42 (s, 2H), 4.16-4.03 (m, 3H), 3.77 (dd, 1H), 1.37 (s, 3H), 1.31 (s, 3H).

LC-MS (method 4): $R_t$=4.23 min; MS (ESIpos): m/z=574 [M+H]$^+$.

The examples listed in Table 4 are prepared analogously to Examples 46A and 47A from the appropriate starting materials:

TABLE 4

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 48A | (67% of theory) | 2.98 min (3); m/z = 572 | |

TABLE 4-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 49A | 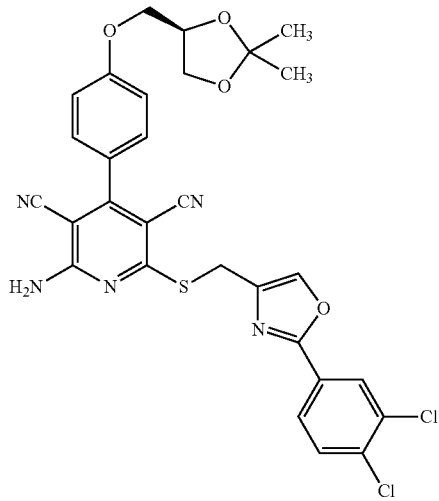<br>(77% of theory) | 2.80 min (6); m/z = 608 | 8.41 (s, 1H), 8.36-7.98 (br. s, 2H), 8.12 (d, 1H), 7.92 (dd, 1H), 7.71 (d, 1H), 7.48 (d, 2H), 7.11 (d, 2H), 4.48-4.39 (m, 1H), 4.42 (s, 2H), 4.15-4.03 (m, 3H), 3.79 (dd, 1H), 1.38 (s, 3H), 1.31 (s, 3H). |
| 50A | 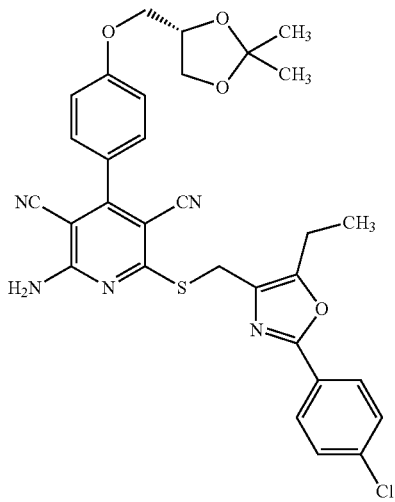<br>(36% of theory) | 2.63 min (7); m/z = 602 | 8.21-7.89 (br. s, 2H), 7.93 (d, 2H), 7.59 (d, 2H), 7.50 (d, 2H), 7.12 (d, 2H), 4.52 (s, 2H), 4.47-4.40 (m, 1H) 4.15-4.03 (m, 3H), 3.78 (dd, 1H), 2.89 (q, 2H), 1.37 (s, 3H), 1.32 (s, 3H), 1.20 (t, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 51A | 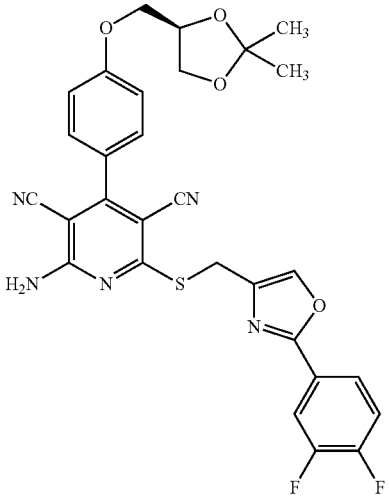 (92% of theory) | 2.38 min (7); m/z = 576 | |
| 52A | 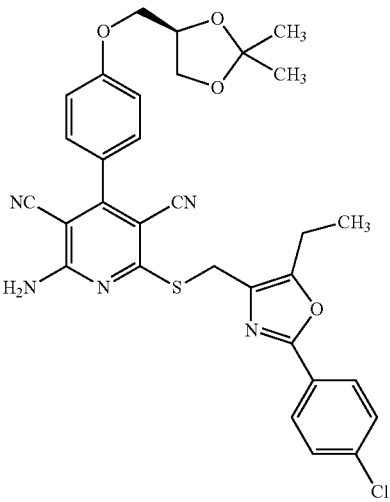 (54% of theory) | 3.22 min (3); m/z = 602 | 8.21-7.88 (br. s, 2H), 7.94 (d, 2H), 7.59 (d, 2H), 7.49 (d, 2H), 7.22 (d, 2H), 4.51 (s, 2H), 4.48-4.39 (m, 1H), 4.18-4.04 (m, 3H), 3.79 (t, 1H), 2.88 (q, 2H), 1.38 (s, 3H), 1.32 (s, 3H), 1.21 (t, 3H). |

TABLE 4-continued
| Example No. | Structure (Yield) | LC-MS: $R_t$ [min] (method); MS (ESI): m/z [M + H]+ | 1H-NMR (DMSO-d6): δ = |
|---|---|---|---|
| 53A | 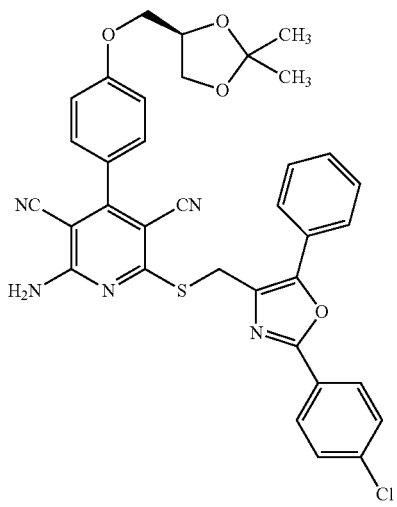 (80% of theory) | 3.40 min (3); m/z = 650 | 8.15-8.07 (m, 2H), 7.96-7.88 (m, 2H), 7.84 (d, 2H), 7.68-7.61 (m, 2H), 7.61-7.53 (m, 2H), 7.52-7.44 (m, 3H), 7.12 (d, 2H), 4.81 (s, 2H), 4.48-4.41 (m, 1H), 4.16-4.03 (m, 3H), 3.79 (dd, 1H), 1.38 (s, 3H), 1.32 (s, 3H). |
| 54A | 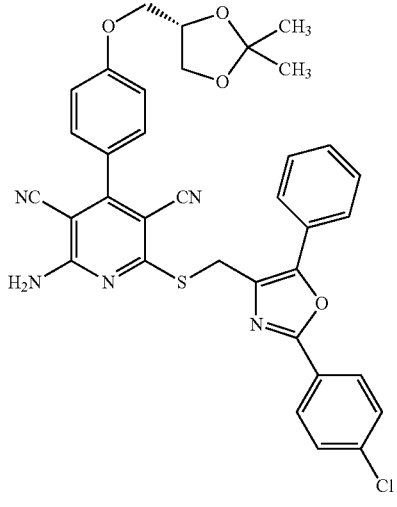 (76% of theory) | 3.40 min (3); m/z = 650 | |

TABLE 4-continued

| Example No. | Structure (Yield) | LC-MS: R_t [min] (method); MS (ESI): m/z [M + H]+ | 1H-NMR (DMSO-d6): δ = |
|---|---|---|---|
| 55A | (59% of theory) | 3.96 min (5); m/z = 612 | 8.33-8.18 (m, 6H), 7.66 (d, 2H), 7.30 (d, 2H), 4.71 (s, 2H), 4.67-4.58 (m, 1H), 4.36-4.22 (m, 3H), 4.08 (s, 3H), 4.00-3.92 (m, 1H), 2.68 (s, 3H), 1.57 (s, 3H), 1.50 (s, 3H). |
| 56A | (42% of theory) | 2.54 min (7); m/z = 588 | |

| Example No. | Structure (Yield) | LC-MS: $R_t$ [min] (method); MS (ESI): m/z [M + H]+ | $^1$H-NMR (DMSO-$d_6$): δ = |
|---|---|---|---|
| 57A | 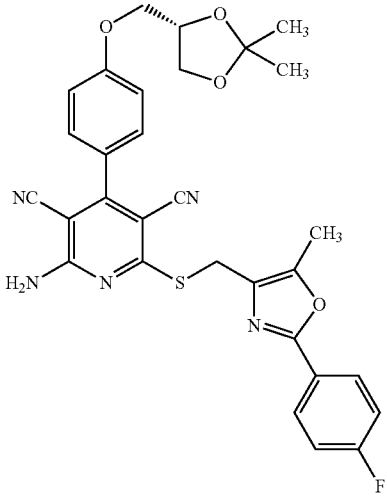<br>(77% of theory) | 2.58 min (6); m/z = 572 | 8.14-7.92 (br. s, 2H), 7.96 (d, 1H), 7.95 (d, 1H), 7.49 (d, 2H), 7.36 (t, 2H), 7.12 (d, 2H), 4.51 (s, 2H), 4.47-4.41 (m, 1H), 4.14-4.03 (m, 1H), 3.79 (dd, 1H), 2.47 (s, 3H), 1.38 (s, 3H), 1.32 (s, 3H). |
| 58A | 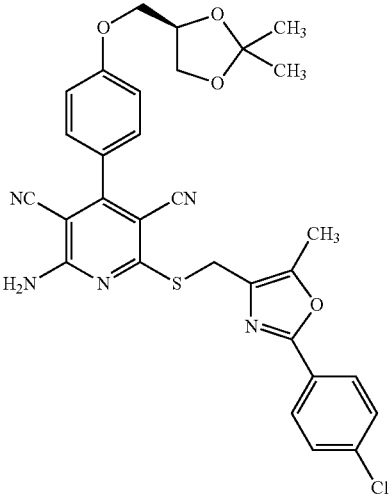<br>(60% of theory) | 2.54 min (7); m/z = 588 | 8.19-7.97 (br. s, 2H), 7.94 (d, 2H), 7.58 (d, 2H), 7.49 (d, 2H), 7.12 (d, 2H), 4.51 (s, 2H), 4.48-4.41 (m, 1H), 4.16-4.03 (m, 3H), 3.79 (dd, 2H), 2.46 (s, 3H), 1.37 (s, 3H), 1.32 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 59A | 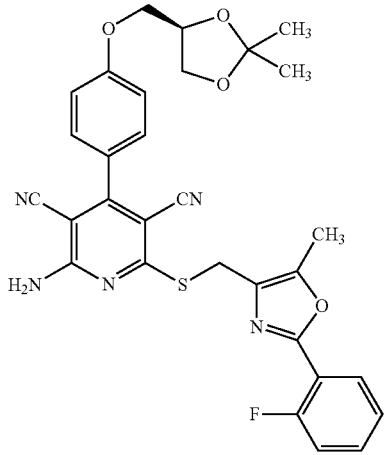<br>(76% of theory) | 2.34 min (7); m/z = 572 | 8.19-7.95 (br. s, 2H), 7.96 (dt, 1H), 7.60-7.52 (m, 1H), 7.49 (d, 2H), 7.42-7.32 (m, 2H), 7.12 (d, 2H), 4.53 (s, 2H), 4.48-4.41 (m, 1H), 4.17-4.04 (m, 3H), 3.78 (dd, 1H), 2.48 (s, 3H), 1.38 (s, 3H), 1.31 (s, 3H). |
| 60A | 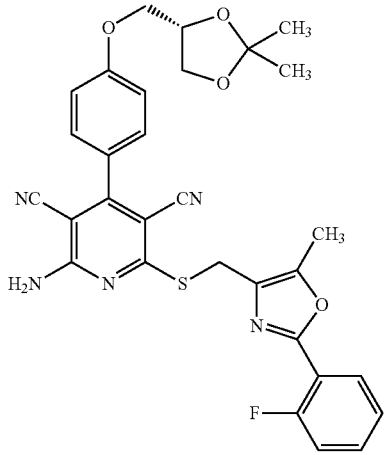<br>(72% of theory) | 2.34 min (7); m/z = 572 | 8.21-7.96 (br. s, 2H), 7.96 (dt, 1H), 7.60-7.53 (m, 1H), 7.49 (d, 2H), 7.42-7.32 (m, 2H), 7.12 (d, 2H), 4.53 (s, 2H), 4.47-4.41 (m, 1H), 4.16-4.04 (m, 3H), 3.79 (dd, 1H), 2.48 (s, 3H), 1.38 (s, 3H), 1.31 (s, 3H). |
| 61A | 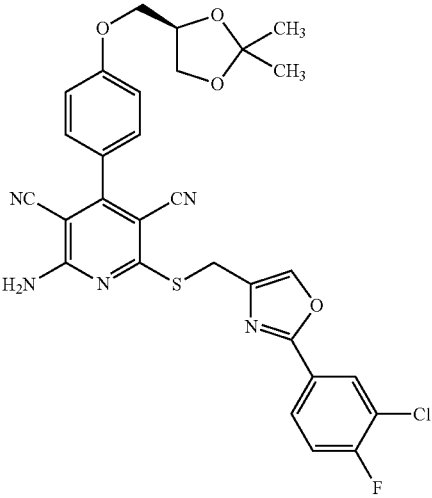<br>(82% of theory) | 2.48 min (7); m/z = 592 | 8.49 (s, 1H), 8.26-7.92 (br. s, 2H), 8.10 (dd, 1H), 8.00-7.94 (m, 1H), 7.60 (pseudo-t, 1H), 7.47 (d, 2H), 7.11 (d, 2H), 4.48-4.39 (m, 1H), 4.42 (s, 2H), 4.15-4.03 (m, 3H), 3.78 (dd, 1H), 1.38 (s, 3H), 1.32 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 62A | 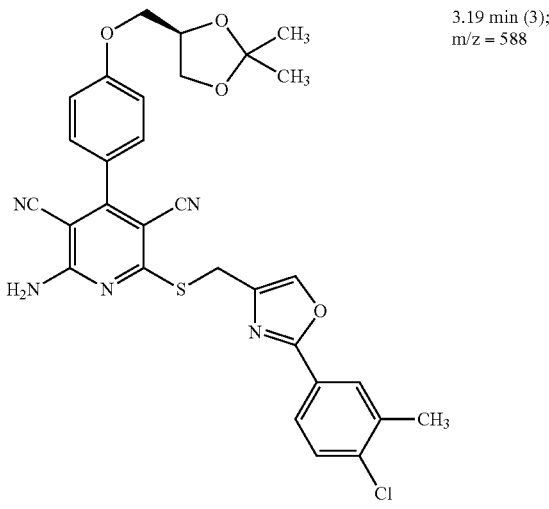 (12% of theory) | 3.19 min (3); m/z = 588 | |
| 63A | 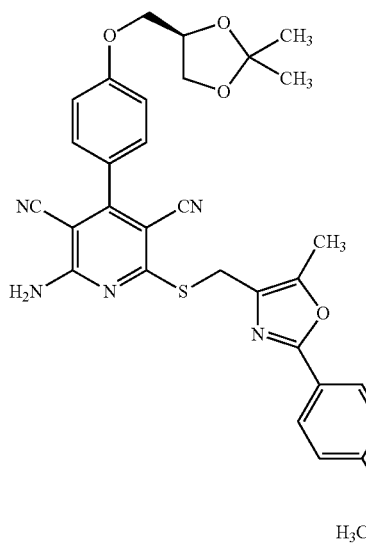 (45% of theory) | 2.35 min (7); m/z = 584 | 8.19-7.95 (br. s, 2H), 7.86 (d, 2H), 7.49 (d, 2H), 7.13 (d, 2H), 7.06 (d, 2H), 4.48 (s, 2H), 4.47-4.41 (m, 1H), 4.16-4.03 (m, 3H), 3.81 (s, 3H), 3.81-3.75 (m, 1H), 2.43 (s, 3H), 1.38 (s, 3H), 1.31 (s, 3H). |

| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 64A | 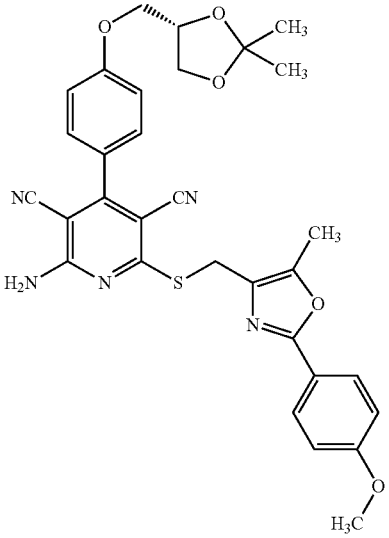 (44% of theory) | 2.94 min (3); m/z = 584 | 8.19-7.93 (br. s, 2H), 7.85 (d, 2H), 7.49 (d, 2H), 7.13 (d, 2H), 7.07 (d, 2H), 4.49 (s, 2H), 4.47-4.41 (m, 1H), 4.16-4.03 (m, 3H), 3.81 (s, 3H), 3.81-3.74 (m, 1H), 2.45 (s, 3H), 1.38 (s, 3H), 1.31 (s, 3H). |
| 65A | 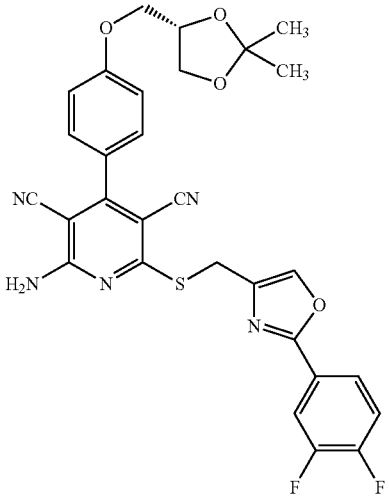 (94% of theory) | 2.99 min (3); m/z = 576 | |

TABLE 4-continued
| Example No. | Structure (Yield) | LC-MS: R_t [min] (method); MS (ESI): m/z [M + H]+ | 1H-NMR (DMSO-d_6): δ = |
|---|---|---|---|
| 66A | 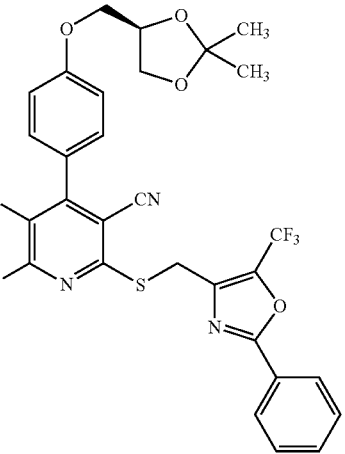 (56% of theory) | 3.15 min (3); m/z = 608 | 8.06-7.93 (br. s, 2H), 8.05 (d, 2H), 7.68-7.57 (m, 3H), 7.51 (d, 2H), 7.14 (d, 2H), 4.71 (s, 2H), 4.48-4.41 (m, 1H), 4.18-4.04 (m, 3H), 3.79 (dd, 1H), 1.37 (s, 3H), 1.31 (s, 3H). |
| 67A | 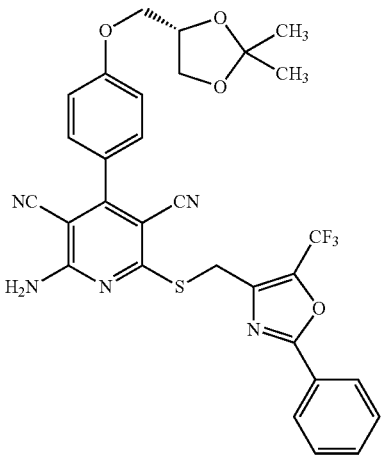 (61% of theory) | 3.15 min (3); m/z = 608 | 8.07-7.95 (br. s, 2H), 8.05 (d, 2H), 7.68-7.57 (m, 3H), 7.51 (d, 2H), 7.14 (d, 2H), 4.71 (s, 2H), 4.48-4.41 (m, 1H), 4.17-4.05 (m, 3H), 3.79 (dd, 1H), 1.37 (s, 3H), 1.32 (s, 3H). |
| 68A | 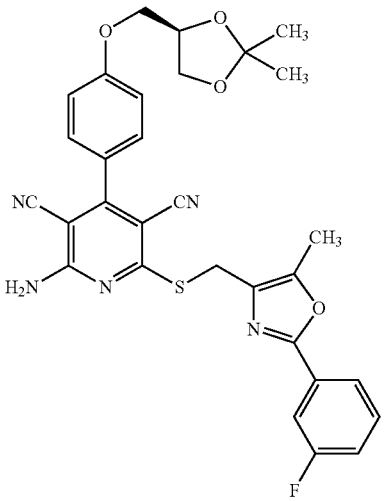 (74% of theory) | 3.01 min (3); m/z = 572 | 8.17-7.96 (br. s, 2H), 7.77 (d, 1H), 7.66 (d, 1H), 7.57 (q, 1H), 7.49 (d, 2H), 7.36 (dt, 1H), 7.12 (d, 2H), 4.52 (s, 2H), 4.48-4.41 (m, 1H), 4.15-4.03 (m, 3H), 3.78 (dd, 1H), 2.47 (s, 3H), 1.37 (s, 3H), 1.31 (s, 3H). |

TABLE 4-continued
| Example No. | Structure (Yield) | LC-MS: $R_t$ [min] (method); MS (ESI): m/z [M + H]⁺ | ¹H-NMR (DMSO-$d_6$): δ = |
|---|---|---|---|
| 69A | 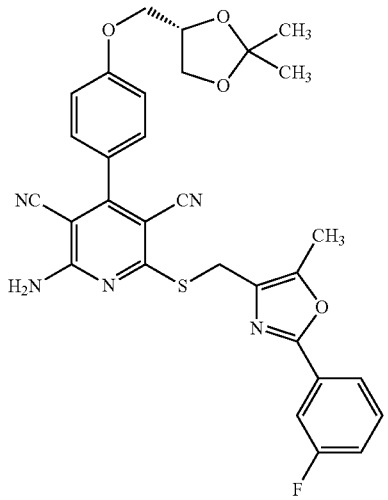<br>(75% of theory) | 3.01 min (3);<br>m/z = 572 | 8.16-7.97 (br. s, 2H), 7.78 (d, 1H), 7.66 (d, 1H), 7.58 (q, 1H), 7.49 (d, 2H), 7.37 (dt, 1H), 7.12 (d, 2H), 4.52 (s, 2H), 4.47-4.41 (m, 1H), 4.15-4.03 (m, 3H), 3.78 (dd, 1H), 2.48 (s, 3H), 1.37 (s, 3H), 1.31 (s, 3H). |
| 70A | 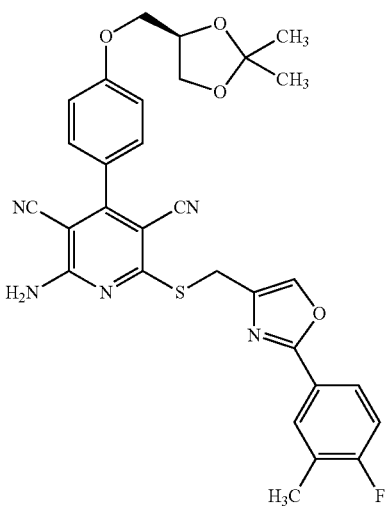<br>(80% of theory) | 2.62 min (6);<br>m/z = 572 | 8.33 (s, 1H), 8.25-7.97 (br. s, 2H), 7.92 (dd, 1H), 7.84-7.79 (m, 1H), 7.48 (d, 2H), 7.30 (t, 1H), 7.11 (d, 2H), 4.48-4.39 (m, 1H), 4.42 (s, 2H), 4.16-4.04 (m, 3H), 3.78 (dd, 1H), 2.31 (s, 3H), 1.38 (s, 3H), 1.32 (s, 3H). |

TABLE 4-continued
| Example No. | Structure (Yield) | LC-MS: R_t [min] (method); MS (ESI): m/z [M + H]+ | $^1$H-NMR (DMSO-$d_6$): δ = |
|---|---|---|---|
| 71A | 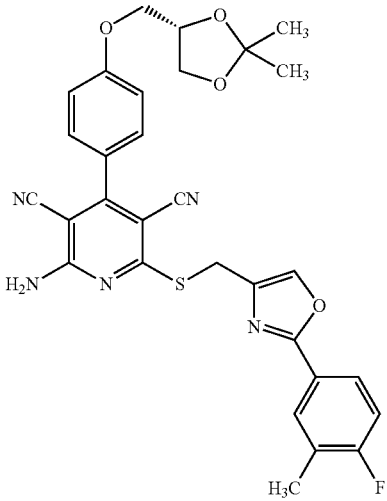 (78% of theory) | 2.62 min (6); m/z = 572 | 8.32 (s, 1H), 8.25-7.97 (br. s, 2H), 7.92 (dd, 1H), 7.85-7.80 (m, 1H), 7.48 (d, 2H), 7.30 (t, 1H), 7.12 (d, 2H), 4.48-4.39 (m, 1H), 4.41 (s, 2H), 4.16-4.04 (m, 3H), 3.79 (dd, 1H), 2.31 (s, 3H), 1.38 (s, 3H), 1.31 (s, 3H). |
| 72A | 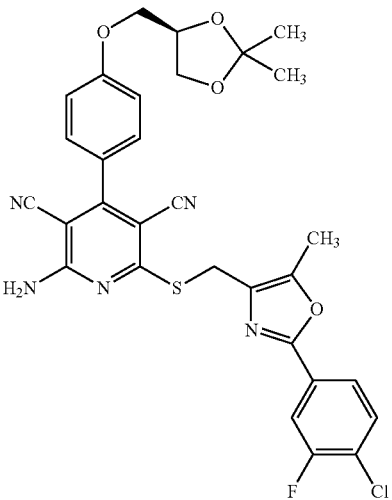 (71% of theory) | 3.21 min (3); m/z = 606 | 8.17-7.96 (br. s, 2H), 7.85 (dd, 1H), 7.75 (s, 1H), 7.74 (q, 1H), 7.49 (d, 2H), 7.12 (d, 2H), 4.52 (s, 2H), 4.47-4.40 (m, 1H), 4.15-4.04 (m, 3H), 3.78 (dd, 1H), 2.48 (s, 3H), 1.36 (s, 3H), 1.31 (s, 3H). |

TABLE 4-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 73A | 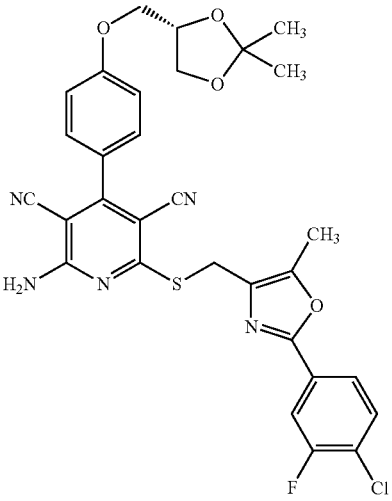 (66% of theory) | 3.21 min (3); m/z = 606 | 8.19-7.95 (br. s, 2H), 7.85 (dd, 1H), 7.75 (s, 1H), 7.74 (q, 1H), 7.49 (d, 2H), 7.12 (d, 2H), 4.52 (s, 2H), 4.48-4.41 (m, 1H), 4.15-4.04 (m, 3H), 3.78 (dd, 1H), 2.48 (s, 3H), 1.37 (s, 3H), 1.32 (s, 3H). |
| 74A | 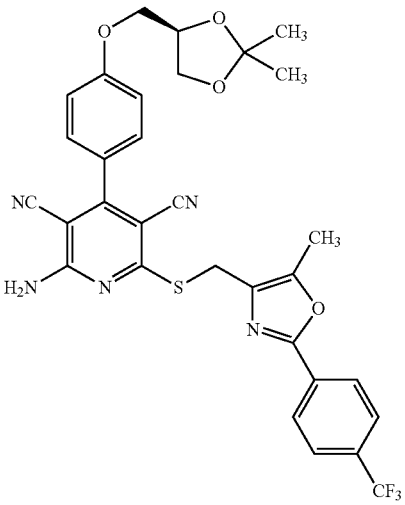 (49% of theory) | 3.10 min (3); m/z = 622 | 8.17-7.98 (br. s, 2H), 8.12 (d, 2H), 7.88 (d, 2H), 7.50 (d, 2H), 7.12 (d, 2H), 4.54 (s, 2H), 4.48-4.41 (m, 1H), 4.16-4.05 (m, 3H), 3.79 (dd, 1H), 2.51 (s, 3H), 1.38 (s, 3H), 1.32 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 75A | 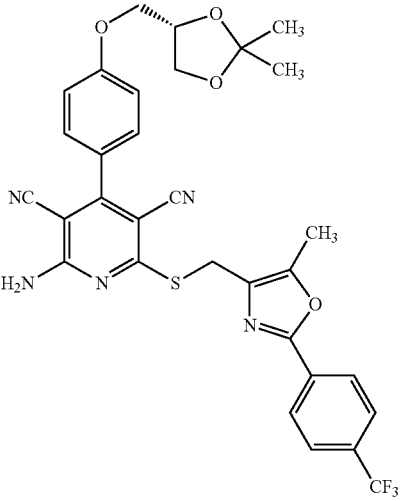 (54% of theory) | 2.56 min (7); m/z = 622 | 8.17-7.97 (br. s, 2H), 8.12 (d, 2H), 7.88 (d, 2H), 7.49 (d, 2H), 7.12 (d, 2H), 4.54 (s, 2H), 4.48-4.41 (m, 1H), 4.16-4.04 (m, 3H), 3.79 (dd, 1H), 2.50 (s, 3H), 1.38 (s, 3H), 1.32 (s, 3H). |
| 76A | 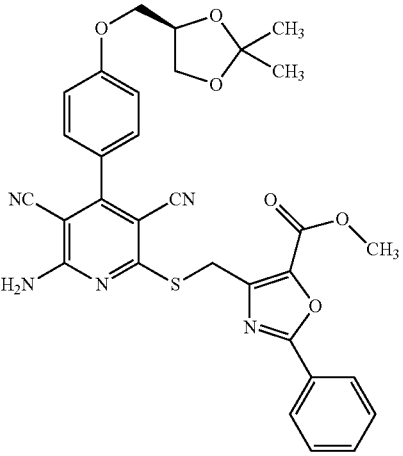 (66% of theory) | 1.41 min (14); m/z = 598 | 8.12-7.92 (br. s, 2H), 8.05 (d, 2H), 7.67-7.57 (m, 3H), 7.50 (d, 2H), 7.13 (d, 2H), 4.83 (s, 2H), 4.49-4.41 (m, 1H), 4.17-4.06 (m, 3H), 3.93 (s, 3H), 3.79 (dd, 1H), 1.38 (s, 3H), 1.31 (s, 3H). |
| 77A | 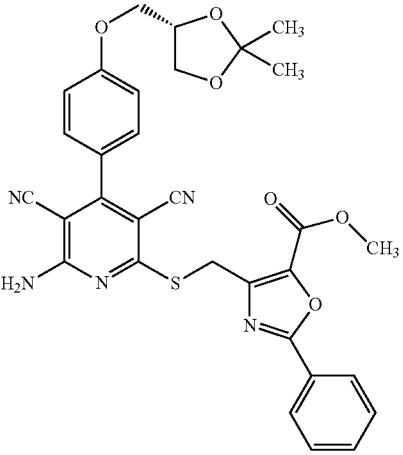 (67% of theory) | 2.36 min (7); m/z = 598 | 8.11-7.96 (br. s, 2H), 8.06 (d, 2H), 7.67-7.58 (m, 3H), 7.51 (d, 2H), 7.13 (d, 2H), 4.83 (s, 2H), 4.48-4.41 (m, 1H), 4.15-4.05 (m, 3H), 3.93 (s, 3H), 3.79 (dd, 1H), 1.38 (s, 3H), 1.31 (s, 3H). |

TABLE 4-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 78A | 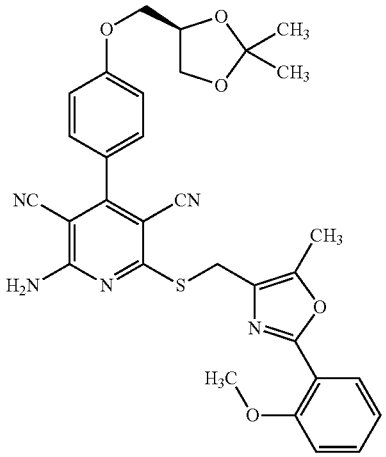<br>(75% of theory) | 1.36 min (14); m/z = 584 | 8.16-7.96 (br. s, 2H), 7.75 (dd, 1H), 7.50 (d, 2H), 7.48 (dd, 1H), 7.19 (d, 1H), 7.12 (d, 2H), 7.05 (t, 1H), 4.52 (s, 2H), 4.48-4.41 (m, 1H), 4.15-4.05 (m, 3H), 3.86 (s, 3H), 3.79 (dd, 1H), 2.43 (s, 3H), 1.37 (s, 3H), 1.30 (s, 3H). |
| 79A | 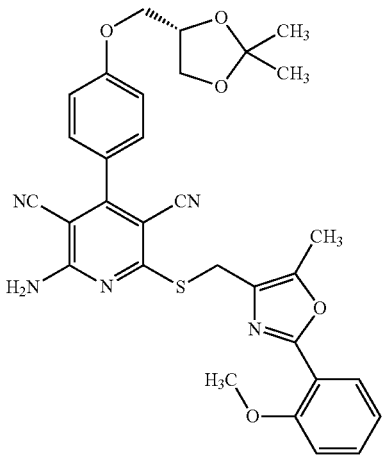<br>(78% of theory) | 2.26 min (7); m/z = 584 | 8.17-7.95 (br. s, 2H), 7.76 (dd, 1H), 7.50 (d, 2H), 7.48 (dd, 1H), 7.19 (d, 1H), 7.12 (d, 2H), 7.04 (t, 1H), 4.52 (s, 2H), 4.48-4.41 (m, 1H), 4.15-4.03 (m, 3H), 3.86 (s, 3H), 3.79 (dd, 1H), 2.44 (s, 3H), 1.37 (s, 3H), 1.31 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 80A | 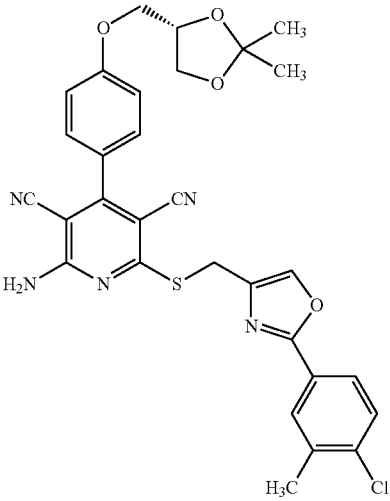 (54% of theory) | 3.21 min (3); m/z = 588 | |
| 81A | 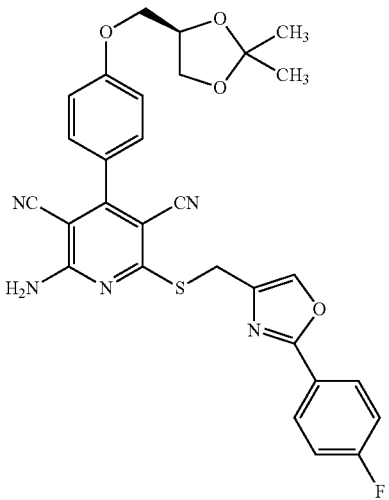 (68% of theory) | 2.32 min (7); m/z = 558 | 8.33 (s, 1H), 8.23-8.02 (br. s, 2H), 8.01 (dd, 2H), 7.48 (d, 2H), 7.38 (t, 2H), 7.12 (d, 2H), 4.49-4.40 (m, 1H), 4.52 (s, 2H), 4.15-4.03 (m, 3H), 3.78 (dd, 1H), 1.37 (s, 3H), 1.31 (s, 3H). |

TABLE 4-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 82A | 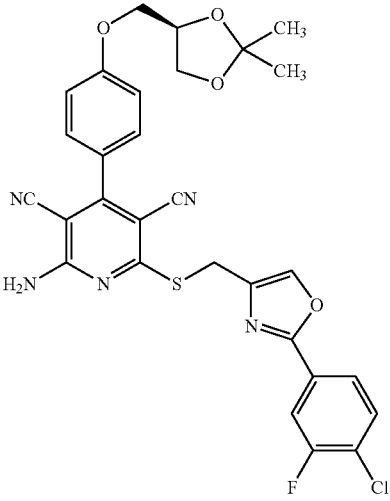 (41% of theory) | 1.49 min (14); m/z = 592 | |
| 83A | 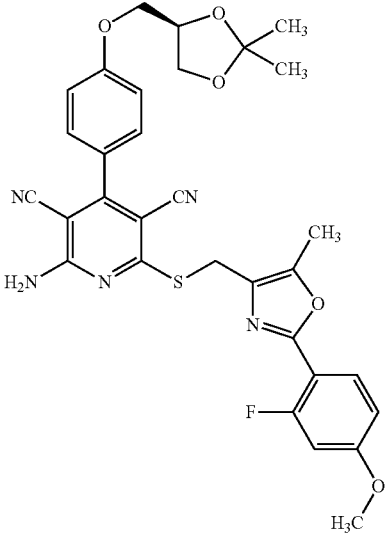 (59% of theory) | 1.40 min (14); m/z = 602 | 8.19-7.96 (br. s, 2H), 7.87 (t, 1H), 7.49 (d, 2H), 7.12 (d, 2H), 7.01 (dd, 1H), 6.92 (dd, 1H), 4.50 (s, 2H), 4.48-4.40 (m, 1H), 4.16-4.04 (m, 3H), 3.83 (s, 3H), 3.79 (dd, 1H), 2.45 (s, 3H), 1.38 (s, 3H), 1.31 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 84A | 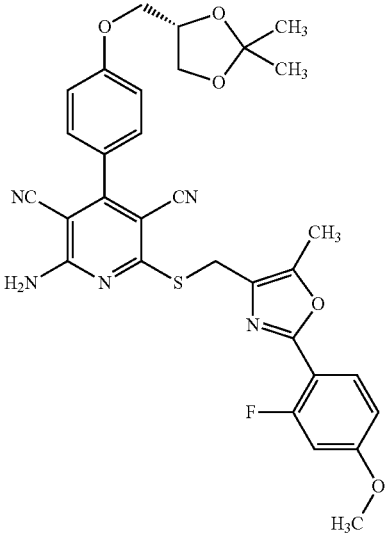<br>(58% of theory) | 1.40 min (14); m/z = 602 | 8.15-7.96 (br. s, 2H), 7.87 (t, 1H), 7.49 (d, 2H), 7.12 (d, 2H), 7.01 (dd, 1H), 6.92 (dd, 1H), 4.51 (s, 2H), 4.49-4.41 (m, 1H), 4.16-4.04 (m, 3H), 3.84 (s, 3H), 3.79 (dd, 1H), 2.45 (s, 3H), 1.37 (s, 3H), 1.31 (s, 3H). |
| 85A | 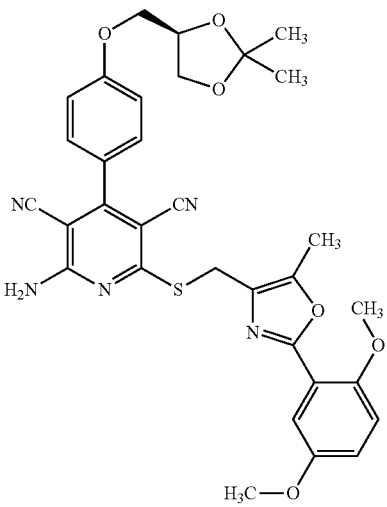<br>(82% of theory) | 1.35 min (14); m/z = 614 | 8.16-7.97 (br. s, 2H), 7.49 (d, 2H), 7.28 (d, 1H), 7.12 (d, 2H), 7.11 (dd, 1H), 7.06 (dd, 1H), 4.51 (s, 2H), 4.48-4.41 (m, 1H), 4.15-4.03 (m, 3H), 3.81-3.73 (m, 1H), 3.79 (s, 3H), 3.75 (s, 3H), 2.43 (s, 3H), 1.37 (s, 3H), 1.31 (s, 3H). |

TABLE 4-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 86A | 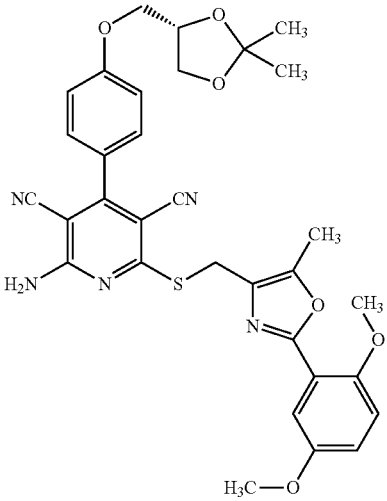 (73% of theory) | 1.35 min (14); m/z = 614 | 8.17-7.98 (br. s, 2H), 7.49 (d, 2H), 7.28 (d, 1H), 7.13 (d, 2H), 7.12 (dd, 1H), 7.07 (dd, 1H), 4.51 (s, 2H), 4.48-4.41 (m, 1H), 4.15-4.04 (m, 3H), 3.81-3.73 (m, 1H), 3.79 (s, 3H), 3.75 (s, 3H), 2.43 (s, 3H), 1.37 (s, 3H), 1.31 (s, 3H). |
| 87A | 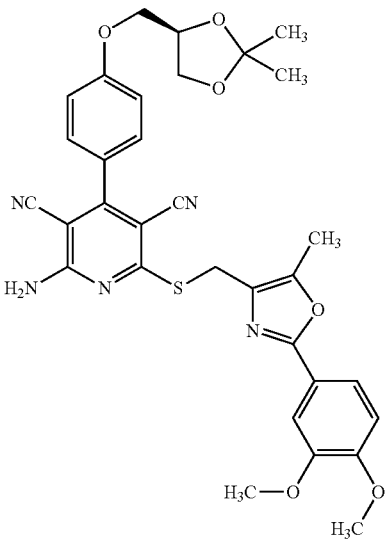 (73% of theory) | 2.50 min (15); m/z = 614 | 8.17-7.96 (br. s, 2H), 7.49 (d, 2H), 7.48 (d, 1H), 7.40 (s, 1H), 7.13 (d, 2H), 7.08 (d, 1H), 4.49 (s, 2H), 4.48-4.40 (m, 1H), 4.16-4.04 (m, 3H), 3.84 (s, 3H), 3.83 (s, 3H), 3.82-3.75 (m, 1H), 2.45 (s, 3H), 1.36 (s, 3H), 1.31 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 88A | 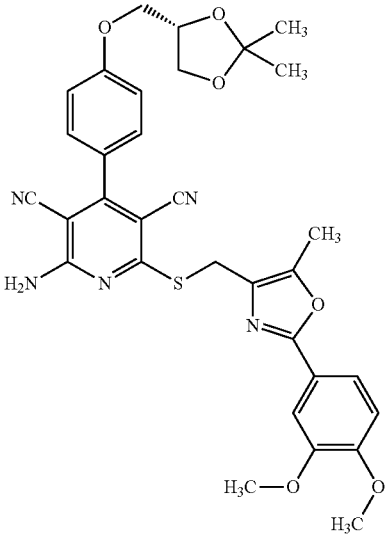<br>(73% of theory) | 2.50 min (15); m/z = 614 | 8.17-7.96 (br. s, 2H), 7.49 (d, 2H), 7.48 (d, 1H), 7.40 (s, 1H), 7.13 (d, 2H), 7.08 (d, 1H), 4.50 (s, 2H), 4.48-4.40 (m, 1H), 4.16-4.04 (m, 3H), 3.84 (s, 3H), 3.83 (s, 3H), 3.79 (dd, 1H), 2.45 (s, 3H), 1.36 (s, 3H), 1.31 (s, 3H). |
| 89A | 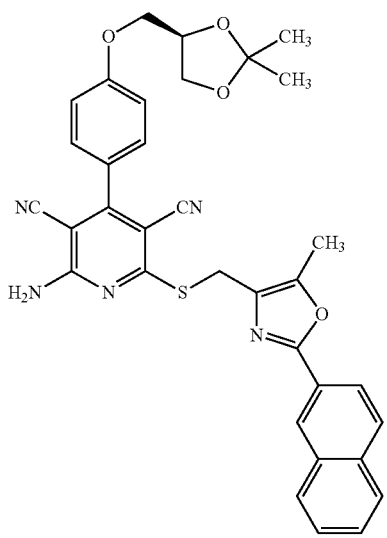<br>(35% of theory) | 2.56 min (7); m/z = 604 | 8.52 (s, 1H), 8.13-7.95 (br. s, 2H), 8.13-8.08 (m, 1H), 8.03 (s, 2H), 8.00-7.95 (m, 1H), 7.63-7.57 (m, 2H), 7.50 (d, 2H), 7.12 (d, 2H), 4.55 (s, 2H), 4.48-4.42 (m, 1H), 4.15-4.05 (m, 3H), 3.79 (dd, 1H), 2.49 (s, 3H), 1.38 (s, 3H), 1.32 (s, 3H). |

TABLE 4-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 90A | 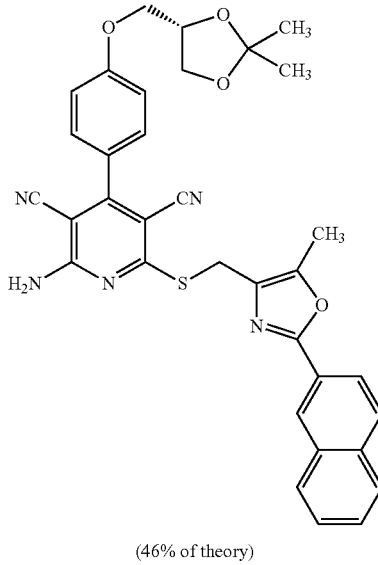<br>(46% of theory) | 2.56 min (7); m/z = 604 | 8.52 (s, 1H), 8.13-7.94 (br. s, 2H), 8.13-8.08 (m, 1H), 8.03 (s, 2H), 8.00-7.94 (m, 1H), 7.62-7.57 (m, 2H), 7.49 (d, 2H), 7.12 (d, 2H), 4.56 (s, 2H), 4.48-4.40 (m, 1H), 4.15-4.05 (m, 3H), 3.79 (dd, 1H), 2.50 (s, 3H), 1.38 (s, 3H), 1.32 (s, 3H). |
| 91A | 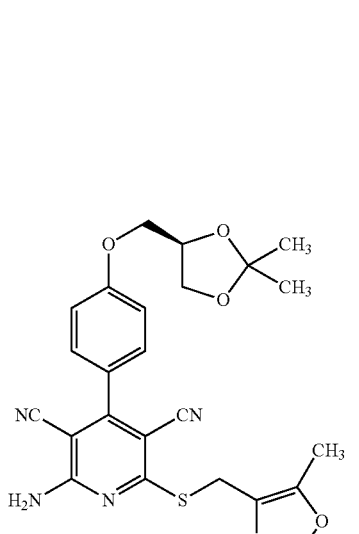<br>(82% of theory) | 2.76 min (15); m/z = 568 | 8.13-7.92 (br. s, 2H), 7.85 (d, 1H), 7.49 (d, 2H), 7.40-7.29 (m, 3H), 7.12 (d, 2H), 4.52 (s, 2H), 4.46-4.41 (m, 1H), 4.15-4.05 (m, 3H), 3.78 (dd, 1H), 2.60 (s, 3H), 2.47 (s, 3H), 1.37 (s, 3H), 1.31 (s, 3H). |

TABLE 4-continued
| Example No. | Structure (Yield) | LC-MS: R_t [min] (method); MS (ESI): m/z [M + H]+ | $^1$H-NMR (DMSO-d$_6$): δ = |
|---|---|---|---|
| 92A | 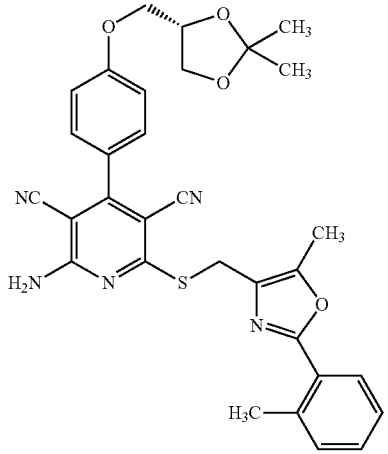 (78% of theory) | 2.76 min (15); m/z = 568 | 8.13-7.94 (br. s, 2H), 7.85 (d, 1H), 7.49 (d, 2H), 7.41-7.30 (m, 3H), 7.12 (d, 2H), 4.52 (s, 2H), 4.47-4.41 (m, 1H), 4.15-4.05 (m, 3H), 3.78 (dd, 1H), 2.60 (s, 3H), 2.47 (s, 3H), 1.38 (s, 3H), 1.32 (s, 3H). |
| 93A | 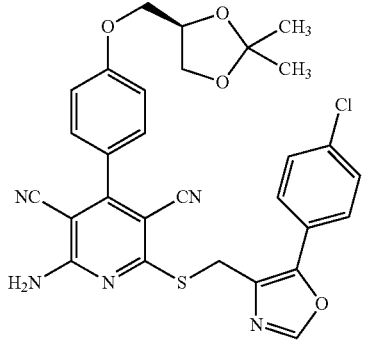 (99% of theory) | 1.42 min (14); m/z = 574 | 8.51 (s, 1H), 8.04-7.92 (br. s, 2H), 7.73 (d, 2H), 7.61 (d, 2H), 7.50 (d, 2H), 7.12 (d, 2H), 4.74 (s, 2H), 4.48-4.41 (m, 1H), 4.15-4.04 (m, 3H), 3.79 (dd, 1H), 1.37 (s, 3H), 1.31 (s, 3H). |
| 92A | 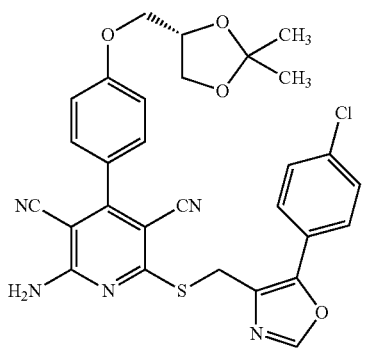 (82% of theory) | 1.42 min (14); m/z = 574 | 8.50 (s, 1H), 8.04-7.90 (br. s, 2H), 7.73 (d, 2H), 7.61 (d, 2H), 7.50 (d, 2H), 7.12 (d, 2H), 4.74 (s, 2H), 4.48-4.41 (m, 1H), 4.15-4.05 (m, 3H), 3.79 (dd, 1H), 1.38 (s, 3H), 1.31 (s, 3H). |

Example 95A

2-Amino-4-(4-{[(2S)-2-{[tert-butyl(dimethyl)silyl]oxy}propyl]oxy}phenyl)-6-({[2-(4-fluorophenyl)-5-methyl-1,3-oxazol-4-yl]methyl}thio)pyridine-3,5-dicarbonitrile

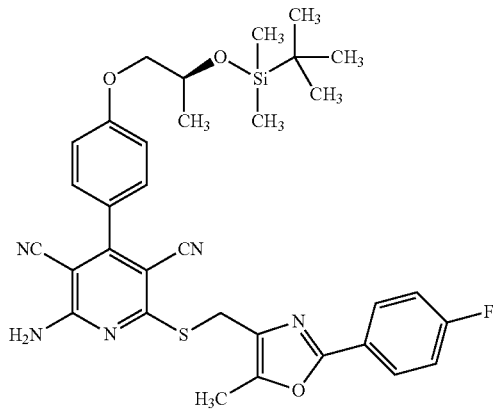 [SMILES: Cc1oc(-c2ccc(F)cc2)nc1CSc1nc(N)c(C#N)c(-c2ccc(OC[C@H](C)O[Si](C)(C)C(C)(C)C)cc2)c1C#N]

100 mg (0.18 mmol) of the compound from Example 7A, 45 mg (0.20 mmol) of 4-(chloromethyl)-2-(4-fluorophenyl)-5-methyl-1,3-oxazole and 46 mg (0.55 mmol) of sodium bicarbonate in 2 ml of dry DMF are stirred at RT for 20 h. The mixture is purified directly by preparative HPLC (column: YMC GEL ODS-AQ S-5/15 µm; mobile phase gradient: acetonitrile/water 10:90→95:5). Removal of the solvent on a rotary evaporator gives the product as a white solid.

Yield: 65 mg (57% of theory)

LC-MS (method 3): $R_t$=3.53 min; MS (ESIpos): m/z=630 $[M+H]^+$.

The examples listed in Table 5 are prepared analogously to Example 95A from the appropriate starting materials:

TABLE 5

| Example No. | Structure (Yield) | LC-MS: $R_t$ [min] (method); MS (ESI): m/z $[M + H]^+$ | $^1$H-NMR (DMSO-$d_6$): δ = |
|---|---|---|---|
| 96A | (84% of theory) | 5.04 min (4); m/z = 670 | 8.37 (s, 1H), 8.29-7.91 (br. s, 2H), 7.97 (d, 2H), 7.61 (d, 2H), 7.47 (d, 2H), 7.12 (d, 2H), 4.48-4.39 (m, 1H), 4.42 (s, 2H), 4.16-4.03 (m, 3H), 3.77 (dd, 1H), 1.37 (s, 3H), 1.31 (s, 3H). |

TABLE 5-continued

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 97A | 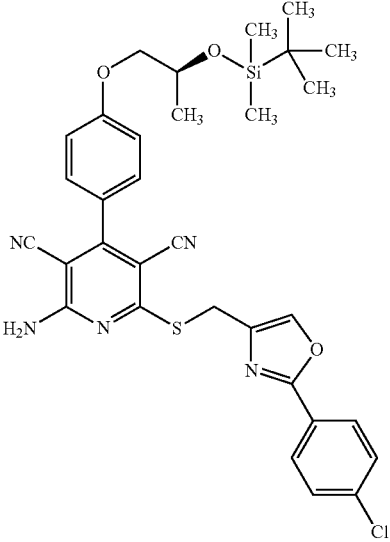 (99% of theory) | 5.14 min (4); m/z = 632 [M]$^+$ | |

Example 98A

2-Amino-4-(4-{[(4S)-2,2-dimethyl-1,3-dioxolan-4-yl]methoxy}-phenyl)-6-(phenylthio)pyridine-3,5-dicarbonitrile

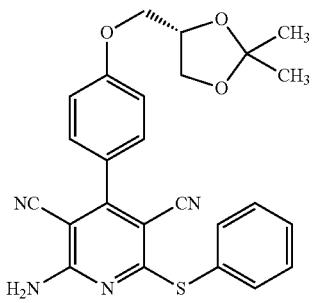 [SMILES: CC1(C)OC[C@H](COc2ccc(-c3c(C#N)c(N)nc(Sc4ccccc4)c3C#N)cc2)O1]

1.63 g (6.90 mmol) of the compound from Example 9A are initially charged in 25 ml of dry ethanol, and 957 mg (14.49 mmol) of malononitrile, 798 mg (7.24 mmol) of thiophenol and 21 mg (0.21 mmol) of triethylamine are added in succession. The reaction mixture is heated under reflux for 2 h. After cooling to RT, the solvent is removed on a rotary evaporator and the residue is purified directly by column chromatography on silica gel 60 (mobile phase: dichloromethane/methanol 60:1). Further purification is carried out by preparative HPLC (column: YMC GEL ODS-AQ S-5/15 μm; mobile phase gradient: acetonitrile/water 10:90→95:5).

Yield: 850 mg (27% of theory)

LC-MS (method 3): $R_t$=2.63 min; MS (ESIpos): m/z=459 [M+H]$^+$.

Example 99A

2-Amino-4-[4-(2-hydroxyethoxy)phenyl]-6-(phenylsulfanyl)pyridine-3,5-dicarbonitrile

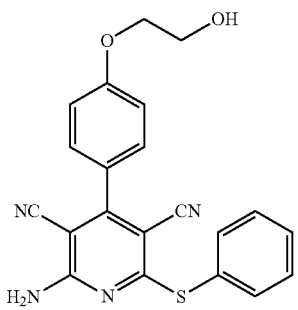 [SMILES: N#Cc1c(N)nc(Sc2ccccc2)c(C#N)c1-c1ccc(OCCO)cc1]

The title compound is prepared analogously to Example 98A from 4-(2-hydroxyethoxy)-benzaldehyde.

Yield: 21% of theory $^1$H-NMR (400 MHz, DMSO-$d_6$): δ=7.83-7.19 (br. s, 2H), 7.64-7.58 (m, 2H), 7.53-7.48 (m, 5H), 7.12 (d, 2H), 5.10-4.75 (br. s, 1H), 4.10 (t, 2H), 3.75 (t, 2H).

LC-MS (method 7): $R_t$=1.76 min; MS (ESIpos): m/z=389 [M+H]$^+$.

Example 100A

[2-(4-Chlorophenyl)-1,3-oxazol-4-yl]methanol

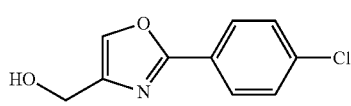 [SMILES: OCc1coc(-c2ccc(Cl)cc2)n1]

2.00 g (8.77 mmol) of the compound from Example 17A are suspended in 175 ml (17.54 mmol) of 0.1 N aqueous sodium hydroxide solution. The reaction mixture is stirred under reflux for 2 h. Using ice, the mixture is then cooled to 0° C., and a precipitate is formed slowly. About 100 ml of dichloromethane and 5 ml of ethanol are added to the mixture. The phases are separated. The aqueous phase is adjusted to pH 7 and extracted twice with in each case 50 ml of dichloromethane (with in each case 3 ml of ethanol). The combined organic phases are dried over magnesium sulfate. After removal of the solvent on a rotary evaporator, the residue is dried under reduced pressure.

Yield: 1.20 g (65% of theory)

LC-MS (method 8): $R_t$=3.05 min; MS (ESIpos): m/z=210 [M+H]$^+$.

Example 101A

2-Amino-6-{[2-(4-chlorophenyl)-1,3-oxazol-4-yl]methoxy}-4-(4-{[(4S)-2,2-dimethyl-1,3-dioxolan-4-yl]methoxy}phenyl)pyridine-3,5-dicarbonitrile

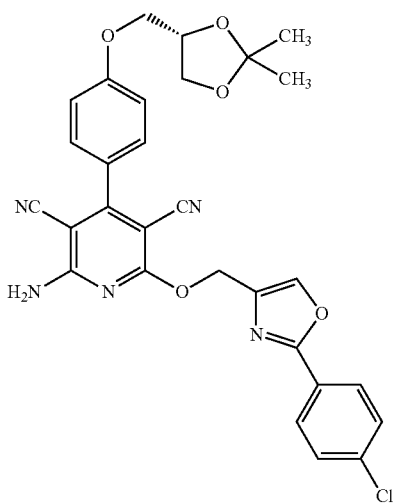 [SMILES: CC1(C)OC[C@H](COc2ccc(-c3c(C#N)c(N)nc(OCc4coc(-c5ccc(Cl)cc5)n4)c3C#N)cc2)O1]

122 mg (1.09 mmol) of potassium tert-butoxide are suspended in 2 ml of dry 1,2-dimethoxyethane. 229 mg (1.09 mmol) of the compound from Example 100A and 100 mg (0.22 mmol) of the compound from Example 98A are then added successively. The reaction mixture is stirred at 60° C. for 2 h and, after cooling, at RT for a further 10 h. 5 ml of water are then added to the mixture. The precipitate formed is filtered off with suction and washed once with about 2 ml of cold water. This is followed by purification by preparative HPLC (column: YMC GEL ODS-AQ S-5/15 μm; mobile phase gradient: acetonitrile/water 10:90→95:5).

Yield: 70 mg (58% of theory)

$^1$H-NMR (400 MHz, DMSO-d$_6$): δ=8.47 (s, 1H), 8.18-7.89 (br. s, 2H), 8.01 (d, 2H), 7.62 (d, 2H), 7.48 (d, 2H), 7.12 (d, 2H), 5.41 (s, 2H), 4.48-4.41 (m, 1H), 4.15-4.04 (m, 3H), 3.79 (dd, 1H), 1.37 (s, 3H), 1.31 (s, 3H).

LC-MS (method 3): $R_t$=2.82 min; MS (ESIpos): m/z=558 [M+H]$^+$.

Example 102A

6-Amino-4-[4-(2-hydroxyethoxy)phenyl]-2-oxo-1,2-dihydropyridine-3,5-dicarbonitrile

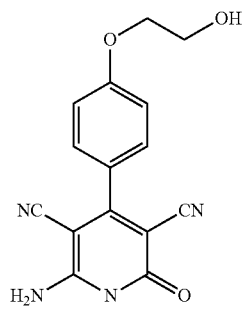 [SMILES: N#Cc1c(N)[nH]c(=O)c(C#N)c1-c1ccc(OCCO)cc1]

500 mg (1.29 mmol) of the compound from Example 99A are initially charged in 6.4 ml of ethanol. After addition of 2.57 g (28.96 mmol) of sodium hydroxide, the mixture is stirred at 80° C. for 30 min, and a clear solution is formed. After cooling to RT, the solvent is removed on a rotary evaporator. The residue is taken up in 3 ml of water and acidified with 1 N hydrochloric acid until a yellowish precipitate is formed. The suspension is stirred at RT for 3 h. The precipitate is filtered off, washed with about 5 ml of water and a little ethanol and then recrystallized from about 10 ml of ethanol. The product obtained in this manner is used without further purification in the subsequent reactions.

Yield: 153 mg (36% of theory, 89% purity)

$^1$H-NMR (400 MHz, DMSO-d$_6$): δ=11.85-11.72 (br. s, 1H), 7.87-7.60 (br. s, 2H), 7.43 (d, 2H), 7.10 (d, 2H), 5.08-4.52 (br. s, 1H), 4.08 (t, 2H), 3.74 (t, 2H).

LC-MS (method 3): $R_t$=1.29 min; MS (ESIpos): m/z=297 [M+H]$^+$.

Example 103A

2-Chloro-6-({[2-(4-chlorophenyl)-1,3-oxazol-4-yl]methyl}thio)-4-(4-{[(2S)-2,3-dihydroxypropyl]oxy}phenyl)pyridine-3,5-dicarbonitrile

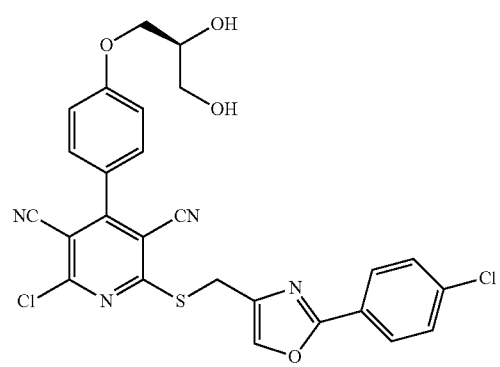 [SMILES: N#Cc1c(Cl)nc(SCc2coc(-c3ccc(Cl)cc3)n2)c(C#N)c1-c1ccc(OC[C@@H](O)CO)cc1]

569 mg (4.86 mmol) of isopentyl nitrite and 653 mg (4.86 mmol) of copper(II) chloride are initially charged in 20 ml of dry acetonitrile, and 465 mg (0.81 mmol) of the compound from Example 58A are added. The reaction mixture is stirred at 60° C. for 3 h. After cooling to RT, 20 ml of 1 N hydrochloric acid are added to the mixture. The aqueous phase is extracted twice with in each case 30 ml of ethyl acetate. The combined organic phases are washed in each case once with 10 ml of sat. aqueous sodium bicarbonate solution and 10 ml of sat. aqueous sodium chloride solution. After drying over magnesium sulfate, the solvent is removed on a rotary evaporator. The residue is purified by preparative HPLC (column: YMC GEL ODS-AQ S-5/15 μm; mobile phase gradient: acetonitrile/water 10:90→95:5). Removal of the solvent on a rotary evaporator gives the product which is used without further purification in the subsequent reaction.

Yield: 108 mg (18% of theory, 73% purity)

LC-MS (method 5): $R_t$=3.85 min; MS (ESIpos): m/z=553 [M+H]$^+$.

The examples listed in Table 6 are prepared analogously to Example 46A from the appropriate starting materials:

TABLE 6

| Example No. | Structure (Yield) | LC-MS: $R_t$ [min] (method); MS (ESI): m/z [M + H]$^+$ | $^1$H-NMR (DMSO-d$_6$): δ = |
| --- | --- | --- | --- |
| 104A | (93% of theory) | 2.82 min (3); m/z = 560 | 8.16-7.95 (br. s, 2H), 8.11 (d, 1H), 7.71 (dd, 1H), 7.51 (d, 1H), 7.49 (d, 2H), 7.12 (d, 2H), 4.48 (s, 2H), 4.47-4.40 (m, 1H), 4.16-4.03 (m, 3H), 3.79 (dd, 1H), 2.45 (s, 3H), 1.38 (s, 3H), 1.31 (s, 3H). |
| 105A | (76% of theory) | 2.82 min (3); m/z = 560 | 8.17-7.95 (br. s, 2H), 8.11 (d, 1H), 7.70 (dd, 1H), 7.52 (d, 1H), 7.49 (d, 2H), 7.12 (d, 2H), 4.49 (s, 2H), 4.47-4.40 (m, 1H), 4.15-4.03 (m, 3H), 3.78 (dd, 1H), 2.45 (s, 3H), 1.38 (s, 3H), 1.31 (s, 3H). |

The compounds listed in Table 7 can be prepared analogously to the procedures of Examples 16A and 34A from the appropriate starting materials:

TABLE 7

| Example No. | Structure | LC-MS: $R_t$ [min] (method); MS (ESI): m/z [M + H]$^+$ | $^1$H-NMR (400 MHz, DMSO-d$_6$): δ = |
|---|---|---|---|
| 106A | 4-(chloromethyl)-5-methyl-2-[4-(trifluoromethyl)phenyl]oxazole | 2.73 min (3); m/z = 276 | 8.13 (d, 2H), 7.90 (d, 2H), 4.79 (s, 2H), 2.48 (s, 3H). |
| 107A | 4-(chloromethyl)-2-(2-fluorophenyl)-5-methyloxazole | 2.31 min (3); m/z = 226 | 7.98 (dt, 1H), 7.62-7.54 (m, 1H), 7.44-7.33 (m, 2H), 4.78 (s, 2H), 2.46 (s, 3H). |
| 108A | 4-(chloromethyl)-2-(3-fluorophenyl)-5-methyloxazole | 2.45 min (3); m/z = 226 | 7.78 (d, 1H), 7.67 (d, 1H), 7.59 (q, 1H), 7.37 (dt, 1H), 4.77 (s, 2H), 2.46 (s, 3H). |
| 109A | 4-(chloromethyl)-2-(4-fluorophenyl)-5-methyloxazole | 2.42 min (3); m/z = 226 | 7.98 (dd, 2H), 7.37 (pseudo-t, 2H), 4.75 (s, 2H), 2.44 (s, 3H). |
| 110A | methyl 4-[4-(chloromethyl)-5-methyloxazol-2-yl]benzoate | 2.42 min (3); m/z = 266 | 8.12-8.04 (m, 4H), 4.79 (s, 2H), 3.89 (s, 3H), 2.48 (s, 3H). |

TABLE 7-continued

| Example No. | Structure | LC-MS: R$_t$ [min] (method); MS (ESI): m/z [M + H]$^+$ | $^1$H-NMR (400 MHz, DMSO-d$_6$): δ = |
|---|---|---|---|
| 111A | (structure: 4-(chloromethyl)-5-methyl-2-(2-fluoro-4-methoxyphenyl)oxazole) | 2.38 min (3); m/z = 256 | 7.88 (t, 1H), 7.02 (dd, 1H), 6.94 (dd, 1H), 4.76 (s, 2H), 3.84 (s, 3H), 2.42 (s, 3H). |
| 112A | (structure: 4-(chloromethyl)-5-methyl-2-(2,5-dimethyl-4-methoxyphenyl)oxazole) | 2.79 min (3); m/z = 266 | 7.65 (s, 1H), 6.91 (s, 1H), 4.73 (s, 2H), 3.83 (s, 3H), 2.59 (s, 3H), 2.41 (s, 3H), 2.16 (s, 3H). |
| 113A | (structure: 4-(chloromethyl)-5-methyl-2-(naphthalen-2-yl)oxazole) | 2.75 min (3); m/z = 258 | 8.54 (s, 1H), 8.13-8.08 (m, 1H), 8.05 (d, 2H), 8.02-7.96 (m, 1H), 7.63-7.58 (m, 2H), 4.80 (s, 2H), 2.49 (s, 3H). |
| 114A | (structure: 4-(chloromethyl)-5-methyl-2-(thiophen-3-yl)oxazole) | 2.21 min (3); m/z = 214 | 8.14 (d, 1H), 7.72 (dd, 1H), 7.53 (d, 1H), 4.73 (s, 2H), 2.41 (s, 3H). |
| 115A | (structure: 4-(chloromethyl)-5-methyl-2-(4-methoxyphenyl)oxazole) | 2.36 min (3); m/z = 238 | 7.87 (d, 2H), 7.08 (d, 2H), 4.72 (s, 2H), 3.82 (s, 3H), 2.42 (s, 3H). |

TABLE 7-continued

| Example No. | Structure | LC-MS: $R_t$ [min] (method); MS (ESI): m/z [M + H]$^+$ | $^1$H-NMR (400 MHz, DMSO-d$_6$): δ = |
|---|---|---|---|
| 116A | 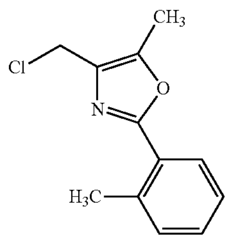 | 2.60 min (3); m/z = 221 | 7.88 (d, 1H), 7.43-7.31 (m, 3H), 4.78 (s, 2H), 2.61 (s, 3H), 2.43 (s, 3H). |
| 117A | 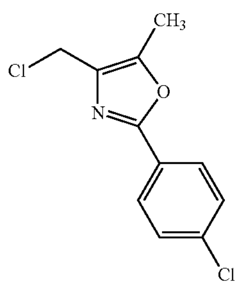 | 2.63 min (3); m/z = 242 | 7.94 (d, 2H), 7.60 (d, 2H), 4.77 (s, 2H), 2.45 (s, 3H). |
| 118A | 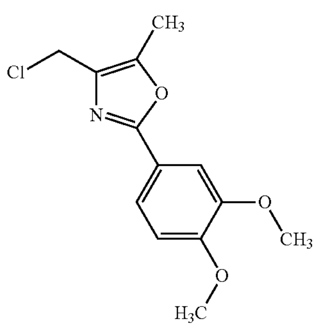 [SMILES: COc1ccc(-c2nc(CCl)c(C)o2)cc1OC] | 2.19 min (3); m/z = 268 | 7.50 (dd, 1H), 7.42 (s, 1H), 7.09 (d, 1H), 4.73 (s, 2H), 3.85 (s, 3H), 3.83 (s, 3H), 2.42 (s, 3H). |
| 119A | 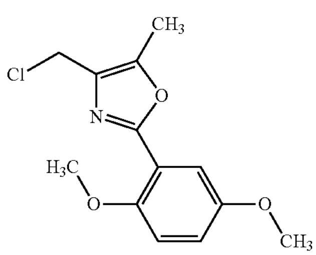 [SMILES: COc1ccc(OC)c(-c2nc(CCl)c(C)o2)c1] | 2.21 min (3); m/z = 268 | 7.30 (d, 1H), 7.13 (d, 1H), 7.08 (dd, 1H), 4.75 (s, 2H), 3.81 (s, 3H), 3.77 (s, 3H), 2.42 (s, 3H). |
| 120A | 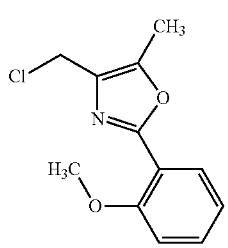 [SMILES: COc1ccccc1-c1nc(CCl)c(C)o1] | 2.19 min (3); m/z = 238 | 7.78 (d, 1H), 7.49 (dt, 1H), 7.19 (d, 1H), 7.06 (t, 1H), 4.75 (s, 2H), 3.86 (s, 3H), 2.42 (s, 3H). |

TABLE 7-continued

| Example No. | Structure | LC-MS: $R_t$ [min] (method); MS (ESI): m/z [M + H]$^+$ | $^1$H-NMR (400 MHz, DMSO-d$_6$): δ = |
|---|---|---|---|
| 121A | (structure) | 1.28 min (14); m/z = 246 | |
| 122A | (structure) | 2.84 min (6); m/z = 304 | 8.10 (d, 2H), 7.84 (d, 2H), 7.65 (d, 2H), 7.60 (t, 2H), 7.50 (t, 1H), 4.98 (s, 2H). |

Example 123A

2-Chloro-6-({[2-(4-chlorophenyl)-1,3-oxazol-4-yl]methyl}sulfanyl)-4-[4-(2-hydroxyethoxy)-phenyl]pyridine-3,5-dicarbonitrile

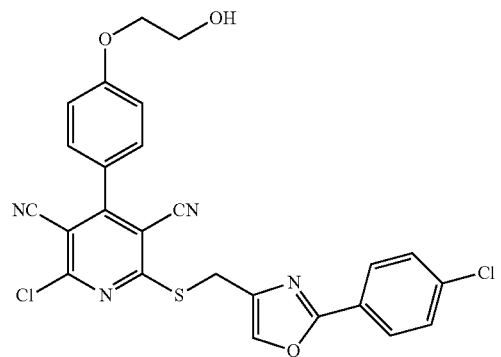 [SMILES: N#Cc1c(Cl)nc(SCc2coc(-c3ccc(Cl)cc3)n2)c(C#N)c1-c1ccc(OCCO)cc1]

156 mg (1.33 mmol) of isopentyl nitrite and 179 mg (1.33 mmol) of copper(II) chloride are initially charged in 17 ml of dry acetonitrile, and 336 mg (0.67 mmol) of the compound from Example 15 are added. The reaction mixture is stirred at 60° C. for 3 h. 17 ml of 1 N hydrochloric acid are then added, and the mixture is extracted twice with in each case 30 ml of ethyl acetate. The combined organic phases are dried over magnesium sulfate. After removal of the solvent, the crude product is used without further purification in the subsequent reaction.

Yield: 410 mg (78% of theory, 67% purity).

An 85 mg aliquot of the crude product is purified by preparative HPLC (column: YMC GEL ODS-AQ S-5/15 μm; mobile phase gradient: acetonitrile/water 10:90→95:5). This gives 14 mg of the pure target compound.

$^1$H-NMR (400 MHz, DMSO-d$_6$): δ=8.18 (s, 1H), 7.98 (d, 2H), 7.62 (dd, 4H), 7.19 (d, 2H), 4.98-4.88 (br. s, 1H), 4.58 (s, 2H), 4.11 (t, 2H), 3.79-3.71 (br. s, 2H).

LC-MS (method 14): $R_t$=1.46 min; MS (ESIpos): m/z=523 [M+H]$^+$.

Example 124A

2-Chloro-6-{[2-(4-chlorophenyl)-1,3-oxazol-4-yl]methoxy}-4-[4-(2-hydroxyethoxy)phenyl]-pyridine-3,5-dicarbonitrile

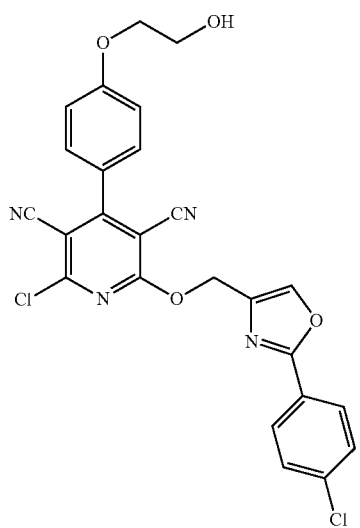 [SMILES: N#Cc1c(Cl)nc(OCc2coc(-c3ccc(Cl)cc3)n2)c(C#N)c1-c1ccc(OCCO)cc1]

113

The title compound is prepared analogously to Example 123A starting with Example 110.

LC-MS (method 3): $R_t$=2.76 min; MS (ESIpos): m/z=507 [M+H]$^+$.

Example 125A

2-Chloro-6-({[2-(4-chlorophenyl)-1,3-oxazol-4-yl]methyl}sulfanyl)-4-[3-fluoro-4-(2-hydroxy-ethoxy)phenyl]pyridine-3,5-dicarbonitrile

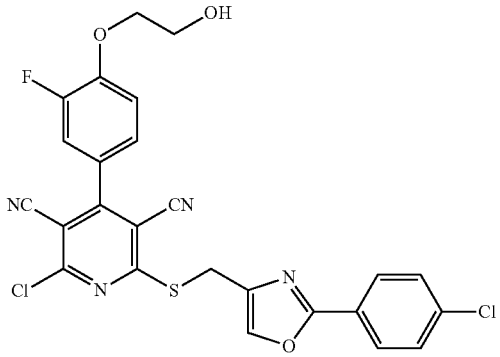 [SMILES: N#Cc1c(Cl)nc(SCc2coc(-c3ccc(Cl)cc3)n2)c(C#N)c1-c1ccc(OCCO)c(F)c1]

150 mg (0.287 mmol) of 2-amino-6-({[2-(4-chlorophenyl)-1,3-oxazol-4-yl]methyl}sulfanyl)-4-[3-fluoro-4-(2-hydroxyethoxy)phenyl]pyridine-3,5-dicarbonitrile (Example 20) are initially charged in 20 ml of acetonitrile, 258 μl (1.724 mmol) of isoamyl nitrite and 232 mg (1.724 mmol) of copper (II) chloride are added and the mixture is stirred at room temperature overnight. The reaction mixture is then added to saturated ammonium chloride solution and extracted with ethyl acetate. The organic phase is washed with saturated sodium chloride solution, dried over sodium sulfate and concentrated. The residue is purified by preparative HPLC (mobile phase gradient: acetonitrile/water 10:90→95:5). This gives 25 mg (16% of theory) of the target compound.

LC-MS (method 7): $R_t$=2.43 min; MS (ESIpos): m/z=541 [M+H]$^+$.

114

WORKING EXAMPLES

Example 1

2-Amino-6-({[2-(4-chloro-3-methylphenyl)-1,3-oxazol-4-yl]methyl}thio)-4-[4-(2-hydroxyethoxy)phenyl]pyridine-3,5-dicarbonitrile

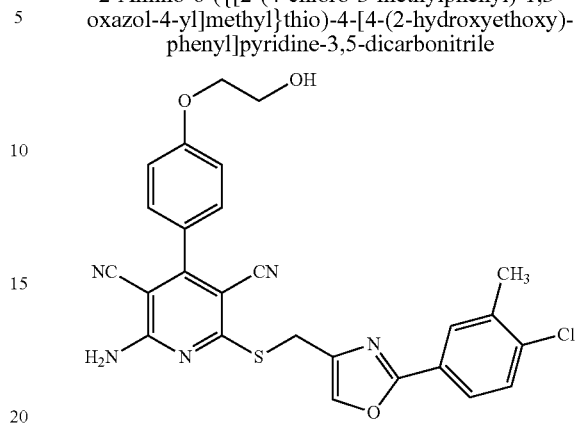

52 mg (0.17 mmol) of the compound from Example 1A and 89 mg (0.18 mmol) of the compound from Example 28A, together with 42 mg (0.50 mmol) of sodium bicarbonate, are suspended in 1.8 ml of dry DMF. The reaction mixture is stirred at RT for 12 h. The mixture is then filtered and the filtrate is purified directly by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 16 mg (38% of theory)

$^1$H-NMR (400 MHz, DMSO-d$_6$): δ=8.36 (s, 1H), 8.30-7.90 (br. s, 2H), 7.96 (s, 1H), 7.79 (d, 1H), 7.58 (d, 1H), 7.47 (d, 2H), 7.10 (d, 2H), 4.91 (t, 1H), 4.41 (s, 2H), 4.12-4.05 (m, 2H), 3.73 (dt, 2H), 2.41 (s, 3H).

LC-MS (method 6): $R_t$=2.36 min; MS (ESIpos): m/z=518 [M+H]$^+$.

The examples listed in Table 8 are prepared analogously to Example 1 from the appropriate starting materials:

TABLE 8

| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 2 | (80% of theory) | 3.63 min (4); m/z = 502 | 8.22-7.93 (br. s, 2H), 7.97 (d, 1H), 7.95 (d, 1H), 7.49 (d, 2H), 7.36 (t, 2H), 7.11 (d, 2H), 4.99 (t, 1H), 4.50 (s, 2H), 4.08 (t, 2H), 3.73 (dt, 2H), 2.45 (s, 3H). |

TABLE 8-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 3 | 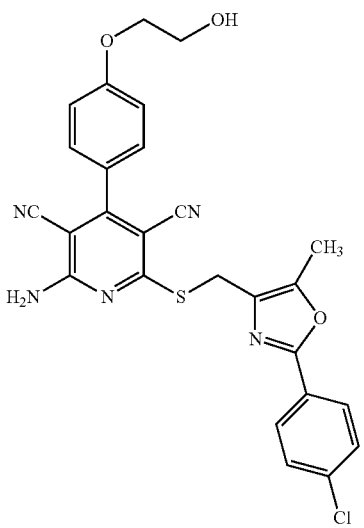<br>(47% of theory) | 2.15 min (7); m/z = 518 | 8.18-7.96 (br. s, 2H), 7.92 (d, 2H), 7.59 (d, 2H), 7.48 (d, 2H), 7.10 (d, 2H), 4.91 (t, 1H), 4.50 (s, 2H), 4.07 (t, 2H), 3.73 (dt, 2H), 2.47 (s, 3H). |
| 4 | 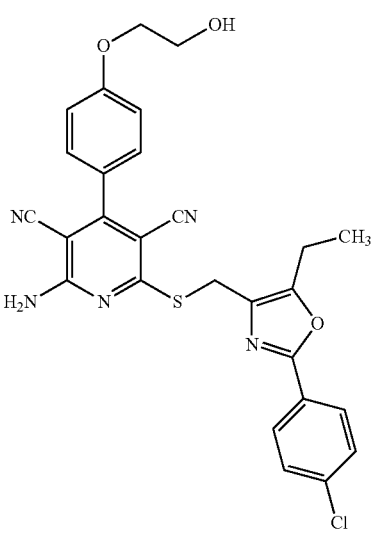<br>(40% of theory) | 2.43 min (6); m/z = 532 | 8.23-7.89 (br. s, 2H), 7.95 (d, 2H), 7.59 (d, 2H), 7.48 (d, 2H), 7.10 (d, 2H), 4.91 (t, 1H), 4.51 (s, 2H), 4.07 (t, 2H), 3.74 (q, 2H), 2.38 (dt, 2H), 1.20 (t, 3H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 5 | 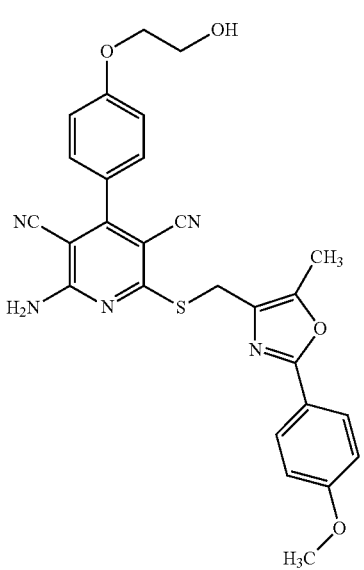<br>(66% of theory) | 2.53 min (3); m/z = 514 | 8.17-7.92 (br. s, 2H), 7.85 (d, 2H), 7.48 (d, 2H), 7.12 (d, 2H), 7.05 (d, 2H), 4.91 (t, 1H), 4.49 (s, 2H), 4.08 (t, 2H), 3.81 (s, 3H), 3.73 (dt, 2H), 2.44 (s, 3H). |
| 6 | 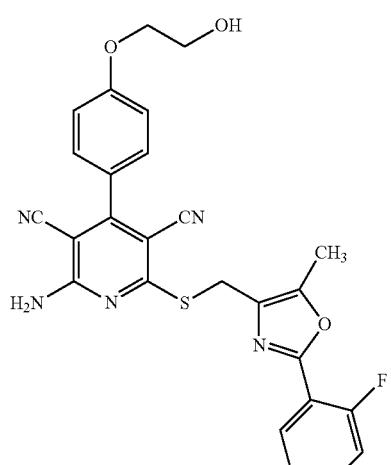<br>(53% of theory) | 2.50 min (3); m/z = 502 | 8.19-7.92 (br. s, 2H), 7.96 (t, 1H), 7.61-7.52 (m, 1H), 7.48 (d, 2H), 7.93-7.31 (m, 2H), 7.11 (d, 2H), 4.92 (t, 1H), 4.53 (s, 2H), 4.08 (t, 2H), 3.78-3.71 (m, 2H), 2.48 (s, 3H). |

TABLE 8-continued
| Example No. | Structure | LC-MS: R_t [min] (method); MS (ESI): m/z [M + H]+ | 1H-NMR (DMSO-d_6): δ = |
|---|---|---|---|
| 7 | 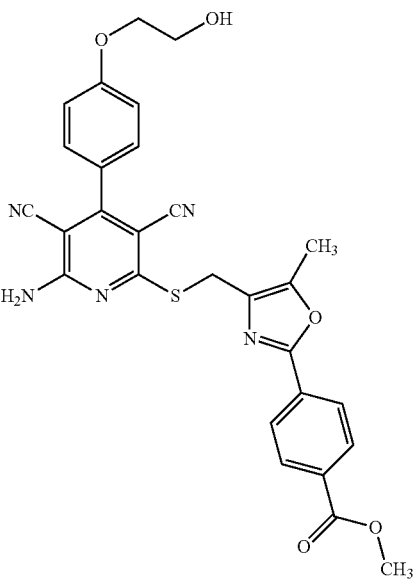<br>(16% of theory) | 3.44 min (5); m/z = 542 | 8.12-7.98 (m, 6H), 7.48 (d, 2H), 7.10 (d, 2H), 4.90 (t, 1H), 4.53 (s, 2H), 4.07 (t, 2H), 3.88 (s, 3H), 3.73 (dt, 2H), 2.50 (s, 3H). |
| 8 | 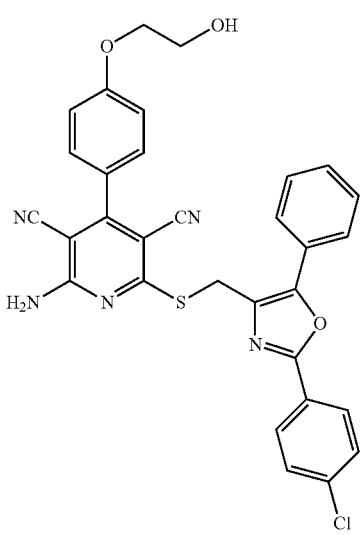<br>(42% of theory) | 3.10 min (3); m/z = 580 | 8.10 (d, 2H), 7.99-7.89 (br. s, 2H), 7.85 (d, 2H), 7.64 (d, 2H), 7.59 (d, 2H), 7.52-7.47 (m, 3H), 7.10 (d, 2H), 4.91 (t, 1H), 4.81 (s, 2H), 4.07 (t, 2H), 3.73 (dt, 2H). |

TABLE 8-continued
| Example No. | Structure (Yield) | LC-MS: R_t [min] (method); MS (ESI): m/z [M + H]+ | 1H-NMR (DMSO-d6): δ = |
|---|---|---|---|
| 9 | 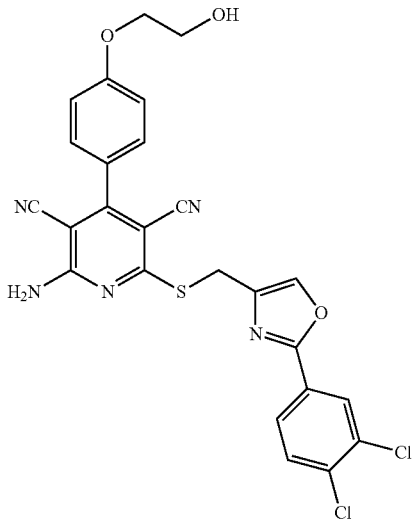<br>(84% of theory) | 2.84 min (3); m/z = 538 | 8.41 (s, 1H), 8.28-7.97 (br. s, 2H), 8.11 (d, 1H), 7.93 (dd, 1H), 7.80 (d, 1H), 7.48 (d, 2H), 7.10 (d, 2H), 4.91 (t, 1H), 4.42 (s, 2H), 4.08 (t, 2H), 3.75 (dt, 2H). |
| 10 | 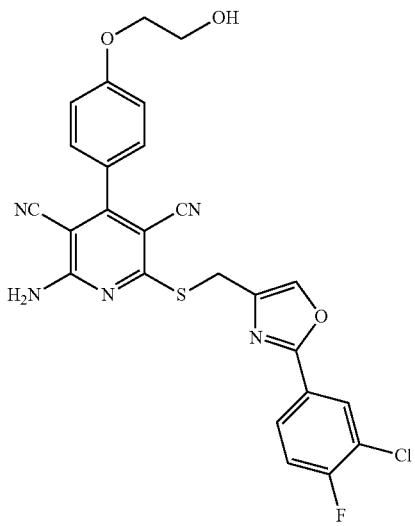<br>(87% of theory) | 2.70 min (3); m/z = 522 | 8.39 (s, 1H), 8.28-7.91 (br. s, 2H), 8.10 (dd, 1H), 8.00-7.94 (m, 1H), 7.59 (pseudo-t, 1H), 7.47 (d, 2H), 7.09 (d, 2H), 4.91 (t, 1H), 4.41 (s, 2H), 4.07 (t, 2H), 3.73 (dt, 2H). |

TABLE 8-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 11 | 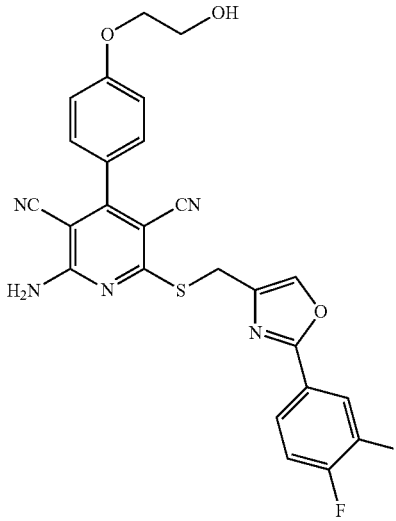<br>(71% of theory) | 2.43 min (9); m/z = 506 | 8.39 (s, 1H), 8.30-7.91 (br. s, 2H), 7.96 (dt, 1H), 7.87-7.78 (m, 1H), 7.62 (q, 1H), 7.47 (d, 2H), 7.10 (d, 2H), 4.90 (t, 1H), 4.42 (s, 2H), 4.11-4.03 (m, 2H), 3.73 (q, 2H). |
| 12 | 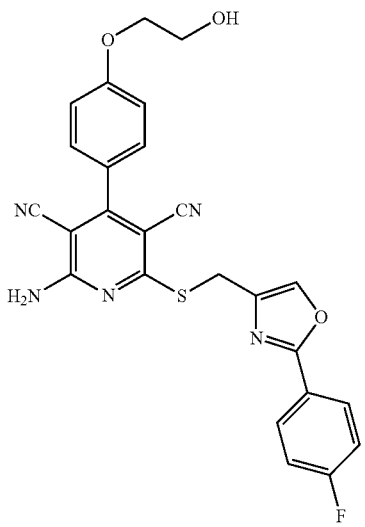<br>(75% of theory) | 2.44 min (9); m/z = 488 | 8.34 (s, 1H), 8.26-7.93 (br. s, 2H), 8.02 (d, 1H), 8.01 (d, 1H), 7.47 (d, 2H), 7.37 (t, 2H), 7.10 (d, 2H), 4.91 (t, 1H), 4.41 (s, 2H), 4.08 (t, 2H), 3.74 (q, 2H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 13 | 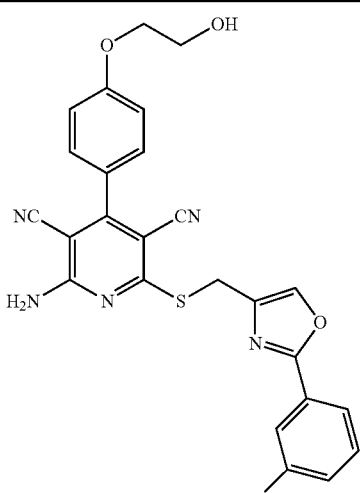<br>(72% of theory) | 2.41 min (9);<br>m/z = 488 | 8.48 (s, 1H), 8.27-7.93 (br. s, 2H), 7.83 (d, 1H), 7.72 (d, 1H), 7.60 (q, 1H), 7.47 (d, 2H), 7.39 (dt, 1H), 7.11 (d, 2H), 4.97 (t, 1H), 4.43 (s, 2H), 4.08 (t, 2H), 3.75 (q, 2H). |
| 14 | 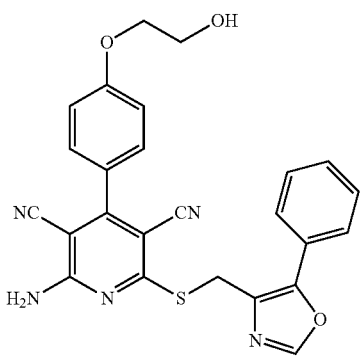<br>(9% of theory) | 2.29 min (9);<br>m/z = 470 | 8.48 (s, 1H), 7.98-7.82 (br. s, 2H), 7.72 (d, 2H), 7.58-7.43 (m, 5H), 7.11 (d, 2H), 4.93 (t, 1H), 4.73 (s, 2H), 4.09 (t, 2H), 3.74 (q, 2H). |
| 15 | 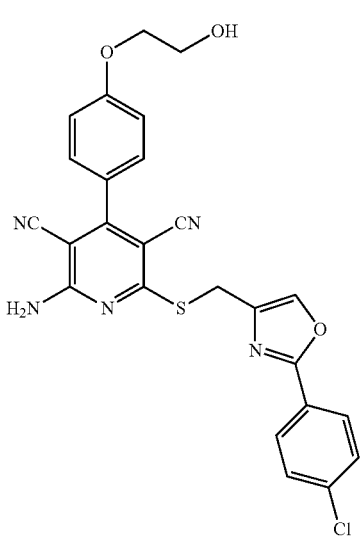<br>(77% of theory) | 2.53 min (3);<br>m/z = 504 | 8.37 (s, 1H), 8.31-7.89 (br. s, 2H), 7.97 (d, 2H), 7.60 (d, 2H), 7.46 (d, 2H), 7.10 (d, 2H), 4.91 (t, 1H), 4.41 (s, 2H), 4.08 (t, 2H), 3.74 (q, 2H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 16 | 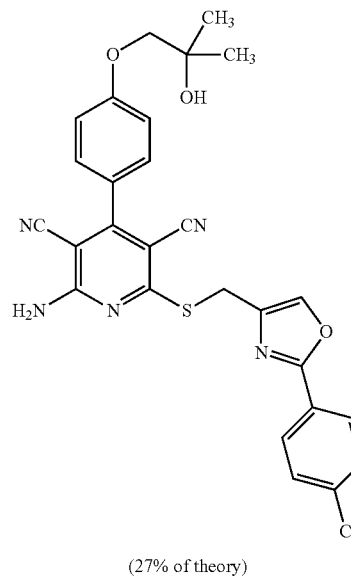 (27% of theory) | 2.83 min (3); m/z = 532 | 8.38 (s, 1H), 8.27-7.93 (br. s, 2H), 7.97 (d, 2H), 7.61 (d, 2H), 7.45 (d, 2H), 7.09 (d, 2H), 4.69 (s, 1H), 4.42 (s, 2H), 3.80 (s, 2H), 1.23 (s, 6H). |
| 17 | 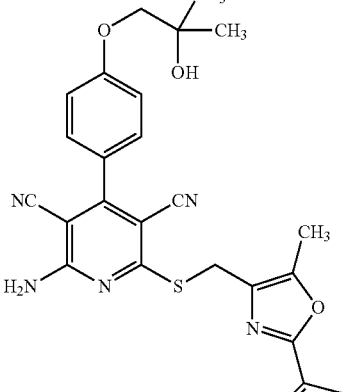 (17% of theory) | 3.83 min (4); m/z = 570 | 8.20-7.94 (br. s, 2H), 8.13-8.05 (m, 4H), 7.48 (d, 2H), 7.10 (d, 2H), 4.68 (s, 1H), 4.53 (s, 2H), 3.90 (s, 3H), 3.79 (s, 2H), 1.21 (s, 6H). |

TABLE 8-continued
| Example No. | Structure (Yield) | LC-MS: $R_t$ [min] (method); MS (ESI): m/z [M + H]⁺ | ¹H-NMR (DMSO-d₆): δ = |
|---|---|---|---|
| 18 | 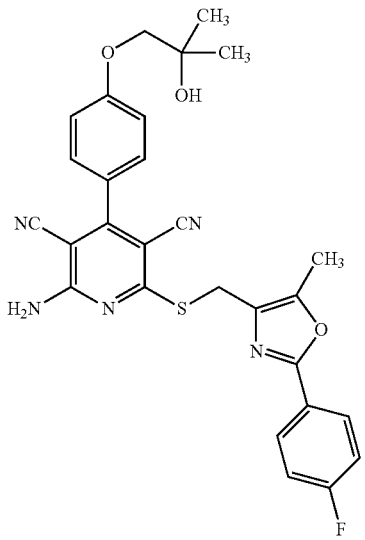<br>(30% of theory) | 2.76 min (3); m/z = 530 | 8.20-7.93 (br. s, 2H), 7.97 (dd, 2H), 7.48 (d, 2H), 7.35 (pseudo-t, 2H), 7.10 (d, 2H), 4.68 (s, 1H), 4.51 (s, 2H), 3.80 (s, 2H), 2.46 (s, 3H), 1.21 (s, 6H). |
| 19 | 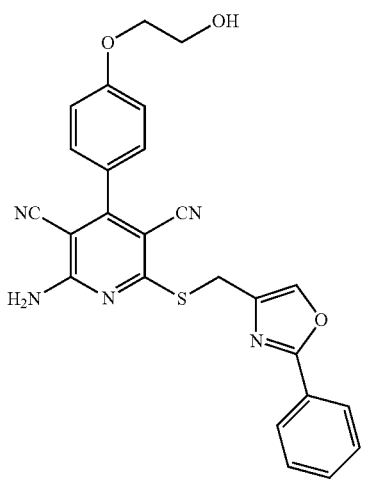<br>(54% of theory) | 2.49 min (3); m/z = 470 | 8.34 (s, 1H), 8.27-7.89 (br. s, 2H), 7.99-7.93 (m, 2H), 7.59-7.50 (m, 3H), 7.47 (d, 2H), 7.10 (d, 2H), 4.91 (t, 1H), 4.43 (s, 2H), 4.08 (t, 2H), 3.73 (q, 2H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 20 | 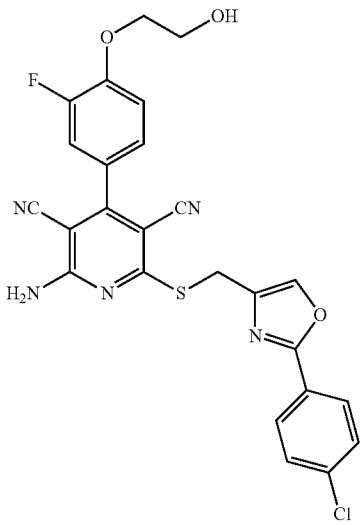<br>(82% of theory) | 1.30 min (14); m/z = 522 | 8.36 (s, 1H), 8.31-8.02 (br. s, 2H), 7.98 (d, 2H), 7.60 (d, 2H), 7.50 (dd, 1H), 7.39-7.29 (m, 2H), 4.96 (t, 1H), 4.43 (s, 2H), 4.17 (t, 2H), 3.76 (q, 2H). |
| 21 | 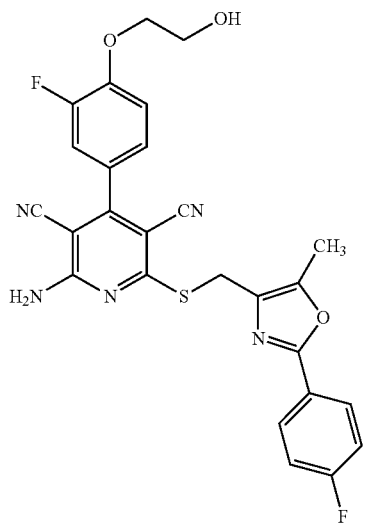<br>(84% of theory) | 1.26 min (14); m/z = 520 | 8.25-8.00 (br. s, 2H), 7.98 (d, 1H), 7.96 (d, 1H), 7.52 (dd, 1H), 7.40-7.30 (m, 4H), 4.96 (t, 1H), 4.51 (s, 2H), 4.17 (t, 2H), 3.75 (q, 2H), 2.47 (s, 3H). |

TABLE 8-continued
| Example No. | Structure (Yield) | LC-MS: R_t [min] (method); MS (ESI): m/z [M + H]+ | $^1$H-NMR (DMSO-d$_6$): δ = |
|---|---|---|---|
| 22 | 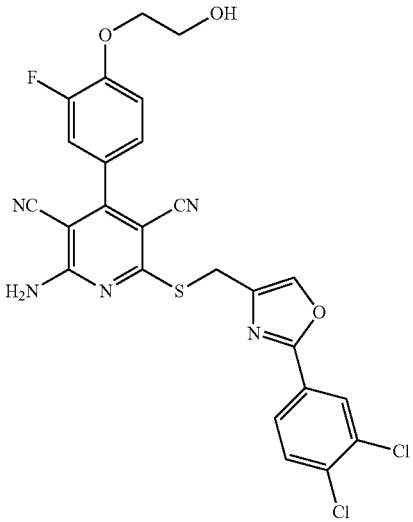 (87% of theory) | 1.39 min (14); m/z = 556 | 8.42 (s, 1H), 8.34-7.98 (br. s, 2H), 8.12 (s, 1H), 7.93 (dd, 1H), 7.81 (d, 1H), 7.49 (dd, 1H), 7.49-7.39 (m, 4H), 4.97 (t, 1H), 4.42 (s, 2H), 4.17 (t, 2H), 3.78 (q, 2H). |
| 23 | 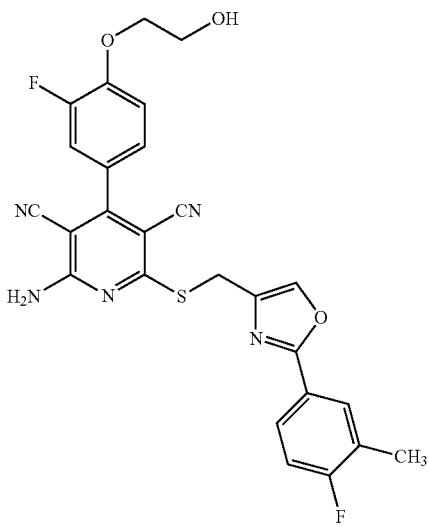 (69% of theory) | 1.26 min (14); m/z = 520 | 8.33 (s, 1H), 8.29-7.97 (br. s, 2H), 7.91 (dd, 1H), 7.85-7.78 (m, 1H), 7.49 (dd, 1H), 7.38-7.27 (m, 3H), 4.96 (t, 1H), 4.41 (s, 2H), 4.15 (t, 2H), 3.76 (q, 2H), 2.31 (s, 3H). |

TABLE 8-continued
| Example No. | Structure (Yield) | LC-MS: R_t [min] (method); MS (ESI): m/z [M + H]+ | 1H-NMR (DMSO-d6): δ = |
|---|---|---|---|
| 24 | 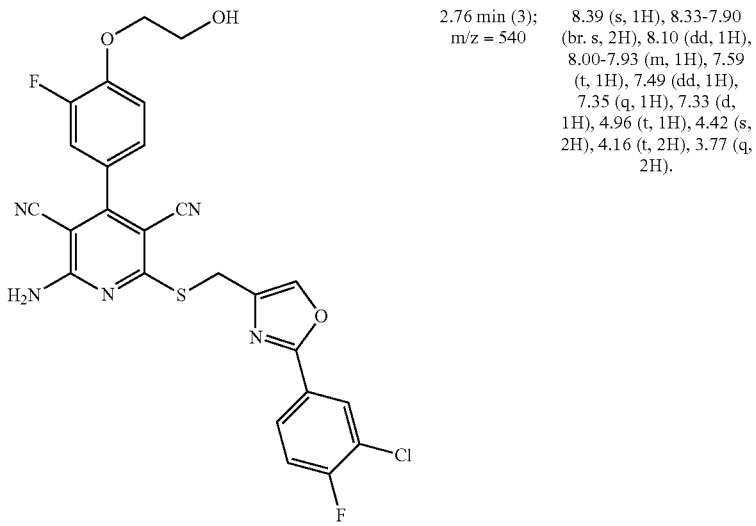<br>(69% of theory) | 2.76 min (3); m/z = 540 | 8.39 (s, 1H), 8.33-7.90 (br. s, 2H), 8.10 (dd, 1H), 8.00-7.93 (m, 1H), 7.59 (t, 1H), 7.49 (dd, 1H), 7.35 (q, 1H), 7.33 (d, 1H), 4.96 (t, 1H), 4.42 (s, 2H), 4.16 (t, 2H), 3.77 (q, 2H). |
| 25 | 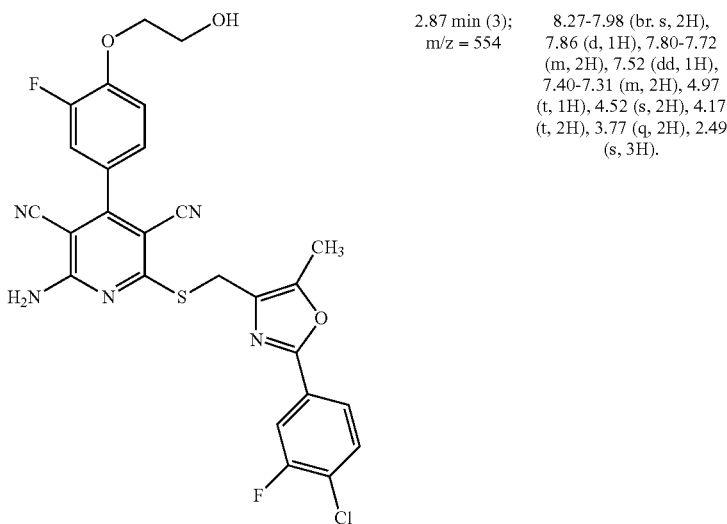<br>(67% of theory) | 2.87 min (3); m/z = 554 | 8.27-7.98 (br. s, 2H), 7.86 (d, 1H), 7.80-7.72 (m, 2H), 7.52 (dd, 1H), 7.40-7.31 (m, 2H), 4.97 (t, 1H), 4.52 (s, 2H), 4.17 (t, 2H), 3.77 (q, 2H), 2.49 (s, 3H). |

TABLE 8-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 26 | 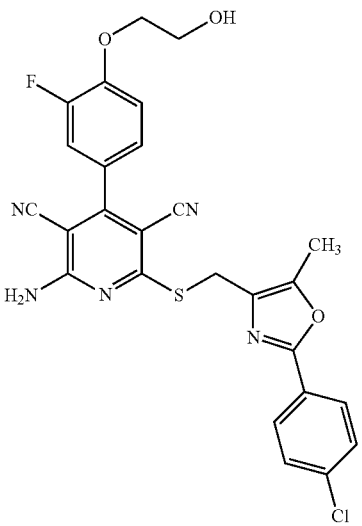<br>(74% of theory) | 2.81 min (3); m/z = 536 | 8.23-7.99 (br. s, 2H), 7.92 (d, 2H), 7.59 (d, 2H), 7.52 (dd, 1H), 7.36 (q, 1H), 7.35 (s, 1H), 4.96 (t, 1H), 4.51 (s, 2H), 4.17 (t, 2H), 3.77 (q, 2H), 2.46 (s, 3H). |
| 27 | 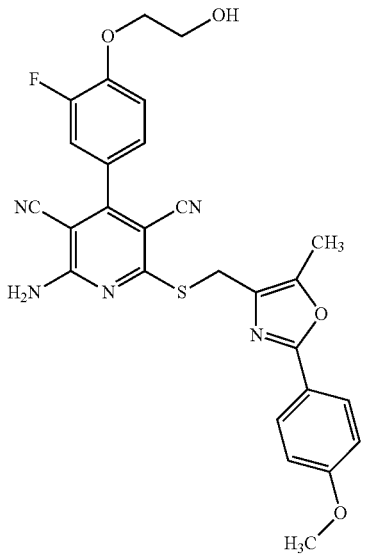<br>(89% of theory) | 2.61 min (3); m/z = 532 | 8.24-8.03 (br. s, 2H), 7.86 (d, 2H), 7.51 (dd, 1H), 7.36 (q, 1H), 7.34 (s, 1H), 7.07 (d, 2H), 4.96 (t, 1H), 4.49 (s, 2H), 4.18 (t, 2H), 3.81 (s, 3H), 3.76 (q, 2H), 2.45 (s, 3H). |

TABLE 8-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 28 | 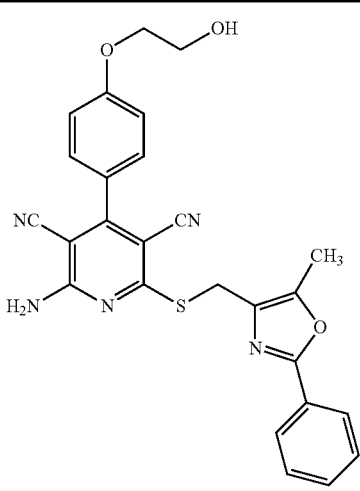 (80% of theory) | 2.77 min (3); m/z = 538 | 8.11-7.92 (br. s, 2H), 8.05 (d, 2H), 7.69-7.57 (m, 3H), 7.50 (d, 2H), 7.12 (d, 2H), 4.91 (t, 1H), 4.71 (s, 2H), 4.09 (t, 2H), 3.74 (q, 2H). |
| 29 | 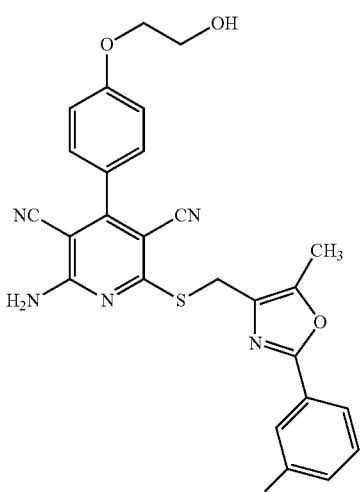 (45% of theory) | 2.20 min (6); m/z = 502 | 8.19-7.95 (br. s, 2H), 7.78 (d, 1H), 7.65 (dd, 1H), 7.57 (q, 1H), 7.49 (d, 2H), 7.36 (dt, 1H), 7.10 (d, 2H), 4.91 (t, 1H), 4.52 (s, 2H), 4.08 (t, 2H), 3.75 (q, 2H), 2.48 (s, 3H). |
| 30 | 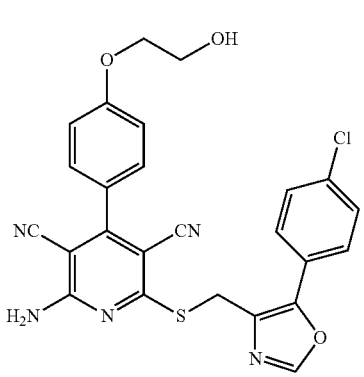 (79% of theory) | 1.22 min (14); m/z = 504 | 8.49 (s, 1H), 8.06-7.89 (br. s, 2H), 7.73 (d, 2H), 7.61 (d, 2H), 7.48 (d, 2H), 7.10 (d, 2H), 4.91 (t, 1H), 4.74 (s, 2H), 4.08 (t, 2H), 3.74 (q, 2H). |

TABLE 8-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 31 | 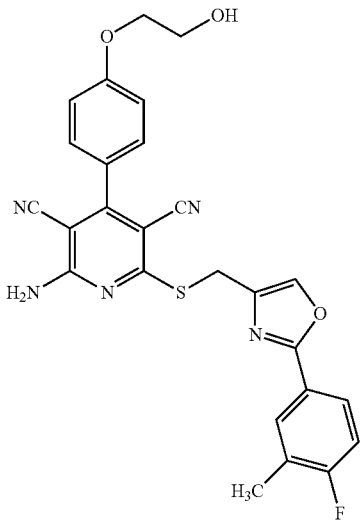<br>(56% of theory) | 2.23 min (6); m/z = 502 | 8.33 (s, 1H), 8.23-7.98 (br. s, 2H), 7.92 (d, 1H), 7.85-7.78 (m, 1H), 7.47 (d, 2H), 7.30 (t, 1H), 7.10 (d, 2H), 4.91 (t, 1H), 4.41 (s, 2H), 4.07 (t, 2H), 3.73 (q, 2H), 2.31 (s, 3H). |
| 32 | 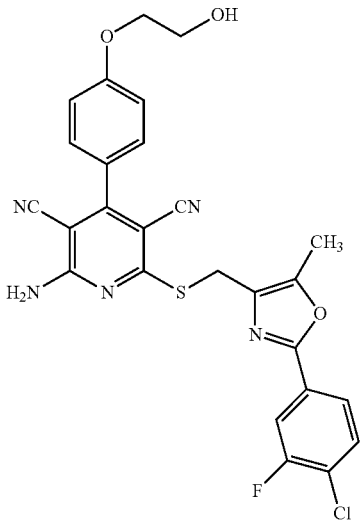<br>(61% of theory) | 2.83 min (3); m/z = 536 | 8.22-7.93 (br. s, 2H), 7.85 (dd, 1H), 7.79-7.71 (m, 2H), 7.48 (d, 2H), 7.12 (d, 2H), 4.91 (t, 1H), 4.52 (s, 2H), 4.07 (t, 2H), 3.73 (q, 2H), 2.48 (s, 3H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 33 | 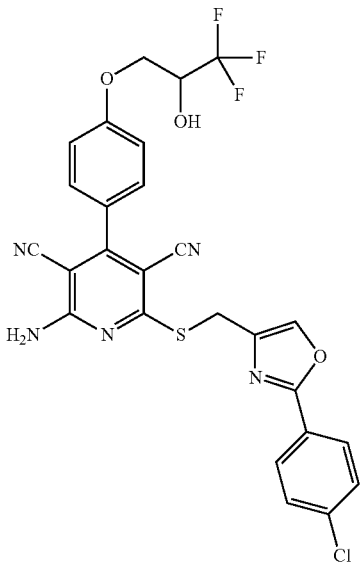 [SMILES: N#Cc1c(N)nc(SCc2coc(-c3ccc(Cl)cc3)n2)c(C#N)c1-c1ccc(OCC(O)C(F)(F)F)cc1]<br>(48% of theory) | 2.34 min (7); m/z = 572 | 8.37 (s, 1H), 8.27-7.91 (br. s, 2H), 7.97 (d, 2H), 7.60 (d, 2H), 7.48 (d, 2H), 7.14 (d, 2H), 6.69 (d, 1H), 4.49-4.38 (m, 1H), 4.43 (s, 2H), 4.27 (dd, 1H), 4.17 (dd, 1H). |
| 34 | 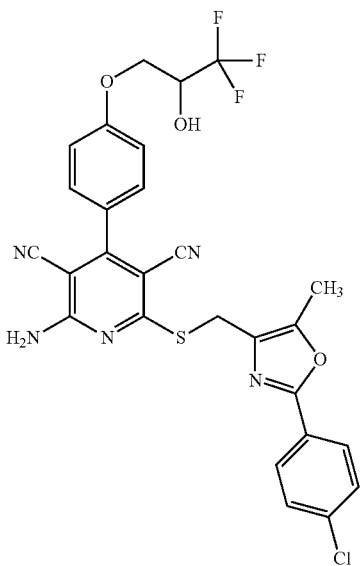<br>(61% of theory) | 2.41 min (7); m/z = 586 | 8.21-7.98 (br. s, 2H), 7.92 (d, 2H), 7.58 (d, 2H), 7.50 (d, 2H), 7.14 (d, 2H), 6.69 (d, 1H), 4.52 (s, 2H), 4.48-4.37 (m, 1H), 4.28 (dd, 1H), 4.16 (dd, 1H), 2.48 (s, 3H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 35 | 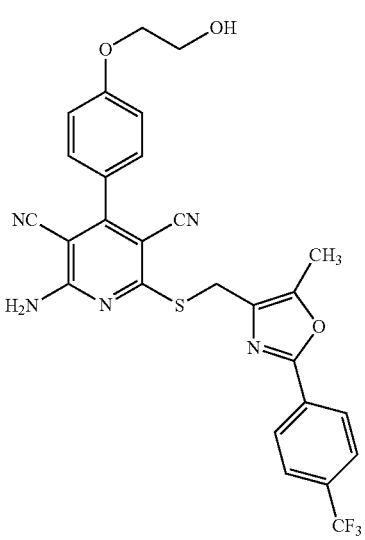<br>(46% of theory) | 2.20 min (7); m/z = 552 | 8.17-7.95 (br. s, 2H), 8.11 (d, 2H), 7.88 (d, 2H), 7.48 (d, 2H), 7.10 (d, 2H), 4.90 (t, 1H), 4.53 (s, 2H), 4.08 (t, 2H), 3.75 (q, 2H), 2.50 (s, 3H). |
| 36 | 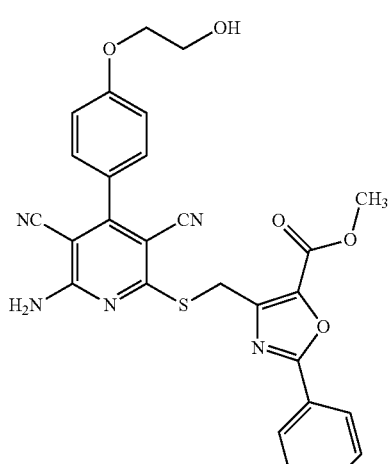<br>(35% of theory) | 2.60 min (3); m/z = 528 | 8.11-7.91 (br. s, 2H), 8.05 (d, 2H), 7.67-7.06 (m, 3H), 7.50 (d, 2H), 7.11 (d, 2H), 4.92 (t, 1H), 4.83 (s, 2H), 4.09 (t, 2H), 3.93 (s, 3H), 3.76 (q, 2H). |

TABLE 8-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 37 | 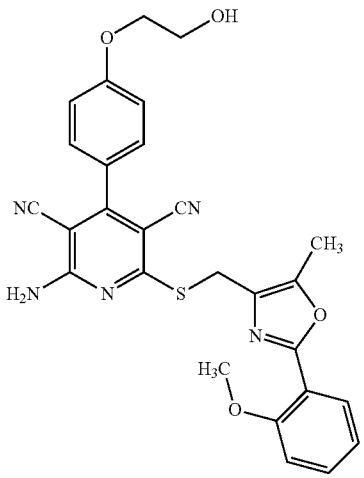<br>(80% of theory) | 1.16 min (14); m/z = 514 | 8.17-7.96 (br. s, 2H), 7.76 (dd, 1H), 7.52-7.46 (m, 1H), 7.50 (d, 2H), 7.19 (d, 1H), 7.11 (d, 2H), 7.06 (t, 1H), 4.91 (t, 1H), 4.52 (s, 2H), 4.08 (t, 2H), 3.85 (s, 3H), 3.75 (q, 2H), 2.45 (s, 3H). |
| 38 | 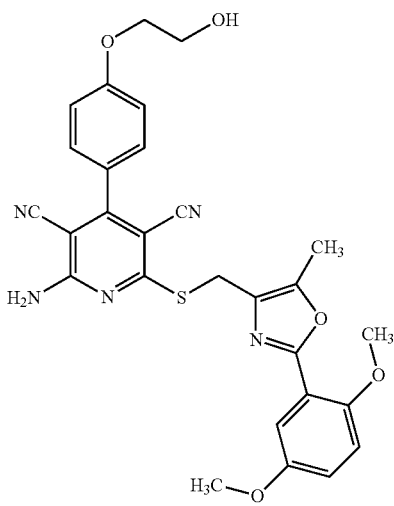<br>(86% of theory) | 1.16 min (14); m/z = 544 | 8.13-7.99 (br. s, 2H), 7.49 (d, 2H), 7.29 (d, 1H), 7.15-7.08 (m, 3H), 7.06 (dd, 1H), 4.91 (t, 1H), 4.51 (s, 2H), 4.08 (t, 2H), 3.80 (s, 3H), 3.77-3.71 (m, 2H), 3.76 (s, 3H), 2.43 (s, 3H). |

TABLE 8-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 39 | 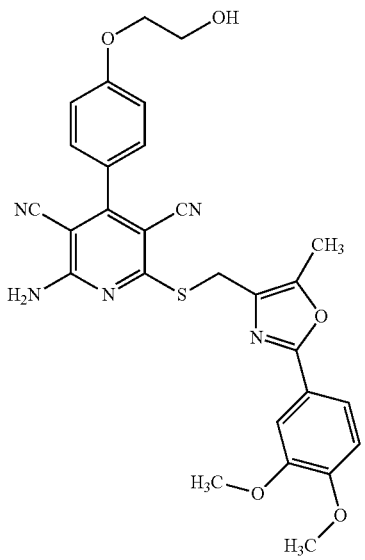<br>(59% of theory) | 2.29 min (3); m/z = 544 | 8.15-7.96 (br. s, 2H), 7.49 (d, 2H), 7.48 (d, 1H), 7.41 (s, 1H), 7.11 (d, 2H), 7.07 (d, 1H), 4.91 (t, 1H), 4.50 (s, 2H), 4.08 (t, 2H), 3.84 (s, 3H), 3.83 (s, 3H), 3.74 (q, 2H), 2.45 (s, 3H). |
| 40 | 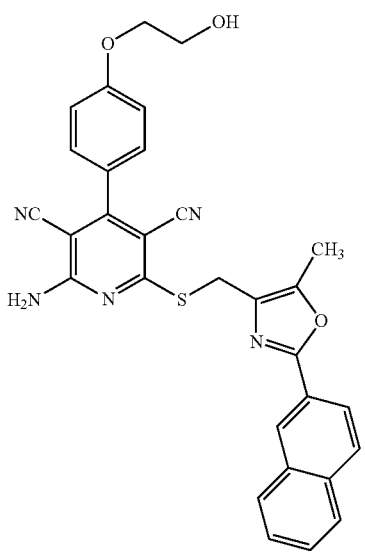<br>(91% of theory) | 1.35 min (14); m/z = 534 | 8.53 (s, 1H), 8.22-7.94 (br. s, 2H), 8.15-8.08 (m, 1H), 8.04 (s, 2H), 8.01-7.95 (m, 1H), 7.65-7.58 (m, 2H), 7.50 (d, 2H), 7.11 (d, 2H), 4.92 (t, 1H), 4.57 (s, 2H), 4.08 (t, 2H), 3.73 (q, 2H), 2.49 (s, 3H). |

TABLE 8-continued
| Example No. | Structure (Yield) | LC-MS: R_t [min] (method); MS (ESI): m/z [M + H]+ | $^1$H-NMR (DMSO-d$_6$): δ = |
|---|---|---|---|
| 41 | 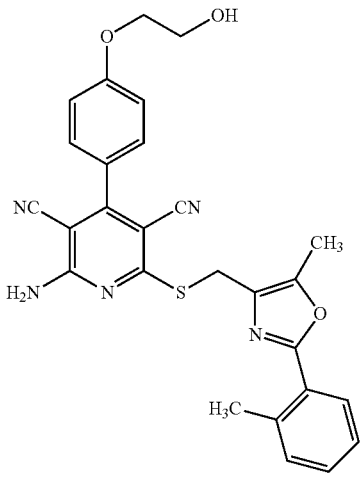<br>(97% of theory) | 1.30 min (14); m/z = 498 | 8.17-7.93 (br. s, 2H), 7.87 (d, 1H), 7.50 (d, 2H), 7.41-7.30 (m, 3H), 7.11 (d, 2H), 4.91 (t, 1H), 4.53 (s, 2H), 4.08 (t, 2H), 3.74 (q, 2H), 2.60 (s, 3H), 2.48 (s, 3H). |
| 42 | 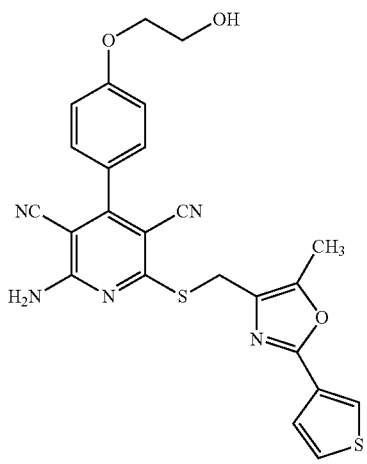<br>(85% of theory) | 2.17 min (15); m/z = 490 | 8.17-7.94 (br. s, 2H), 8.11 (d, 1H), 7.71 (dd, 1H), 7.52 (d, 1H), 7.49 (d, 2H), 7.10 (d, 2H), 4.91 (t, 1H), 4.49 (s, 2H), 4.08 (t, 2H), 3.74 (q, 2H), 2.45 (s, 3H). |

TABLE 8-continued

| Example No. | Structure (Yield) | LC-MS: $R_t$ [min] (method); MS (ESI): m/z [M + H]+ | 1H-NMR (DMSO-$d_6$): δ = |
|---|---|---|---|
| 43 | 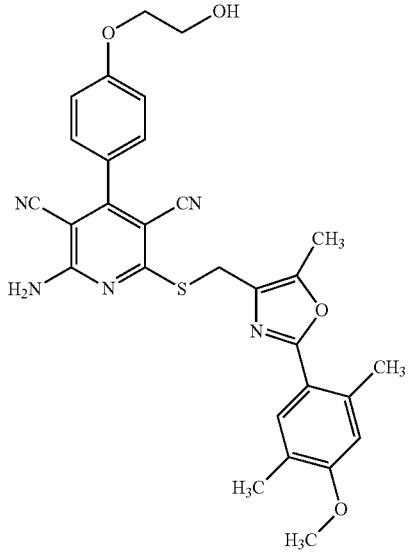<br>(93% of theory) | 2.21 min (7); m/z = 542 | 8.17-7.95 (br. s, 2H), 7.63 (s, 1H), 7.49 (d, 2H), 7.11 (d, 2H), 6.91 (s, 1H), 4.90 (t, 1H), 4.50 (s, 2H), 4.08 (t, 2H), 3.83 (s, 3H), 3.73 (q, 2H), 2.58 (s, 3H), 2.44 (s, 3H), 2.16 (s, 3H). |

Example 44

(+)-2-Amino-6-({[2-(4-chlorophenyl)-1,3-oxazol-4-yl]methyl}sulfanyl)-4-[4-(3,3,3-trifluoro-2-hydroxypropoxy)phenyl]pyridine-3,5-dicarbonitrile

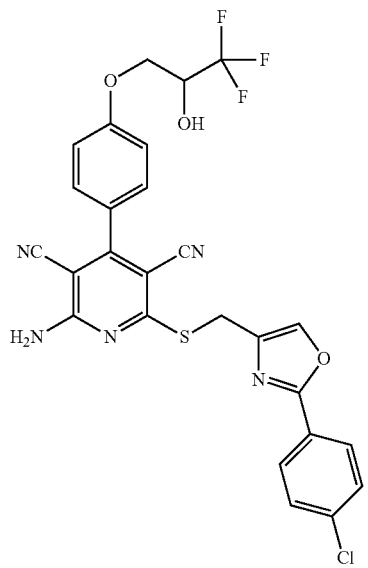 [SMILES: N#Cc1c(N)nc(SCc2coc(-c3ccc(Cl)cc3)n2)c(C#N)c1-c1ccc(OCC(O)C(F)(F)F)cc1]

The racemic compound from Example 33 (67 mg) is separated by HPLC chromatography on a chiral phase into the two enantiomers (see also Example 45) [column: Daicel Chiralpak AD-H, 5 nm, 250 mm×20 mm; mobile phase: ethanol; flow rate: 10 ml/min; temperature: 35° C.; detection: 220 nm].

(+)-Enantiomer:

Yield: 33 mg $R_t$=6.86 min [column: Daicel Chiralpak AD-H, 5 μm, 250 mm×4.6 mm; mobile phase: ethanol; flow rate: 1 ml/min; temperature: 40° C.]

Specific optical rotation: +1.2° (c=0.43 g/100 ml, methanol, n=589 nm, T=20.4° C.)

1H-NMR (400 MHz, DMSO-$d_6$): δ=8.37 (s, 1H), 8.28-7.91 (br. s, 2H), 7.98 (d, 2H), 7.61 (d, 2H), 7.49 (d, 2H), 7.15 (d, 2H), 6.70 (d, 1H), 4.49-4.39 (m, 1H), 4.43 (s, 2H), 4.28 (dd, 1H), 4.16 (dd, 1H).

LC-MS (method 7): $R_t$=2.34 min; MS (ESIpos): m/z=572 [M+H]+.

Example 45

(−)-2-Amino-6-({[2-(4-chlorophenyl)-1,3-oxazol-4-yl]methyl}sulfanyl)-4-[4-(3,3,3-trifluoro-2-hydroxypropoxy)phenyl]pyridine-3,5-dicarbonitrile

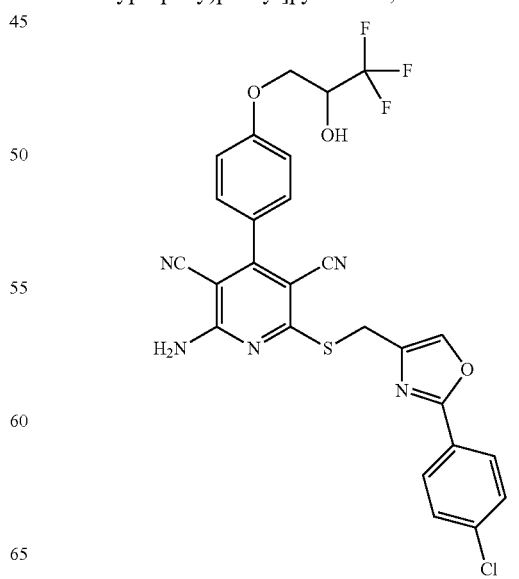

The racemic compound from Example 33 (67 mg) is separated by HPLC chromatography on a chiral phase into the two enantiomers (see also Example 44) [column: Daicel Chiralpak AD-H, 5 μm, 250 mm×20 mm; mobile phase: ethanol; flow rate: 10 ml/min; temperature: 35° C.; detection: 220 nm].

(−)-Enantiomer:

Yield: 33 mg $R_t$=8.73 min [column: Daicel Chiralpak AD-H, 5 μm, 250 mm×4.6 mm; mobile phase: ethanol; flow rate: 1 ml/min; temperature: 40° C.]

$^1$H-NMR (400 MHz, DMSO-$d_6$): δ=8.37 (s, 1H), 8.29-7.90 (br. s, 2H), 7.98 (d, 2H), 7.61 (d, 2H), 7.49 (d, 2H), 7.16 (d, 2H), 6.70 (d, 1H), 4.49-4.39 (m, 1H), 4.43 (s, 2H), 4.28 (dd, 1H), 4.16 (dd, 1H).

LC-MS (method 7): $R_t$=2.35 min; MS (ESIpos): m/z=572 [M+H]$^+$.

Example 46

(+)-2-Amino-6-({[2-(4-chlorophenyl)-5-methyl-1,3-oxazol-4-yl]methyl}sulfanyl)-4-[4-(3,3,3-trifluoro-2-hydroxypropoxy)phenyl]pyridine-3,5-dicarbonitrile

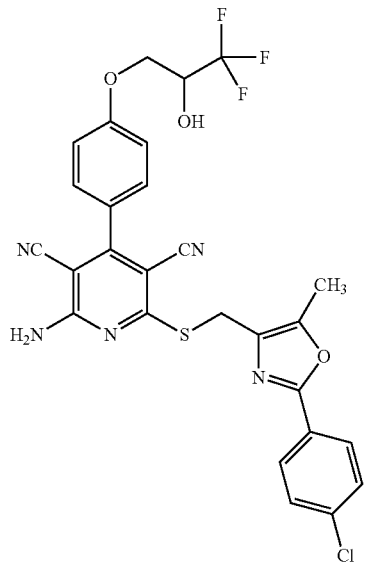 [SMILES: Cc1oc(-c2ccc(Cl)cc2)nc1CSc1nc(N)c(C#N)c(-c2ccc(OCC(O)C(F)(F)F)cc2)c1C#N]

The racemic compound from Example 34 (87 mg) is separated by HPLC chromatography on a chiral phase into the two enantiomers (see also Example 47) [column: Daicel Chiralpak AD-H, 5 μm, 250 mm×20 mm; mobile phase: isohexane/isopropanol 1:1 (v/v); flow rate: 15 ml/min; temperature: 40° C.; detection: 220 nm].

(+)-Enantiomer:

Yield: 30 mg $R_t$=4.58 min [column: Daicel Chiralpak AD-H, 5 μm, 250 mm×4.6 mm; mobile phase: isohexane/isopropanol 1:1 (v/v); flow rate: 1 ml/min; temperature: 40° C.]

Specific optical rotation: +11.1° (c=0.435 g/100 ml, DMF, n=589 nm, T=19.6° C.)

$^1$H-NMR (400 MHz, DMSO-$d_6$): δ=8.20-7.88 (br. s, 2H), 7.92 (d, 2H), 7.58 (d, 2H), 7.49 (d, 2H), 7.15 (d, 2H), 6.70 (d, 1H), 4.52 (s, 2H), 4.48-4.37 (m, 1H), 4.28 (dd, 1H), 4.17 (dd, 1H), 2.48 (s, 3H).

LC-MS (method 7): $R_t$=2.43 min; MS (ESIpos): m/z=586 [M+H]$^+$.

Example 47

(−)-2-Amino-6-({[2-(4-chlorophenyl)-5-methyl-1,3-oxazol-4-yl]methyl}sulfanyl)-4-[4-(3,3,3-trifluoro-2-hydroxypropoxy)phenyl]pyridine-3,5-dicarbonitrile

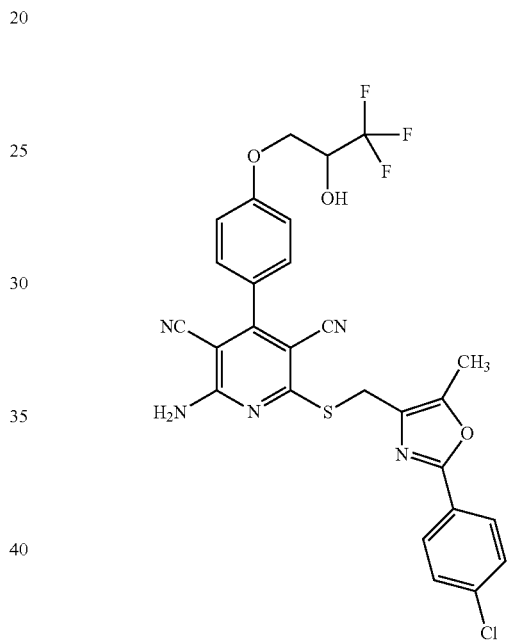

The racemic compound from Example 34 (87 mg) is separated by HPLC chromatography a chiral phase into the two enantiomers (see also Example 46) [column: Daicel Chiralpak AD-H, 5 μm, 250 mm×20 mm; mobile phase: isohexane/isopropanol 1:1 (v/v); flow rate: 15 ml/min; temperature: 40° C.; detection: 220 nm].

(−)-Enantiomer:

Yield: 31 mg $R_t$=5.56 min [column: Daicel Chiralpak AD-H, 5 μm, 250 mm×4.6 mm; mobile phase: isohexane/isopropanol 1:1 (v/v); flow rate: 1 ml/min; temperature: 40° C.]

$^1$H-NMR (400 MHz, DMSO-$d_6$): δ=8.21-7.89 (br. s, 2H), 7.92 (d, 2H), 7.58 (d, 2H), 7.50 (d, 2H), 7.16 (d, 2H), 6.70 (d, 1H), 4.52 (s, 2H), 4.48-4.39 (m, 1H), 4.29 (dd, 1H), 4.17 (dd, 1H), 2.48 (s, 3H).

LC-MS (method 7): $R_t$=2.43 min; MS (ESIpos): m/z=586 [M+H]$^+$.

Example 48

2-Amino-6-({[2-(4-chlorophenyl)-1,3-oxazol-4-yl]methyl}sulfanyl)-4-(4-{[(2S)-2,3-dihydroxypropyl]oxy}phenyl)pyridine-3,5-dicarbonitrile

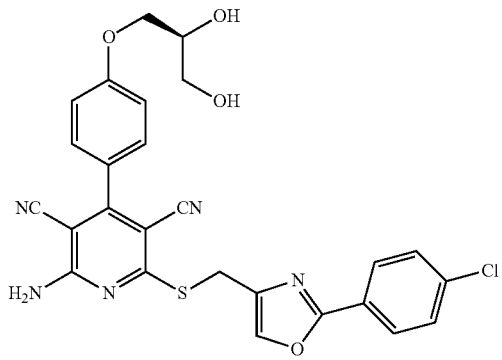 [SMILES: N#Cc1c(N)nc(SCc2coc(-c3ccc(Cl)cc3)n2)c(C#N)c1-c1ccc(OC[C@@H](O)CO)cc1]

400 mg (0.70 mmol) of the compound from Example 46A are initially charged in 17 ml of acetic acid, and 8.6 ml of water are then added carefully. The mixture is stirred at RT for 12 h. After concentration of the reaction mixture on a rotary evaporator, the residue is purified directly by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 340 mg (91% of theory)

$^1$H-NMR (400 MHz, DMSO-$d_6$): δ=8.37 (s, 1H), 8.27-7.91 (br. s, 2H), 7.98 (d, 2H), 7.60 (d, 2H), 7.47 (d, 2H), 7.10 (d, 2H), 5.00 (d, 1H), 4.70 (t, 1H), 4.42 (s, 2H), 4.09 (dd, 1H), 3.96 (dd, 1H), 3.70 (q, 1H), 3.46 (t, 2H).

LC-MS (method 3): $R_t$=2.48 min; MS (ESIpos): m/z=534 [M+H]$^+$.

Example 49

2-Amino-6-({[2-(4-chlorophenyl)-1,3-oxazol-4-yl]methyl}sulfanyl)-4-(4-{[(2R)-2,3-dihydroxypropyl]oxy}phenyl)pyridine-3,5-dicarbonitrile 403 mg (80% pure, 0.56 mmol) of the compound from Example 47A are initially charged in 23.5 ml of acetic acid, and 23.5 ml of water are then added carefully. The reaction mixture is stirred at RT overnight and then concentrated on a rotary evaporator. The residue is taken up in a little DMF and purified by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 259 mg (86% of theory)

$^1$H-NMR (400 MHz, DMSO-$d_6$): δ=8.37 (s, 1H), 8.30-7.89 (br. s, 2H), 7.98 (d, 2H), 7.61 (d, 2H), 7.48 (d, 2H), 7.10 (d, 2H), 5.00 (d, 1H), 4.70 (t, 1H), 4.42 (s, 2H), 4.09 (dd, 1H), 3.98-3.92 (m, 1H), 3.81 (q, 1H), 3.50-3.43 (m, 2H).

LC-MS (method 3): $R_t$=2.51 min; MS (ESIpos): m/z=534 [M+H]$^+$.

The examples listed in Table 9 are prepared analogously to Examples 48 and 49 from the appropriate starting materials:

TABLE 9

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 50 | (94% of theory) | 2.43 min (3); mz = 532 | 8.20-7.92 (br. s, 2H), 7.97 (d, 1H), 7.96 (d, 1H), 7.48 (d, 2H), 7.35 (pseudo-t, 2H), 7.10 (d, 2H), 5.00 (d, 1H), 4.69 (t, 1H), 4.50 (s, 2H), 4.09 (dd, 1H), 3.96 (dd, 1H), 3.82 (q, 1H), 3.47 (t, 2H), 2.43 (s, 3H). |

TABLE 9-continued
| Example No. | Structure (Yield) | LC-MS: R_t [min] (method); MS (ESI): m/z [M + H]+ | $^1$H-NMR (DMSO-$d_6$): δ = |
|---|---|---|---|
| 51 | 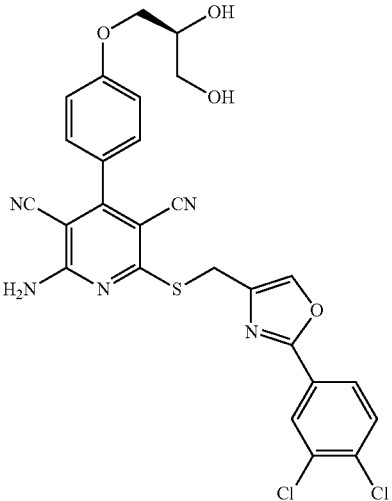 (71% of theory) | 2.65 min (3); m/z = 568 | 8.41 (s, 1H), 8.32-7.97 (br. s, 2H), 8.12 (d, 1H), 7.92 (dd, 1H), 7.70 (d, 1H), 7.47 (d, 2H), 7.10 (d, 2H), 5.00 (d, 1H), 4.69 (t, 1H), 4.42 (s, 2H), 4.09 (dd, 1H), 3.94 (dd, 1H), 3.86-3.77 (m, 1H), 3.47 (t, 2H). |
| 52 | 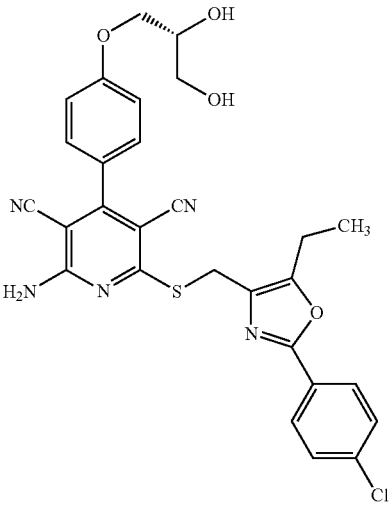 [SMILES: CCc1oc(-c2ccc(Cl)cc2)nc1CSc1nc(N)c(C#N)c(-c2ccc(OC[C@H](O)CO)cc2)c1C#N] (75% of theory) | 2.69 min (3); m/z = 562 | 8.24-7.89 (br. s, 2H), 7.95 (d, 2H), 7.59 (d, 2H), 7.48 (d, 2H), 7.10 (d, 2H), 5.01 (d, 1H), 4.70 (t, 1H), 4.51 (s, 2H), 4.09 (dd, 1H), 3.96 (dd, 1H), 3.86-3.78 (m, 1H), 3.48 (t, 2H), 2.89 (q, 2H), 1.21 (t, 3H). |

TABLE 9-continued
| Example No. | Structure (Yield) | LC-MS: $R_t$ [min] (method); MS (ESI): m/z [M + H]⁺ | ¹H-NMR (DMSO-d₆): δ = |
|---|---|---|---|
| 53 | 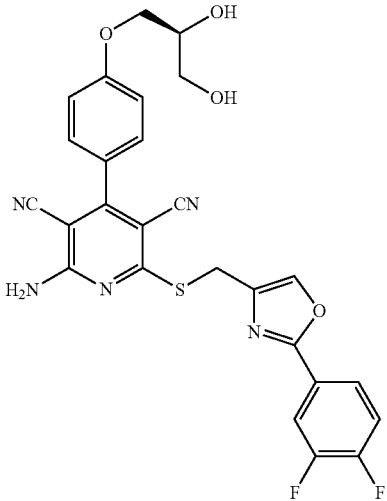 [SMILES: N#Cc1c(N)nc(SCc2coc(-c3ccc(F)c(F)c3)n2)c(C#N)c1-c1ccc(OC[C@@H](O)CO)cc1] (62% of theory) | 2.43 min (3); m/z = 536 | 8.39 (s, 1H), 8.32-7.91 (br. s, 2H), 7.97 (dd, 1H), 7.86-7.80 (m, 1H), 7.63 (q, 1H), 7.46 (d, 2H), 7.10 (d, 2H), 5.05-4.58 (2 br. s, 2H), 4.41 (s, 2H), 4.09 (dd, 1H), 3.95 (dd, 1H), 3.84-3.79 (m, 1H), 3.46 (d, 2H). |
| 54 | 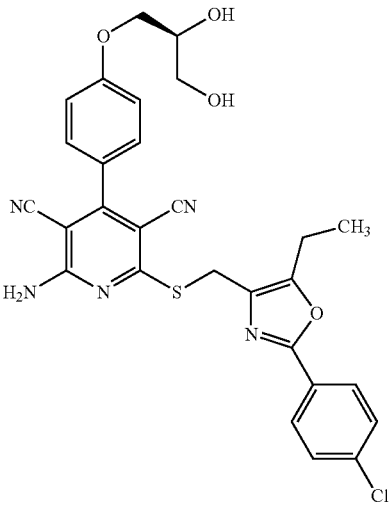 [SMILES: CCc1oc(-c2ccc(Cl)cc2)nc1CSc1nc(N)c(C#N)c(-c2ccc(OC[C@@H](O)CO)cc2)c1C#N] (74% of theory) | 2.68 min (3); m/z = 562 | 8.21-7.88 (br. s, 2H), 7.94 (d, 2H), 7.58 (d, 2H), 7.47 (d, 2H), 7.09 (d, 2H), 5.00 (d, 1H), 4.70 (t, 1H), 4.52 (s, 2H), 4.08 (dd, 1H), 3.98-3.92 (m, 1H), 3.86-3.77 (m, 1H), 3.47 (t, 2H), 2.88 (q, 2H), 1.19 (t, 3H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 55 | 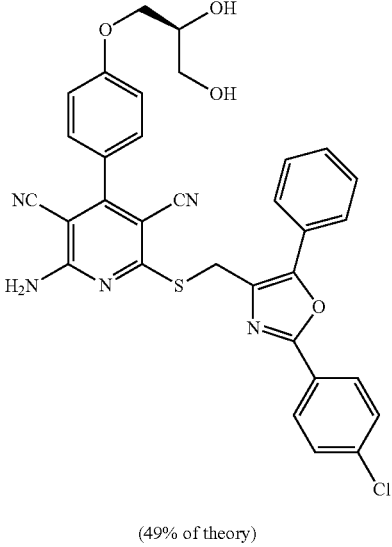<br>(49% of theory) | 2.48 min (6); m/z = 610 [M]$^+$ | 8.10 (d, 2H), 7.99-7.87 (br. s, 2H), 7.85 (d, 2H), 7.64 (d, 2H), 7.61-7.51 (m, 2H), 7.50-7.44 (m, 3H), 7.11 (d, 2H), 5.01 (d, 1H), 4.81 (s, 2H), 4.69 (t, 1H), 4.09 (dd, 1H), 3.96 (dd, 1H), 3.87-3.78 (m, 1H), 3.47 (t, 2H). |
| 56 | 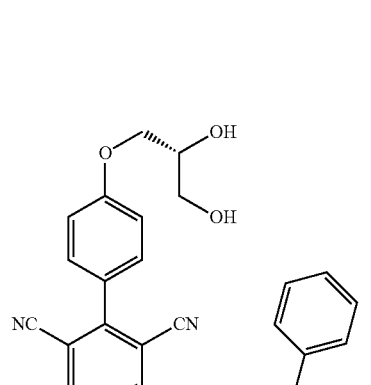<br>(67% of theory) | 2.48 min (6); m/z = 610 [M]$^+$ | 8.10 (d, 2H), 7.98-7.87 (br. s, 2H), 7.86 (d, 2H), 7.64 (d, 2H), 7.61-7.53 (m, 2H), 7.51-7.44 (m, 3H), 7.11 (d, 2H), 5.01 (d, 1H), 4.81 (s, 2H), 4.69 (t, 1H), 4.09 (dd, 1H), 3.96 (dd, 1H), 3.87-3.78 (m, 1H), 3.48 (t, 2H). |

TABLE 9-continued

| Example No. | Structure (Yield) | LC-MS: $R_t$ [min] (method); MS (ESI): m/z [M + H]+ | $^1$H-NMR (DMSO-$d_6$): δ = |
|---|---|---|---|
| 57 | (structure) (99% of theory) | 3.26 min (5); m/z = 572 | 8.17-7.98 (m, 6H), 7.49 (d, 2H), 7.10 (d, 2H), 5.00 (d, 1H), 4.70 (t, 1H), 4.53 (s, 2H), 4.08 (dd, 1H), 3.99-3.92 (m, 1H), 3.88 (s, 3H), 3.85-3.79 (m, 1H), 3.46 (t, 2H), 2.49 (s, 3H). |
| 58 | (structure) (79% of theory) | 2.58 min (3); m/z = 548 | 8.24-7.89 (br. s, 2H), 7.92 (d, 2H), 7.58 (d, 2H), 7.49 (d, 2H), 7.10 (d, 2H), 5.00 (d, 1H), 4.69 (t, 1H), 4.51 (s, 2H), 4.08 (dd, 1H), 3.95 (dd, 1H), 3.81 (q, 1H), 3.47 (t, 2H), 2.48 (s, 3H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 59 | 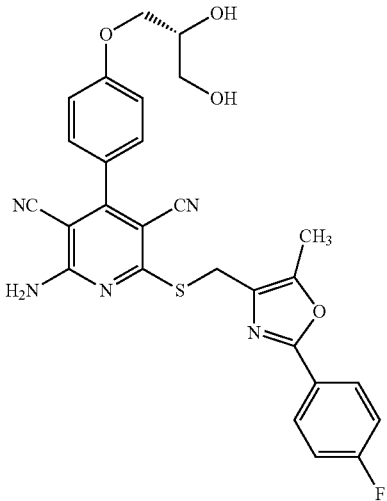 [SMILES: Cc1oc(-c2ccc(F)cc2)nc1CSc1nc(N)c(C#N)c(-c2ccc(OC[C@H](O)CO)cc2)c1C#N]<br>(72% of theory) | 2.42 min (3); m/z = 532 | 8.19-7.91 (br. s, 2H), 7.98 (d, 1H), 7.97 (d, 1H), 7.49 (d, 2H), 7.36 (pseudo-t, 2H), 7.10 (d, 2H), 4.50 (s, 2H), 4.10 (dd, 1H), 3.97 (dd, 1H), 3.81 (q, 1H), 3.71-3.26 (br. s, 2H), 3.47 (t, 2H), 2.47 (s, 3H). |
| 60 | 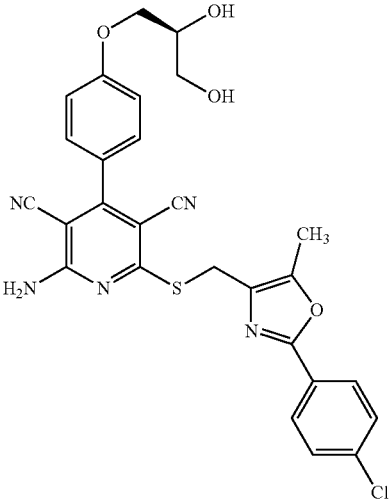 [SMILES: Cc1oc(-c2ccc(Cl)cc2)nc1CSc1nc(N)c(C#N)c(-c2ccc(OC[C@@H](O)CO)cc2)c1C#N]<br>(92% of theory) | 2.58 min (3); m/z = 548 | 8.27-7.96 (br. s, 2H), 7.93 (d, 2H), 7.58 (d, 2H), 7.49 (d, 2H), 7.10 (d, 2H), 5.00 (d, 1H), 4.70 (t, 1H), 4.51 (s, 2H), 4.09 (dd, 1H), 3.96 (dd, 1H), 3.84-3.78 (m, 1H), 3.47 (t, 2H), 2.49 (s, 3H). |

TABLE 9-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 61 | 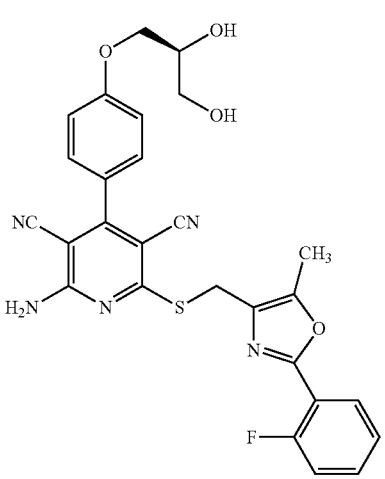 [SMILES: Cc1oc(-c2ccccc2F)nc1CSc1nc(N)c(C#N)c(-c2ccc(OC[C@@H](O)CO)cc2)c1C#N]<br>(70% of theory) | 1.79 min (7); m/z = 532 | 8.20-7.92 (br. s, 2H), 7.97 (dt, 1H), 7.60-7.53 (m, 1H), 7.48 (d, 2H), 7.43-7.31 (m, 2H), 7.09 (d, 2H), 5.00 (d, 1H), 4.70 (t, 1H), 4.53 (s, 2H), 4.09 (dd, 1H), 3.95 (dd, 1H), 3.72 (q, 1H), 3.47 (t, 2H), 2.47 (s, 3H). |
| 62 | 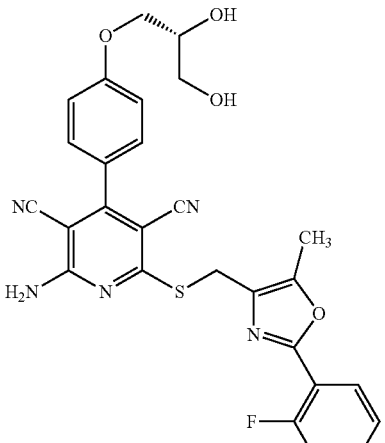<br>(62% of theory) | 1.79 min (7); m/z = 532 | 8.19-7.90 (br. s, 2H), 7.97 (dt, 1H), 7.60-7.53 (m, 1H), 7.49 (d, 2H), 7.43-7.32 (m, 2H), 7.10 (d, 2H), 5.00 (d, 1H), 4.69 (t, 1H), 4.52 (s, 2H), 4.09 (dd, 1H), 3.95 (dd, 1H), 3.71 (q, 1H), 3.47 (t, 2H), 2.47 (s, 3H). |

TABLE 9-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 63 | 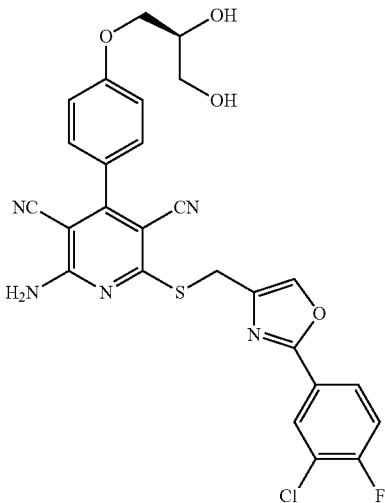 [SMILES: N#Cc1c(N)nc(SCc2coc(-c3ccc(F)c(Cl)c3)n2)c(C#N)c1-c1ccc(OC[C@@H](O)CO)cc1]<br>(74% of theory) | 2.54 min (3); m/z = 552 | 8.39 (s, 1H), 8.31-7.89 (br. s, 2H), 8.10 (dd, 1H), 8.00-7.94 (m, 1H), 7.60 (pseudo-t, 1H), 7.47 (d, 2H), 7.09 (d, 2H), 5.00 (d, 1H), 4.70 (t, 1H), 4.41 (s, 2H), 4.08 (dd, 1H), 3.95 (dd, 1H), 3.81 (q, 1H), 3.46 (t, 2H). |
| 64 | 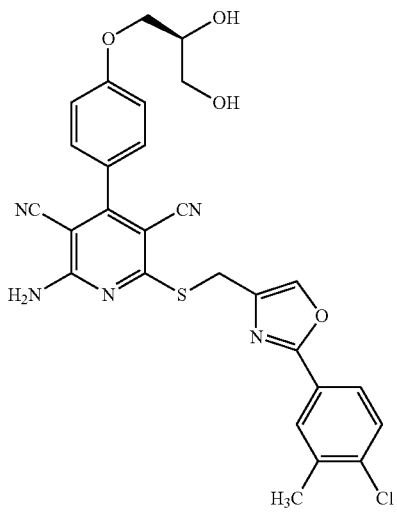 [SMILES: Cc1cc(-c2nc(CSc3nc(N)c(C#N)c(-c4ccc(OC[C@@H](O)CO)cc4)c3C#N)co2)ccc1Cl]<br>(99% of theory) | 2.64 min (3); m/z = 548 | 8.36 (s, 1H), 8.30-7.90 (br. s, 2H), 7.97 (s, 1H), 7.79 (dd, 1H), 7.57 (d, 1H), 7.46 (d, 2H), 7.09 (d, 2H), 5.00 (d, 1H), 4.69 (t, 1H), 4.42 (s, 2H), 4.09 (dd, 1H), 3.95 (dd, 1H), 3.86-3.77 (m, 1H), 3.47 (t, 2H), 2.41 (s, 3H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 65 | 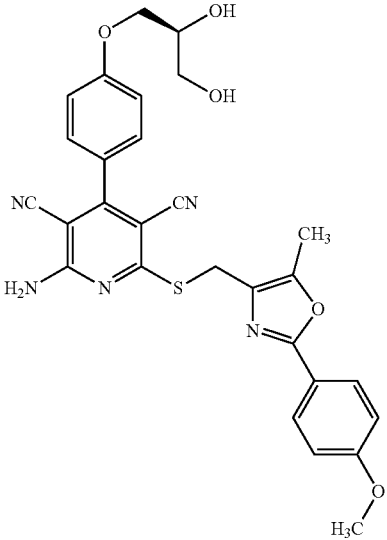 [SMILES: COc1ccc(-c2nc(CSc3nc(N)c(C#N)c(-c4ccc(OC[C@@H](O)CO)cc4)c3C#N)c(C)o2)cc1]<br>(48% of theory) | 2.39 min (3); m/z = 544 | 8.21-7.91 (br. s, 2H), 7.86 (d, 2H), 7.48 (d, 2H), 7.10 (d, 2H), 7.05 (d, 2H), 5.00 (d, 1H), 4.70 (t, 1H), 4.49 (s, 2H), 4.09 (dd, 1H), 3.95 (dd, 1H), 3.85-3.79 (m, 1H), 3.81 (s, 3H), 3.48 (t, 2H), 2.43 (s, 3H). |
| 66 | 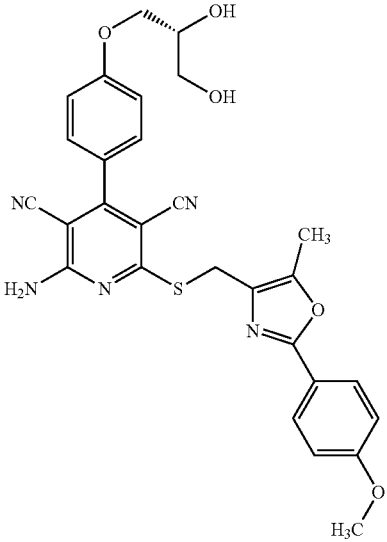 [SMILES: COc1ccc(-c2nc(CSc3nc(N)c(C#N)c(-c4ccc(OC[C@H](O)CO)cc4)c3C#N)c(C)o2)cc1]<br>(68% of theory) | 2.39 min (3); m/z = 544 | 8.18-7.94 (br. s, 2H), 7.86 (d, 2H), 7.49 (d, 2H), 7.10 (d, 2H), 7.07 (d, 2H), 5.00 (d, 1H), 4.70 (t, 1H), 4.49 (s, 2H), 4.09 (dd, 1H), 3.95 (dd, 1H), 3.85-3.79 (m, 1H), 3.83 (s, 3H), 3.47 (t, 2H), 2.45 (s, 3H). |

TABLE 9-continued
| Example No. | Structure (Yield) | LC-MS: $R_t$ [min] (method); MS (ESI): m/z [M + H]⁺ | ¹H-NMR (DMSO-d₆): δ = |
|---|---|---|---|
| 67 | 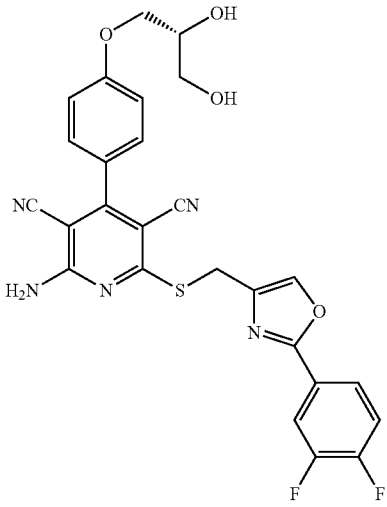 [SMILES: N#Cc1c(N)nc(SCc2coc(-c3ccc(F)c(F)c3)n2)c(C#N)c1-c1ccc(OC[C@H](O)CO)cc1] (51% of theory) | 2.02 min (6); m/z = 536 | 8.39 (s, 1H), 8.34-7.91 (br. s, 2H), 7.96 (dd, 1H), 7.86-7.80 (m, 1H), 7.63 (q, 1H), 7.47 (d, 2H), 7.09 (d, 2H), 5.00 (s, 1H), 4.70 (s, 1H), 4.41 (s, 2H), 4.09 (dd, 1H), 3.95 (dd, 1H), 3.84-3.78 (m, 1H), 3.45 (d, 2H). |
| 68 | 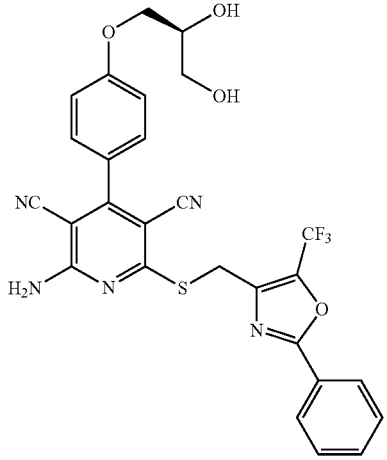 [SMILES: N#Cc1c(N)nc(SCc2nc(-c3ccccc3)oc2C(F)(F)F)c(C#N)c1-c1ccc(OC[C@@H](O)CO)cc1] (89% of theory) | 2.22 min (6); m/z = 568 | 8.09-7.93 (br. s, 2H), 8.04 (d, 2H), 7.68-7.57 (m, 3H), 7.50 (d, 2H), 7.11 (d, 2H), 5.00 (d, 1H), 4.71 (s, 2H), 4.70 (t, 1H), 4.09 (dd, 1H), 3.97 (dd, 1H), 3.87-3.79 (m, 1H), 3.47 (t, 2H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 69 | 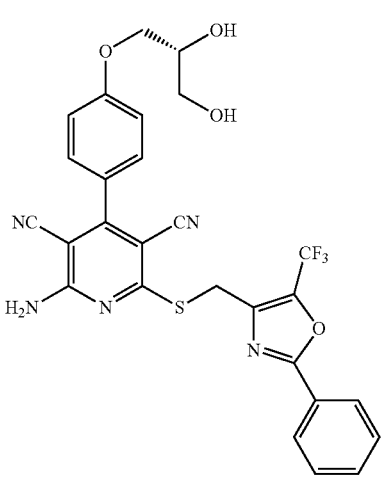 [SMILES: N#Cc1c(N)nc(SCc2nc(-c3ccccc3)oc2C(F)(F)F)c(C#N)c1-c1ccc(OC[C@H](O)CO)cc1] (93% of theory) | 2.22 min (6); m/z = 568 | 8.09-7.90 (br. s, 2H), 8.03 (d, 2H), 7.68-7.56 (m, 3H), 7.49 (d, 2H), 7.11 (d, 2H), 5.00 (d, 1H), 4.71 (s, 2H), 4.70 (t, 1H), 4.09 (dd, 1H), 3.97 (dd, 1H), 3.86-3.79 (m, 1H), 3.48 (t, 2H). |
| 70 | 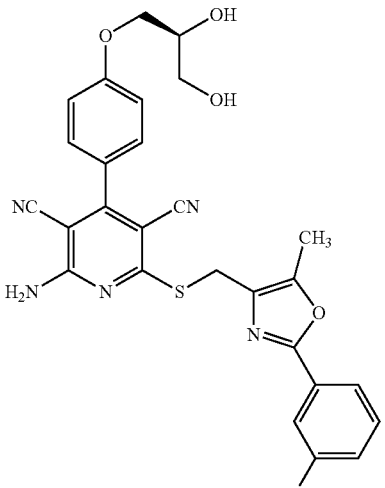 (88% of theory) | 2.05 min (6); m/z = 532 | 8.20-7.90 (br. s, 2H), 7.77 (d, 1H), 7.66 (dd, 1H), 7.58 (q, 1H), 7.49 (d, 2H), 7.38 (dt, 1H), 7.11 (d, 2H), 5.01 (d, 1H), 4.70 (t, 1H), 4.52 (s, 2H), 4.10 (dd, 1H), 3.96 (dd, 1H), 3.85-3.79 (m, 1H), 3.47 (t, 2H), 2.48 (s, 3H). |

TABLE 9-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 71 | 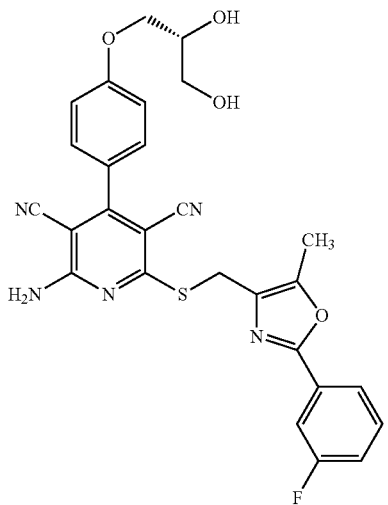 [SMILES: Cc1oc(-c2cccc(F)c2)nc1CSc1nc(N)c(C#N)c(-c2ccc(OC[C@H](O)CO)cc2)c1C#N]<br>(83% of theory) | 2.05 min (6); m/z = 532 | 8.19-7.92 (br. s, 2H), 7.77 (d, 1H), 7.65 (dd, 1H), 7.57 (q, 1H), 7.48 (d, 2H), 7.37 (dt, 1H), 7.10 (d, 2H), 5.00 (d, 1H), 4.70 (t, 1H), 4.52 (s, 2H), 4.09 (dd, 1H), 3.95 (dd, 1H), 3.86-3.78 (m, 1H), 3.47 (t, 2H), 2.48 (s, 3H). |
| 72 | 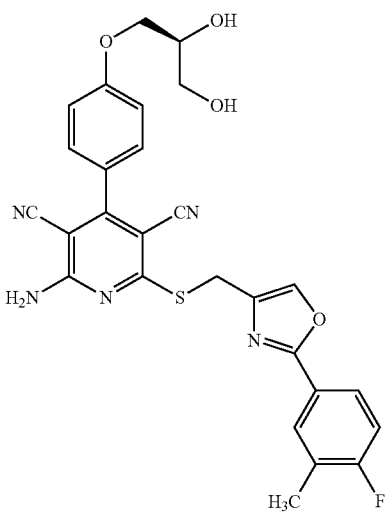 [SMILES: Cc1cc(-c2nc(CSc3nc(N)c(C#N)c(-c4ccc(OC[C@@H](O)CO)cc4)c3C#N)co2)ccc1F]<br>(88% of theory) | 2.49 min (3); m/z = 532 | 8.32 (s, 1H), 8.26-7.96 (br. s, 2H), 7.91 (d, 1H), 7.85-7.79 (m, 1H), 7.47 (d, 2H), 7.30 (t, 1H), 7.10 (d, 2H), 5.01 (d, 1H), 4.70 (t, 1H), 4.41 (s, 2H), 4.08 (dd, 1H), 3.95 (dd, 1H), 3.85-3.77 (m, 1H), 3.46 (t, 2H), 2.32 (s, 3H). |

TABLE 9-continued
| Example No. | Structure (Yield) | LC-MS: $R_t$ [min] (method); MS (ESI): m/z [M + H]+ | ¹H-NMR (DMSO-d₆): δ = |
|---|---|---|---|
| 73 | 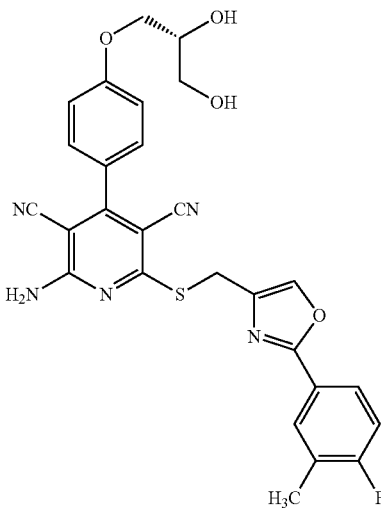 [SMILES: Cc1cc(-c2nc(CSc3nc(N)c(C#N)c(-c4ccc(OC[C@H](O)CO)cc4)c3C#N)co2)ccc1F]<br>(87% of theory) | 2.50 min (3); m/z = 532 | 8.32 (s, 1H), 8.27-7.97 (br. s, 2H), 7.91 (dd, 1H), 7.84-7.79 (m, 1H), 7.47 (d, 2H), 7.30 (t, 1H), 7.10 (d, 2H), 5.00 (d, 1H), 4.71 (t, 1H), 4.41 (s, 2H), 4.09 (dd, 1H), 3.95 (dd, 1H), 3.85-3.78 (m, 1H), 3.46 (t, 2H), 2.32 (s, 3H). |
| 74 | 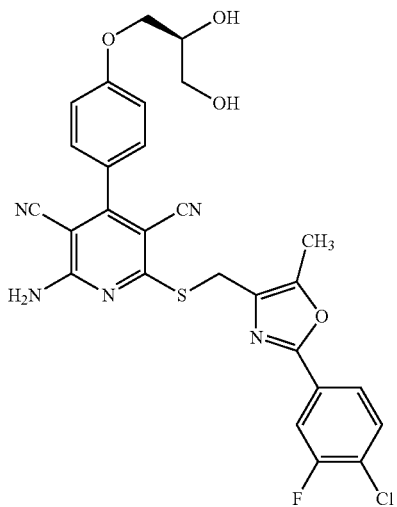 [SMILES: Cc1oc(-c2ccc(Cl)c(F)c2)nc1CSc1nc(N)c(C#N)c(-c2ccc(OC[C@@H](O)CO)cc2)c1C#N]<br>(47% of theory) | 2.04 min (7); m/z = 566 | 8.20-7.92 (br. s, 2H), 7.85 (d, 1H), 7.77 (s, 1H), 7.76 (q, 1H), 7.49 (d, 2H), 7.10 (d, 2H), 5.00 (d, 1H), 4.69 (t, 1H), 4.51 (s, 2H), 4.08 (dd, 1H), 3.95 (dd, 1H), 3.86-3.78 (m, 1H), 3.47 (t, 2H), 2.50 (s, 3H). |

TABLE 9-continued
| Example No. | Structure (Yield) | LC-MS: R$_t$ [min] (method); MS (ESI): m/z [M + H]$^+$ | $^1$H-NMR (DMSO-d$_6$): δ = |
|---|---|---|---|
| 75 | 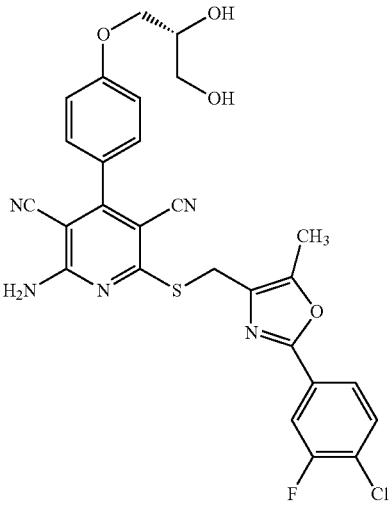 [SMILES: Cc1oc(-c2ccc(Cl)c(F)c2)nc1CSc1nc(N)c(C#N)c(-c2ccc(OC[C@H](O)CO)cc2)c1C#N] (66% of theory) | 2.05 min (7); m/z = 566 | 8.22-7.95 (br. s, 2H), 7.86 (d, 1H), 7.78 (s, 1H), 7.77 (q, 1H), 7.49 (d, 2H), 7.11 (d, 2H), 5.00 (d, 1H), 4.70 (t, 1H), 4.52 (s, 2H), 4.09 (dd, 1H), 3.97 (dd, 1H), 3.86-3.78 (m, 1H), 3.47 (t, 2H), 2.50 (s, 3H). |
| 76 | 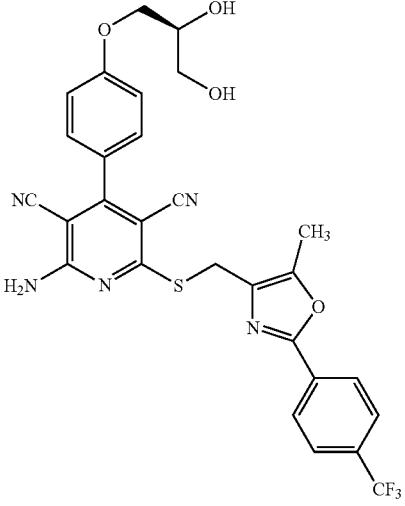 [SMILES: Cc1oc(-c2ccc(C(F)(F)F)cc2)nc1CSc1nc(N)c(C#N)c(-c2ccc(OC[C@@H](O)CO)cc2)c1C#N] (84% of theory) | 2.57 min (3); m/z = 582 | 8.18-7.96 (br. s, 2H), 8.12 (d, 2H), 7.88 (d, 2H), 7.49 (d, 2H), 7.10 (d, 2H), 5.00 (d, 1H), 4.69 (t, 1H), 4.53 (s, 2H), 4.09 (dd, 1H), 3.95 (dd, 1H), 3.85-3.78 (m, 1H), 3.47 (t, 2H), 2.49 (s, 3H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 77 | 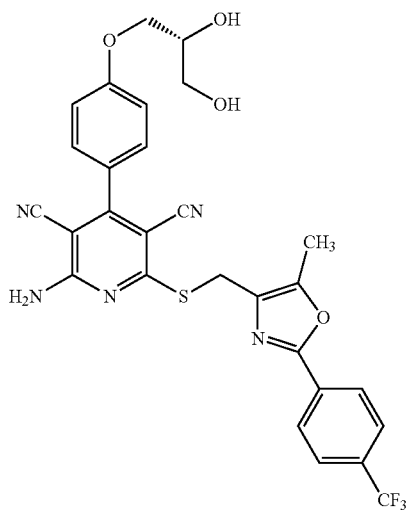 [SMILES: Cc1oc(-c2ccc(C(F)(F)F)cc2)nc1CSc1nc(N)c(C#N)c(-c2ccc(OC[C@H](O)CO)cc2)c1C#N] (70% of theory) | 2.58 min (3); m/z = 582 | 8.18-7.97 (br. s, 2H), 8.13 (d, 2H), 7.88 (d, 2H), 7.49 (d, 2H), 7.10 (d, 2H), 5.00 (d, 1H), 4.69 (t, 1H), 4.53 (s, 2H), 4.09 (dd, 1H), 3.95 (dd, 1H), 3.85-3.78 (m, 1H), 3.47 (t, 2H), 2.49 (s, 3H). |
| 78 | 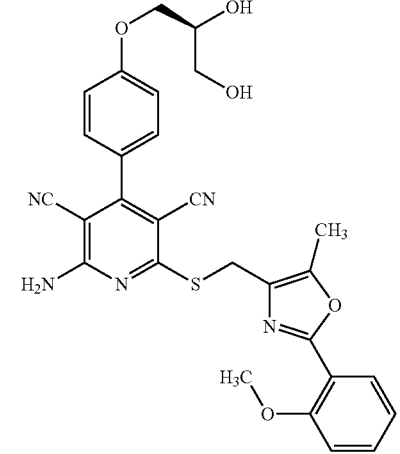 [SMILES: COc1ccccc1-c1nc(CSc2nc(N)c(C#N)c(-c3ccc(OC[C@@H](O)CO)cc3)c2C#N)c(C)o1] (62% of theory) | 1.10 min (14); m/z = 544 | 8.22-7.95 (br. s, 2H), 7.76 (dd, 1H), 7.53-7.45 (m, 1H), 7.49 (d, 2H), 7.20 (d, 1H), 7.10 (d, 2H), 7.05 (t, 1H), 5.02 (d, 1H), 4.71 (t, 1H), 4.51 (s, 2H), 4.09 (dd, 1H), 3.95 (dd, 1H), 3.89-3.78 (m, 1H), 3.86 (s, 3H), 3.50-3.42 (m, 2H), 2.43 (s, 3H). |

TABLE 9-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 79 | 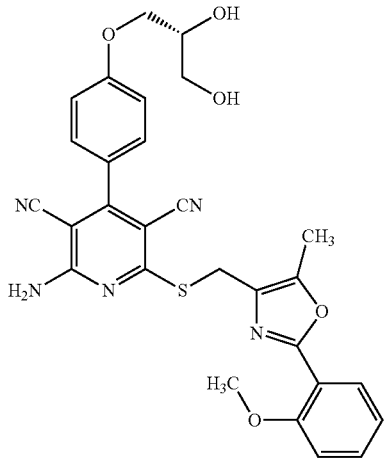 [SMILES: COc1ccccc1-c1nc(CSc2nc(N)c(C#N)c(-c3ccc(OC[C@H](O)CO)cc3)c2C#N)c(C)o1] (85% of theory) | 1.10 min (14); m/z = 544 | 8.18-7.96 (br. s, 2H), 7.76 (dd, 1H), 7.52-7.44 (m, 1H), 7.49 (d, 2H), 7.19 (d, 1H), 7.10 (d, 2H), 7.05 (t, 1H), 5.02 (d, 1H), 4.71 (t, 1H), 4.51 (s, 2H), 4.09 (dd, 1H), 3.95 (dd, 1H), 3.88-3.78 (m, 1H), 3.86 (s, 3H), 3.46 (t, 2H), 2.43 (s, 3H). |
| 80 | 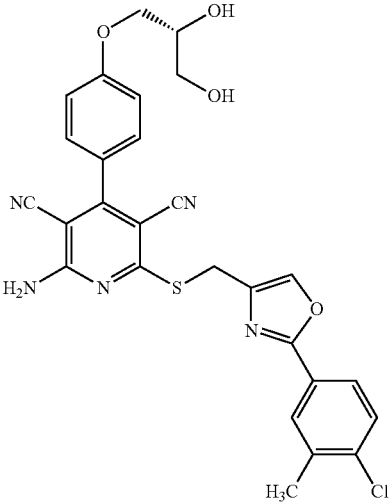 [SMILES: Cc1cc(-c2nc(CSc3nc(N)c(C#N)c(-c4ccc(OC[C@H](O)CO)cc4)c3C#N)co2)ccc1Cl] (80% of theory) | 2.67 min (3); m/z = 548 | 8.36 (s, 1H), 8.27-7.98 (br. s, 2H), 7.97 (s, 1H), 7.79 (dd, 1H), 7.57 (d, 1H), 7.46 (d, 2H), 7.10 (d, 2H), 5.00 (d, 1H), 4.69 (t, 1H), 4.42 (s, 2H), 4.09 (dd, 1H), 3.96 (dd, 1H), 3.86-3.78 (m, 1H), 3.47 (t, 2H), 2.41 (s, 3H). |

TABLE 9-continued
| Example No. | Structure (Yield) | LC-MS: R_t [min] (method); MS (ESI): m/z [M + H]+ | $^1$H-NMR (DMSO-d$_6$): δ = |
|---|---|---|---|
| 81 | 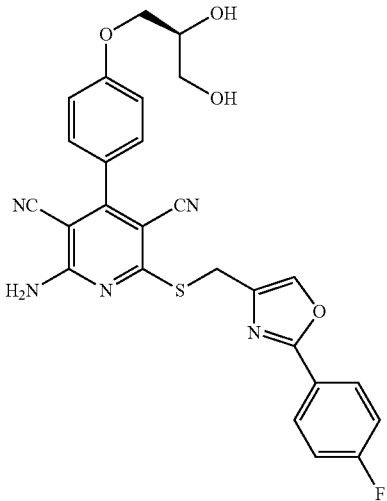 [SMILES: N#Cc1c(N)nc(SCc2coc(-c3ccc(F)cc3)n2)c(C#N)c1-c1ccc(OC[C@@H](O)CO)cc1] (83% of theory) | 2.38 min (3); m/z = 518 | 8.34 (s, 1H), 8.27-7.91 (br. s, 2H), 8.01 (dd, 2H), 7.46 (d, 2H), 7.38 (t, 2H), 7.10 (d, 2H), 5.00 (d, 1H), 4.70 (t, 1H), 4.42 (s, 2H), 4.08 (dd, 1H), 3.96 (dd, 1H), 3.85-3.77 (m, 1H), 3.47 (t, 2H). |
| 82 | 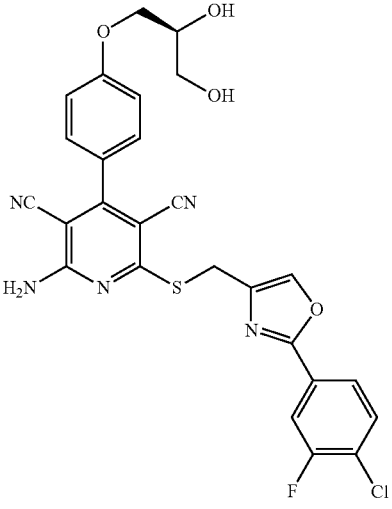 [SMILES: N#Cc1c(N)nc(SCc2coc(-c3ccc(Cl)c(F)c3)n2)c(C#N)c1-c1ccc(OC[C@@H](O)CO)cc1] (78% of theory) | 2.44 min (3); m/z = 552 | 8.41 (s, 1H), 8.31-7.96 (br. s, 2H), 7.91 (dd, 1H), 7.84-7.73 (m, 2H), 7.46 (d, 2H), 7.09 (d, 2H), 5.00 (d, 1H), 4.69 (t, 1H), 4.52 (s, 2H), 4.08 (dd, 1H), 3.95 (dd, 1H), 3.86-3.78 (m, 1H), 3.48 (t, 2H). |

TABLE 9-continued
| Example No. | Structure (Yield) | LC-MS: R_t [min] (method); MS (ESI): m/z [M + H]+ | $^1$H-NMR (DMSO-d$_6$): δ = |
|---|---|---|---|
| 83 | 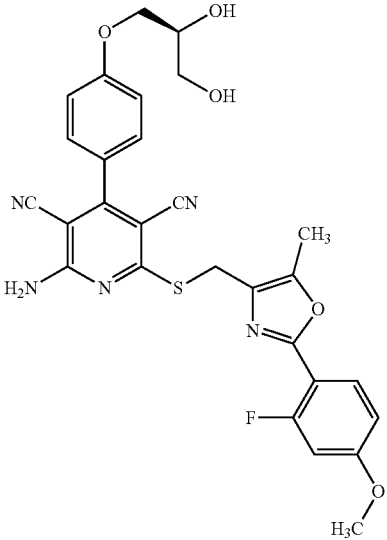 [SMILES: COc1ccc(-c2nc(CSc3nc(N)c(C#N)c(-c4ccc(OC[C@@H](O)CO)cc4)c3C#N)c(C)o2)c(F)c1]<br>(80% of theory) | 2.28 min (3); m/z = 562 | 8.15-7.96 (br. s, 2H), 7.87 (t, 1H), 7.49 (d, 2H), 7.10 (d, 2H), 7.01 (dd, 1H), 6.92 (dd, 1H), 5.00 (d, 1H), 4.69 (t, 1H), 4.51 (s, 2H), 4.09 (dd, 1H), 3.96 (dd, 1H), 3.86-3.78 (m, 1H), 3.84 (s, 3H), 3.47 (t, 2H), 2.45 (s, 3H). |
| 84 | 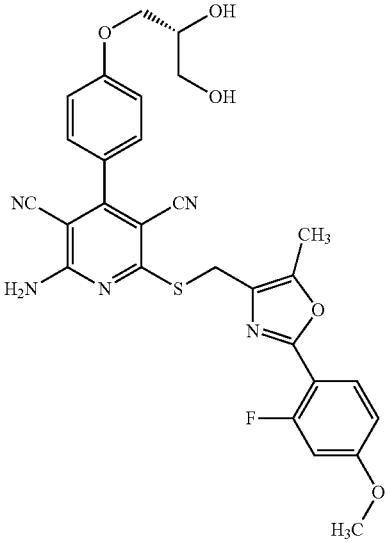 [SMILES: COc1ccc(-c2nc(CSc3nc(N)c(C#N)c(-c4ccc(OC[C@H](O)CO)cc4)c3C#N)c(C)o2)c(F)c1]<br>(62% of theory) | 2.28 min (3); m/z = 562 | 8.14-7.95 (br. s, 2H), 7.87 (t, 1H), 7.49 (d, 2H), 7.10 (d, 2H), 7.01 (dd, 1H), 6.92 (dd, 1H), 5.00 (d, 1H), 4.70 (t, 1H), 4.51 (s, 2H), 4.09 (dd, 1H), 3.96 (dd, 1H), 3.86-3.78 (m, 1H), 3.84 (s, 3H), 3.47 (t, 2H), 2.45 (s, 3H). |

TABLE 9-continued
| Example No. | Structure (Yield) | LC-MS: $R_t$ [min] (method); MS (ESI): m/z [M + H]⁺ | ¹H-NMR (DMSO-d₆): δ = |
|---|---|---|---|
| 85 | 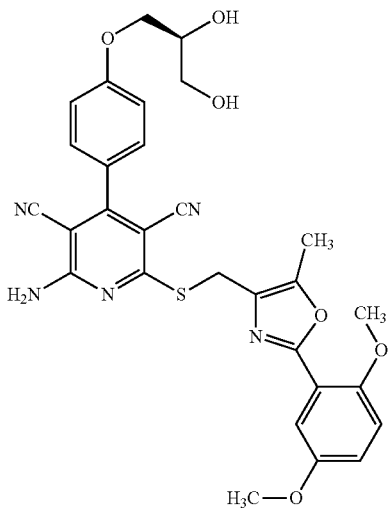 [SMILES: COc1ccc(OC)c(-c2nc(CSc3nc(N)c(C#N)c(-c4ccc(OC[C@@H](O)CO)cc4)c3C#N)c(C)o2)c1]<br>(57% of theory) | 2.19 min (3); m/z = 574 | 8.14-7.97 (br. s, 2H), 7.49 (d, 2H), 7.29 (d, 1H), 7.15-7.09 (t, 3H), 7.06 (dd, 1H), 5.00 (d, 1H), 4.69 (t, 1H), 4.51 (d, 2H), 4.09 (dd, 1H), 3.96 (dd, 1H), 3.87-3.79 (m, 1H), 3.81 (s, 3H), 3.76 (s, 3H), 3.48 (t, 2H), 2.44 (s, 3H). |
| 86 | 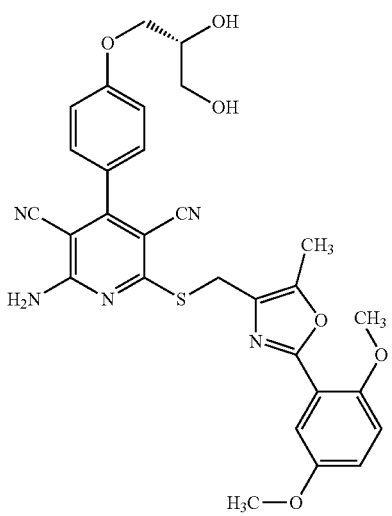 [SMILES: COc1ccc(OC)c(-c2nc(CSc3nc(N)c(C#N)c(-c4ccc(OC[C@H](O)CO)cc4)c3C#N)c(C)o2)c1]<br>(63% of theory) | 2.19 min (3); m/z = 574 | 8.13-7.97 (br. s, 2H), 7.49 (d, 2H), 7.29 (d, 1H), 7.15-7.09 (m, 3H), 7.05 (dd, 1H), 5.00 (d, 1H), 4.70 (t, 1H), 4.51 (d, 2H), 4.09 (dd, 1H), 3.96 (dd, 1H), 3.87-3.79 (m, 1H), 3.80 (s, 3H), 3.76 (s, 3H), 3.47 (t, 2H), 2.45 (s, 3H). |

TABLE 9-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 87 | 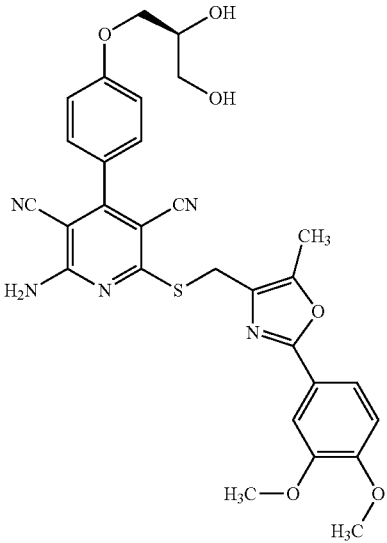 [SMILES: COc1ccc(-c2nc(CSc3nc(N)c(C#N)c(-c4ccc(OC[C@@H](O)CO)cc4)c3C#N)c(C)o2)cc1OC]<br>(51% of theory) | 1.69 min (7); m/z = 574 | 8.15-7.98 (br. s, 2H), 7.49 (d, 2H), 7.48 (d, 1H), 7.40 (s, 1H), 7.11 (d, 2H), 7.08 (d, 1H), 5.00 (d, 1H), 4.70 (t, 1H), 4.50 (s, 2H), 4.09 (dd, 1H), 3.96 (dd, 1H), 3.85 (s, 3H), 3.83 (s, 3H), 3.83-3.78 (m, 1H), 3.47 (t, 2H), 2.46 (s, 3H). |
| 88 | 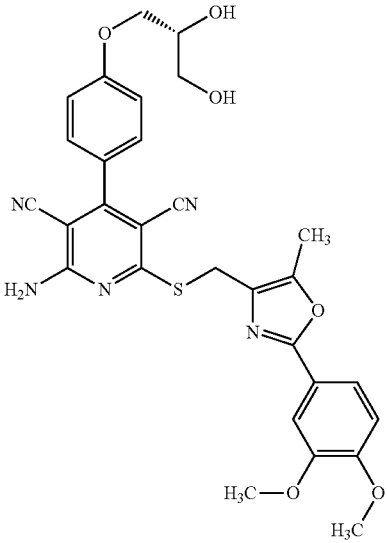 [SMILES: COc1ccc(-c2nc(CSc3nc(N)c(C#N)c(-c4ccc(OC[C@H](O)CO)cc4)c3C#N)c(C)o2)cc1OC]<br>(63% of theory) | 1.68 min (7); m/z = 574 | 8.17-7.98 (br. s, 2H), 7.49 (d, 2H), 7.48 (d, 1H), 7.40 (s, 1H), 7.11 (d, 2H), 7.09 (d, 1H), 5.00 (d, 1H), 4.70 (t, 1H), 4.50 (s, 2H), 4.09 (dd, 1H), 3.96 (dd, 1H), 3.84 (s, 3H), 3.82 (s, 3H), 3.82-3.78 (m, 1H), 3.47 (t, 2H), 2.46 (s, 3H). |

TABLE 9-continued

| Example No. | Structure (Yield) | LC-MS: R_t [min] (method); MS (ESI): m/z [M + H]+ | $^1$H-NMR (DMSO-$d_6$): δ = |
|---|---|---|---|
| 89 | (80% of theory) | 2.61 min (3); m/z = 564 | 8.52 (s, 1H), 8.18-7.95 (br. s, 2H), 8.14-8.07 (m, 1H), 8.03 (s, 2H), 8.00-7.95 (m, 1H), 7.59 (d, 2H), 7.48 (d, 2H), 7.10 (d, 2H), 5.00 (d, 1H), 4.70 (t, 1H), 4.54 (s, 2H), 4.09 (dd, 1H), 3.95 (dd, 1H), 3.85-3.78 (m, 1H), 3.47 (t, 2H), 2.50 (s, 3H). |
| 90 | (85% of theory) | 2.61 min (3); m/z = 564 | 8.52 (s, 1H), 8.20-7.94 (br. s, 2H), 8.13-8.07 (m, 1H), 8.04 (s, 2H), 8.00-7.94 (m, 1H), 7.62-7.57 (m, 2H), 7.49 (d, 2H), 7.10 (d, 2H), 5.00 (d, 1H), 4.70 (t, 1H), 4.55 (s, 2H), 4.09 (dd, 1H), 3.95 (dd, 1H), 3.86-3.78 (m, 1H), 3.46 (t, 2H), 2.50 (s, 3H). |

TABLE 9-continued
| Example No. | Structure (Yield) | LC-MS: $R_t$ [min] (method); MS (ESI): m/z [M + H]+ | $^1$H-NMR (DMSO-$d_6$): δ = |
|---|---|---|---|
| 91 | 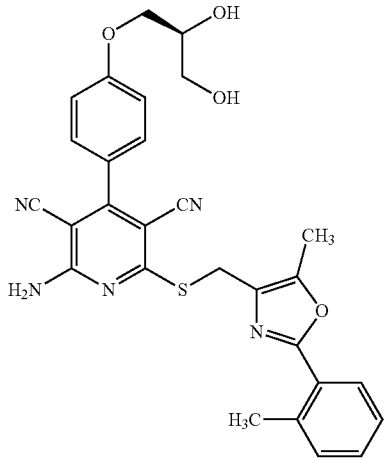 [SMILES: Cc1ccccc1-c1nc(CSc2nc(N)c(C#N)c(-c3ccc(OC[C@@H](O)CO)cc3)c2C#N)c(C)o1] (80% of theory) | 1.95 min (7); m/z = 528 | 8.18-7.95 (br. s, 2H), 7.86 (d, 1H), 7.48 (d, 2H), 7.41-7.29 (m, 3H), 7.10 (d, 2H), 5.01 (d, 1H), 4.70 (t, 1H), 4.52 (s, 2H), 4.10 (dd, 1H), 3.95 (dd, 1H), 3.85-3.78 (m, 1H), 3.48 (t, 2H), 2.60 (s, 3H), 2.47 (s, 3H). |
| 92 | 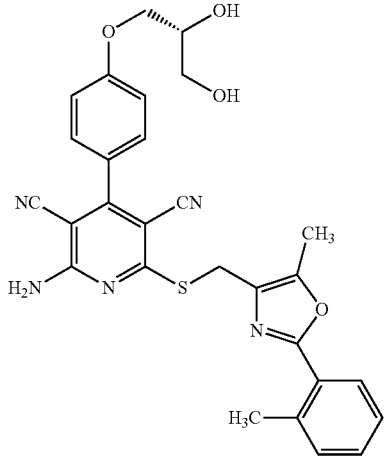 [SMILES: Cc1ccccc1-c1nc(CSc2nc(N)c(C#N)c(-c3ccc(OC[C@H](O)CO)cc3)c2C#N)c(C)o1] (77% of theory) | 1.95 min (7); m/z = 528 | 8.17-7.94 (br. s, 2H), 7.86 (d, 1H), 7.49 (d, 2H), 7.41-7.30 (m, 3H), 7.11 (d, 2H), 5.01 (d, 1H), 4.70 (t, 1H), 4.52 (s, 2H), 4.09 (dd, 1H), 3.95 (dd, 1H), 3.85-3.78 (m, 1H), 3.47 (t, 2H), 2.60 (s, 3H), 2.48 (s, 3H). |

TABLE 9-continued

| Example No. | Structure (Yield) | LC-MS: $R_t$ [min] (method); MS (ESI): m/z [M + H]+ | $^1$H-NMR (DMSO-$d_6$): δ = |
|---|---|---|---|
| 93 | 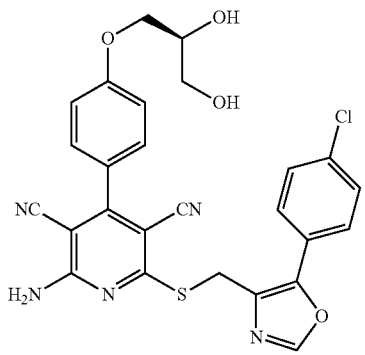 [SMILES: N#Cc1c(N)nc(SCc2ncoc2-c2ccc(Cl)cc2)c(C#N)c1-c1ccc(OC[C@@H](O)CO)cc1]<br>(41% of theory) | 2.15 min (15); m/z = 534 | 8.51 (s, 1H), 8.04-7.89 (br. s, 2H), 7.74 (d, 2H), 7.61 (d, 2H), 7.50 (d, 2H), 7.10 (d, 2H), 5.00 (d, 1H), 4.75 (s, 2H), 4.69 (t, 1H), 4.09 (dd, 1H), 3.97 (dd, 1H), 3.87-3.78 (m, 1H), 3.48 (t, 2H). |
| 94 | 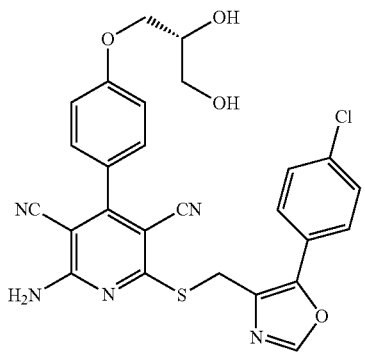 [SMILES: N#Cc1c(N)nc(SCc2ncoc2-c2ccc(Cl)cc2)c(C#N)c1-c1ccc(OC[C@H](O)CO)cc1]<br>(71% of theory) | 2.15 min (15); m/z = 534 | 8.51 (s, 1H), 8.04-7.89 (br. s, 2H), 7.74 (d, 2H), 7.61 (d, 2H), 7.49 (d, 2H), 7.11 (d, 2H), 5.00 (d, 1H), 4.75 (s, 2H), 4.69 (t, 1H), 4.09 (dd, 1H), 3.96 (dd, 1H), 3.86-3.78 (m, 1H), 3.47 (t, 2H). |

Example 95

4-{4-[({6-Amino-3,5-dicyano-4-[4-(2-hydroxy-2-methylpropoxy)phenyl]pyridin-2-yl}thio)-methyl]-5-methyl-1,3-oxazol-2-yl}benzoic acid

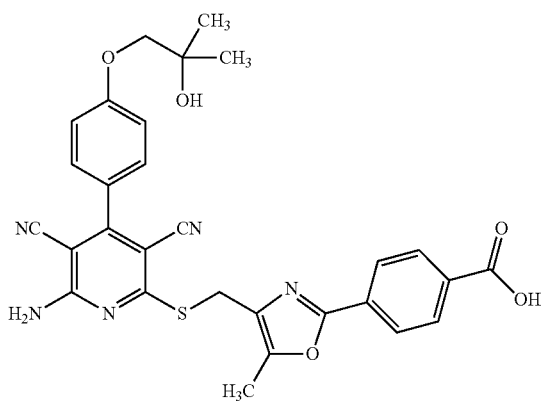 [SMILES: Cc1oc(-c2ccc(C(=O)O)cc2)nc1CSc1nc(N)c(C#N)c(-c2ccc(OCC(C)(C)O)cc2)c1C#N]

40 mg (0.07 mmol) of the compound from Example 17 and 11 mg (0.28 mmol) of sodium hydroxide are dissolved in 12.8 ml of 1,2-dimethoxyethane, 0.7 ml of methanol and 2.8 ml of water. The reaction solution is stirred at RT for 3 h. The mixture is then concentrated on a rotary evaporator. 5 ml of water are added to the residue. By addition of 1 N hydrochloric acid, the pH is adjusted to 4. The resulting precipitate is filtered off and purified by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 19 mg (47% of theory)

$^1$H-NMR (400 MHz, DMSO-$d_6$): δ=13.19 (s, 1H), 8.23-7.96 (br. s, 2H), 8.09-8.02 (m, 4H), 7.48 (d, 2H), 7.10 (d, 2H), 4.69 (s, 1H), 4.53 (s, 2H), 3.80 (s, 2H), 2.50 (s, 3H), 1.21 (s, 6H).

LC-MS (method 3): $R_t$=2.41 min; MS (ESIpos): m/z=556 [M+H]+.

The examples listed in Table 10 are prepared analogously to Example 95 from the appropriate starting materials:
TABLE 10
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 96 | 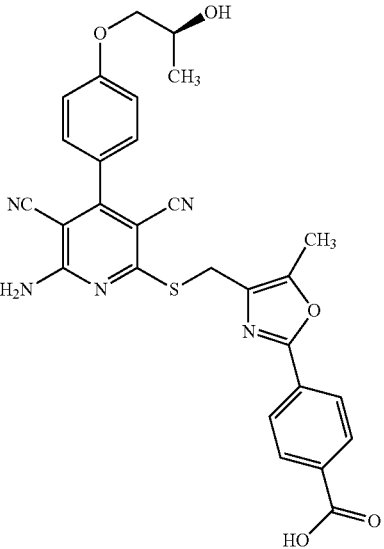 (15% of theory) | 2.32 min (3); m/z = 542 | 13.20 (s, 1H), 8.18-7.98 (br. s, 2H), 8.08-8.01 (m, 4H), 7.48 (d, 2H), 7.09 (d, 2H), 4.92 (d, 1H), 4.53 (s, 2H), 4.02-3.94 (m, 1H), 3.93-3.86 (m, 2H), 2.49 (s, 3H), 1.18 (d, 3H). |
| 97 | 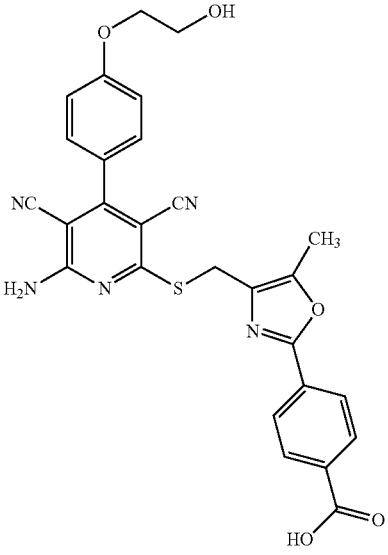 (15% of theory) | 1.73 min (17) | 13.19 (s, 1H), 8.29-7.95 (br. s, 2H), 8.10-7.99 (m, 4H), 7.48 (d, 2H), 7.10 (d, 2H), 4.95-4.88 (m, 1H), 4.52 (s, 2H), 4.08 (t, 2H), 3.78-3.70 (m, 2H), 2.48 (s, 3H). |

Example 98

4-[4-({[6-Amino-3,5-dicyano-4-(4-{[(2S)-2,3-dihydroxypropyl]oxy}phenyl)pyridin-2-yl]thio}-methyl)-5-methyl-1,3-oxazol-2-yl]benzoic acid

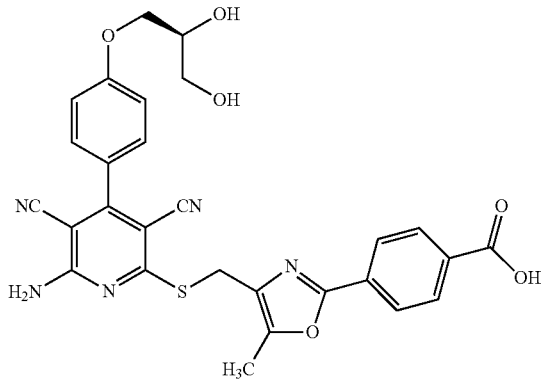 [SMILES: Cc1oc(-c2ccc(C(=O)O)cc2)nc1CSc1nc(N)c(C#N)c(-c2ccc(OC[C@@H](O)CO)cc2)c1C#N]

63 mg (0.11 mmol) of the compound from Example 57 are dissolved in 3 ml of THF, and 220 µl (0.22 mmol) of a 1 M aqueous lithium hydroxide solution are added. In a microwave, the reaction mixture is heated to 140° C., and the mixture is stirred at this temperature for 15 min. The solvent is then removed on a rotary evaporator. The residue is taken up in 3 ml of water and adjusted to pH 4 using about 0.5 ml of 1 N hydrochloric acid. A precipitate is formed, which is filtered off and purified by preparative HPLC (column: YMC GEL ODS-AQ S-5/15 nm; mobile phase gradient: acetonitrile/water 10:90→95:5). After removal of the solvent on a rotary evaporator, the product is obtained as a white solid.

Yield: 3 mg (5% of theory)

$^1$H-NMR (400 MHz, DMSO-$d_6$): δ=13.19 (br. s, 1H), 8.19-7.91 (m, 6H), 7.49 (d, 2H), 7.11 (d, 2H), 5.00 (d, 1H), 4.70 (t, 1H), 4.53 (s, 2H), 4.09 (dd, 1H), 3.95 (dd, 1H), 3.82 (q, 1H), 3.46 (t, 2H), 2.50 (s, 3H).

LC-MS (method 11): $R_t$=1.56 min; MS (ESIpos): m/z=558 [M+H]$^+$.

Example 99

2-Amino-4-(4-{[(2S)-2,3-dihydroxypropyl]oxy}phenyl)-6-({[2-(3-fluorophenyl)-1,3-oxazol-4-yl]-methyl}thio)pyridine-3,5-dicarbonitrile

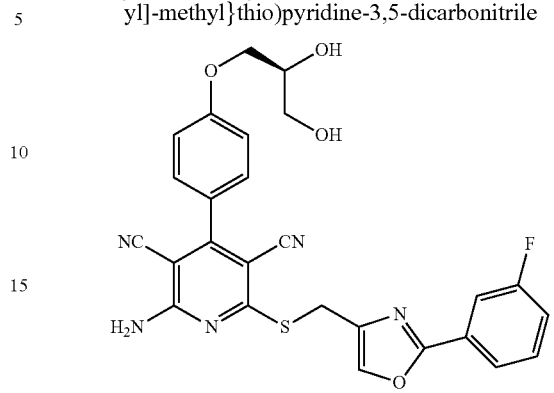

75 mg (0.17 mmol) of the compound from Example 10A and 38 mg (0.18 mmol) of the compound from Example 21A are dissolved in 2 ml of dry DMF, 50 mg (0.36 mmol) of potassium carbonate are added and the mixture is stirred at RT for 8 h. 0.82 ml (1.65 mmol) of 2 N hydrochloric acid are then added dropwise, and the mixture is stirred at RT for another 1 h. After filtration, the solvent is removed on a rotary evaporator. The residue is purified by preparative HPLC (column: YMC GEL ODS-AQ S-5/15 nm; mobile phase gradient: acetonitrile/water 10:90→95:5). After removal of the solvent on a rotary evaporator, the product is obtained as a white solid.

Yield: 17 mg (20% of theory)

$^1$H-NMR (400 MHz, DMSO-$d_6$): δ=8.39 (s, 1H), 8.27-7.89 (br. s, 2H), 7.81 (d, 1H), 7.70 (d, 1H), 7.59 (q, 1H), 7.46 (d, 2H), 7.39 (dt, 1H), 7.09 (d, 2H), 5.00 (d, 1H), 4.69 (t, 1H), 4.42 (s, 2H), 4.09 (dd, 1H), 3.94 (dd, 1H), 3.81 (q, 1H), 3.47 (t, 2H).

LC-MS (method 2): $R_t$=2.06 min; MS (ESIpos): m/z=518 [M+H]$^+$.

The examples listed in Table 11 are prepared analogously to Example 99 from the appropriate starting materials:

TABLE 11

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 100 | (23% of theory) | 2.39 min (10); m/z = 518 | 8.38 (s, 1H), 8.29-7.90 (br. s, 2H), 7.81 (d, 1H), 7.71 (d, 1H), 7.59 (q, 1H), 7.48 (d, 2H), 7.40 (dt, 1H), 7.09 (d, 2H), 5.00 (d, 1H), 4.69 (t, 1H), 4.42 (s, 2H), 4.08 (dd, 1H), 3.94 (dd, 1H), 3.81 (q, 1H), 3.46 (t, 2H). |

| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 101 | 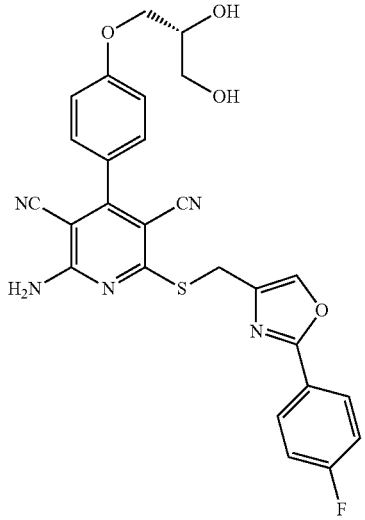<br>(39% of theory) | 2.08 min (2); m/z = 518 | 8.33 (s, 1H), 8.27-7.93 (br. s, 2H), 8.03 (d, 1H), 8.01 (d, 1H), 7.48 (d, 2H), 7.38 (t, 2H), 7.10 (d, 2H), 5.00 (d, 1H), 4.70 (t, 1H), 4.42 (s, 2H), 4.09 (dd, 1H), 3.96 (dd, 1H), 3.87-3.78 (m, 1H), 3.47 (t, 2H). |
| 102 | 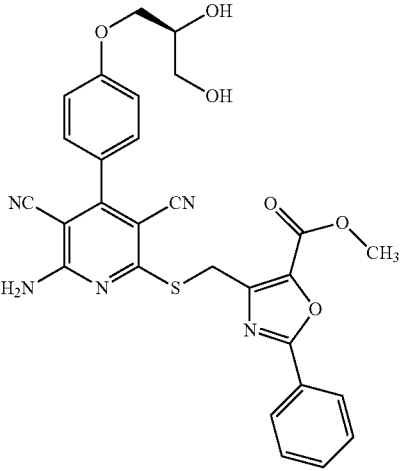<br>(58% of theory) | 1.83 min (7); m/z = 558 | 8.09-7.94 (br. s, 2H), 8.05 (d, 2H), 7.68-7.57 (m, 3H), 7.50 (d, 2H), 7.11 (d, 2H), 5.01 (d, 1H), 4.83 (s, 2H), 4.70 (t, 1H), 4.10 (dd, 1H), 3.99-3.91 (m, 1H), 3.93 (s, 3H), 3.86-3.78 (m, 1H), 3.47 (t, 2H). |

TABLE 11-continued

| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 103 | 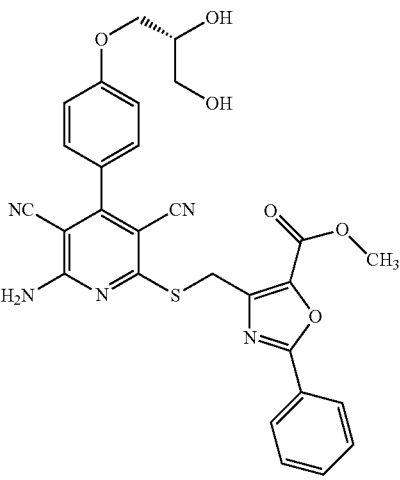<br>(68% of theory) | 1.84 min (7); m/z = 558 | 8.08-7.93 (br. s, 2H), 8.05 (d, 2H), 7.67-7.57 (m, 3H), 7.50 (d, 2H), 7.11 (d, 2H), 5.01 (d, 1H), 4.82 (s, 2H), 4.70 (t, 1H), 4.10 (dd, 1H), 3.99-3.91 (m, 1H), 3.93 (s, 3H), 3.85-3.79 (m, 1H), 3.47 (t, 2H). |

Example 104

2-Amino-6-({[2-(4-fluorophenyl)-5-methyl-1,3-oxazol-4-yl]methyl}thio)-4-(4-{[(2S)-2-hydroxypropyl]oxy}phenyl)pyridine-3,5-dicarbonitrile

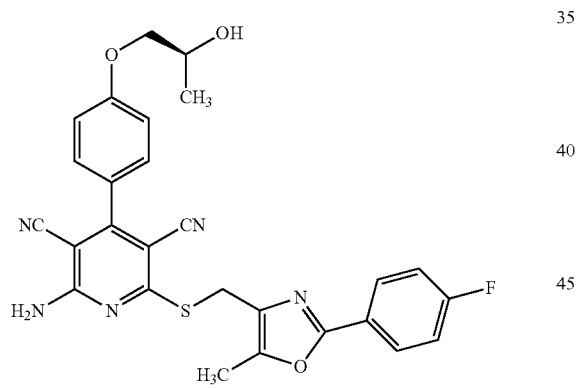

65 mg (0.10 mmol) of the compound from Example 95A are dissolved in 4 ml of methanol, and 1.5 ml of 1 N hydrochloric acid are added. The mixture is stirred at RT for 12 h. The solvent is then removed on a rotary evaporator, and the residue is purified by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 48 mg (91% of theory)

$^1$H-NMR (400 MHz, DMSO-d$_6$): δ=8.20-7.91 (br. s, 2H), 7.49 (d, 2H), 7.35 (pseudo-t, 2H), 7.09 (d, 2H), 4.91 (d, 1H), 4.50 (s, 2H), 4.02-3.94 (m, 1H), 3.92-3.86 (m, 2H), 2.48 (s, 3H), 1.18 (s, 3H).

LC-MS (method 3): $R_t$=2.67 min; MS (ESIpos): m/z=516 [M+H]$^+$.

The examples listed in Table 12 are prepared analogously to Example 104 from the appropriate starting materials:

TABLE 12

| Example No. | Structure (Yield) | LC-MS: $R_t$ [min] (method); MS (ESI): m/z [M + H]⁺ | ¹H-NMR (DMSO-d₆): δ = |
|---|---|---|---|
| 105 | (74% of theory) | 2.64 min (3); m/z = 556 | 8.20-7.95 (br. s, 2H), 8.11-8.03 (m, 4H), 7.48 (d, 2H), 7.10 (d, 2H), 4.92 (d, 1H), 4.54 (s, 2H), 4.03-3.94 (m, 1H), 3.91-3.85 (m, 2H), 3.89 (s, 3H), 1.18 (d, 3H). |
| 106 | (55% of theory) | 2.76 min (3); m/z = 518 | 8.37 (s, 1H), 8.27-7.91 (br. s, 2H), 7.97 (d, 2H), 7.61 (d, 2H), 7.47 (d, 2H), 7.09 (d, 2H), 4.92 (d, 1H), 4.42 (s, 2H), 4.02-3.93 (m, 1H), 3.92-3.85 (m, 2H), 1.18 (d, 3H). |

Example 107

4-({[6-Amino-3,5-dicyano-4-(4-{[(2R)-2,3-dihydroxypropyl]oxy}phenyl)pyridin-2-yl]sulfanyl}-methyl)-2-phenyl-1,3-oxazole-5-carboxylic acid

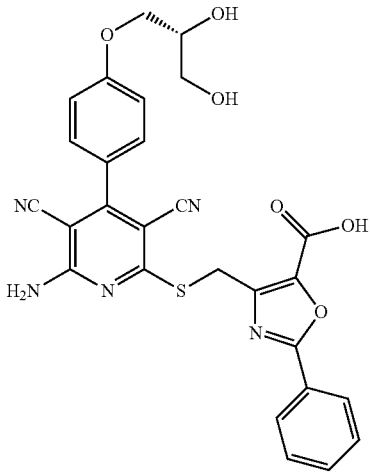 [SMILES: N#Cc1c(N)nc(SCc2nc(-c3ccccc3)oc2C(=O)O)c(C#N)c1-c1ccc(OC[C@H](O)CO)cc1]

30 mg (0.05 mmol) of the compound from Example 103 and 0.22 ml (0.22 mmol) 1 N aqueous sodium hydroxide solution are dissolved in 2 ml of 1,2-dimethoxyethane, 2 ml of water and 0.5 ml of methanol and stirred at RT for 3 h. The solvents are then removed on a rotary evaporator and the residue is taken up in 2 ml of water. The pH is adjusted to 4 by addition of 1 N hydrochloric acid. A white precipitate is formed, which is filtered off with suction and dried under reduced pressure.

Yield: 8 mg (26% of theory)

$^1$H-NMR (400 MHz, DMSO-$d_6$): δ=14.15-13.93 (br. s, 1H), 8.08-7.92 (br. s, 2H), 8.04 (d, 2H), 7.67-7.57 (m, 3H), 7.50 (d, 2H), 7.11 (d, 2H), 5.05-4.97 (br. s, 1H), 4.71 (s, 2H), 4.74-4.66 (br. s, 1H), 4.09 (dd, 1H), 3.99-3.89 (m, 1H), 3.87-3.79 (br. s, 1H), 3.51-3.43 (m, 2H).

LC-MS (method 3): $R_t$=2.19 min; MS (ESIpos): m/z=544 [M+H]$^+$.

Example 108

Methyl N-[6-({[2-(4-chlorophenyl)-1,3-oxazol-4-yl]methyl}thio)-3,5-dicyano-4-(4-{[(2S)-2,3-dihydroxypropyl]oxy}-phenyl)pyridin-2-yl]-N-methylglycinate

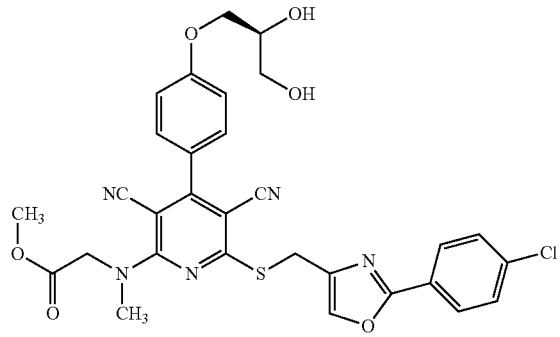 [SMILES: COC(=O)CN(C)c1nc(SCc2coc(-c3ccc(Cl)cc3)n2)c(C#N)c(-c2ccc(OC[C@@H](O)CO)cc2)c1C#N]

108 mg (0.20 mmol) of the compound from Example 103A are dissolved in 3 ml of dry DMF, and 54 mg (0.39 mmol) of methyl N-methylglycinate hydrochloride and 59 mg (0.59 mmol) of triethylamine are added. The reaction mixture is stirred at RT for 8 h. The solvent is then removed on a rotary evaporator and the residue is purified directly by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 13 mg (11% of theory)

$^1$H-NMR (400 MHz, DMSO-$d_6$): δ=8.19 (s, 1H), 7.98 (d, 2H), 7.62 (d, 2H), 7.55 (d, 2H), 7.11 (d, 2H), 5.01 (d, 1H), 4.71 (t, 1H), 4.61 (s, 2H), 4.41 (s, 2H), 4.09 (dd, 1H), 3.97 (dd, 1H), 3.87-3.78 (m, 1H), 3.65 (s, 3H), 3.51-3.43 (m, 5H).

LC-MS (method 5): $R_t$=3.65 min; MS (ESIpos): m/z=620 [M+H]$^+$.

Example 109

2-Amino-6-{[2-(4-chlorophenyl)-1,3-oxazol-4-yl]methoxy}-4-(4-{[(2R)-2,3-dihydroxypropyl]-oxy}-phenyl)pyridine-3,5-dicarbonitrile

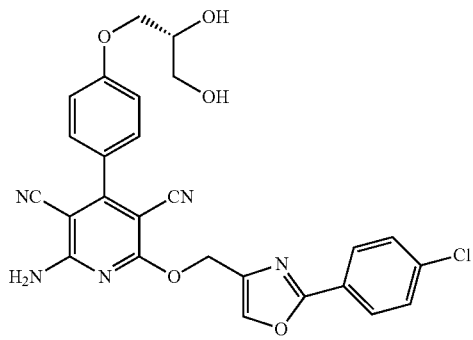 [SMILES: N#Cc1c(N)nc(OCc2coc(-c3ccc(Cl)cc3)n2)c(C#N)c1-c1ccc(OC[C@H](O)CO)cc1]

65 mg (0.12 mmol) of the compound from Example 101A are dissolved in 6 ml of acetic acid, and 3 ml of water are added. The mixture is stirred at RT for 30 min. The mixture is then heated to 70° C. and stirred at this temperature for a further 30 min A clear solution is formed. The mixture is then freed from the solvent on a rotary evaporator and the residue is purified by preparative HPLC (column: YMC GEL ODS-AQ S-5/15 μm; mobile phase gradient: acetonitrile/water 10:90→95:5). After removal of the solvent on a rotary evaporator, the product is obtained as a white solid.

Yield: 60 mg (100% of theory)

$^1$H-NMR (400 MHz, DMSO-$d_6$): δ=8.48 (s, 1H), 8.25-7.80 (br. s, 2H), 8.01 (d, 2H), 7.61 (d, 2H), 7.47 (d, 2H), 7.10 (d, 2H), 5.42 (s, 2H), 5.01 (d, 1H), 4.70 (t, 1H), 4.09 (dd, 1H), 3.95 (dd, 1H), 3.87-3.77 (m, 1H), 3.48 (t, 2H).

LC-MS (method 3): $R_t$=2.30 min; MS (ESIpos): m/z=518 [M+H]$^+$.

Example 110

2-Amino-6-{[2-(4-chlorophenyl)-1,3-oxazol-4-yl]methoxy}-4-[4-(2-hydroxyethoxy)phenyl]-pyridine-3,5-dicarbonitrile

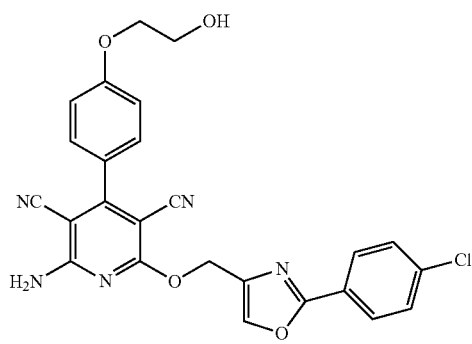 [SMILES: N#Cc1c(N)nc(OCc2coc(-c3ccc(Cl)cc3)n2)c(C#N)c1-c1ccc(OCCO)cc1]

72 mg (0.64 mmol) of potassium tert-butoxide are suspended in 1 ml of dry 1,2-dimethoxyethane. In succession, 270 mg (1.29 mmol) of the compound from Example 100A and 50 mg (0.13 mmol) of the compound from Example 99A are then added. The reaction mixture is stirred at 60° C. for 2 h and then cooled to RT and stirred at this temperature for a further 8 h. 5 ml of water and 1 ml of 2 N acetic acid are then added to the mixture. A precipitate is formed, which is filtered off with suction and purified by preparative HPLC (column: YMC GEL ODS-AQ S-5/15 μm; mobile phase gradient: acetonitrile/water 10:90→95:5). Removal of the solvent on a rotary evaporator gives the product as a yellow solid.

Yield: 44 mg (70% of theory)

$^1$H-NMR (400 MHz, DMSO-$d_6$): δ=8.48 (s, 1H), 8.18-7.85 (br. s, 2H), 8.00 (d, 2H), 7.62 (d, 2H), 7.48 (d, 2H), 7.11 (d, 2H), 5.41 (s, 2H), 4.91 (t, 1H), 4.08 (t, 2H), 3.73 (q, 2H).

LC-MS (method 14): $R_t$=1.22 min; MS (ESIpos): m/z=488 [M+H]$^+$.

The examples listed in Table 13 are prepared analogously to Example 110 from the appropriate starting materials:

TABLE 13

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 111 | (21% of theory) | 1.15 min (14); m/z = 498 | 8.11-7.85 (br. s, 2H), 7.89 (d, 2H), 7.48 (d, 2H), 7.11 (d, 2H), 7.09 (d, 2H), 5.39 (s, 2H), 4.91 (t, 1H), 4.08 (t, 2H), 3.82 (s, 3H), 3.74 (q, 2H), 2.50 (s, 3H). |

| Example No. | Structure (Yield) | LC-MS: $R_t$ [min] (method); MS (ESI): m/z [M + H]+ | 1H-NMR (DMSO-$d_6$): δ = |
|---|---|---|---|
| 112 | 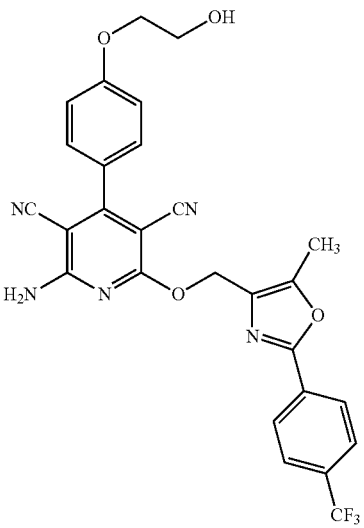<br>(20% of theory) | 2.41 min (15); m/z = 536 | 8.16 (d, 2H), 8.10-7.83 (br. s, 2H), 7.90 (d, 2H), 7.48 (d, 2H), 7.10 (d, 2H), 5.48 (s, 2H), 4.91 (t, 1H), 4.08 (t, 2H), 3.74 (q, 2H), 2.47 (s, 3H). |

Example 113

2-Amino-6-{[2-(4-fluorophenyl)-5-methyl-1,3-oxazol-4-yl]methoxy}-4-[4-(2-hydroxyethoxy)-phenyl]pyridine-3,5-dicarbonitrile

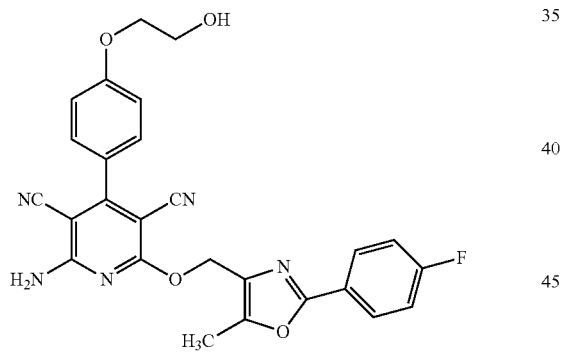

250 mg (0.81 mmol) of the compound from Example 102A, 228 mg (1.013 mmol) of 4-(chloromethyl)-2-(4-fluorophenyl)-5-methyl-1,3-oxazole and 224 mg (1.62 mmol) of potassium carbonate are initially charged in 8.6 ml of dry DMF and stirred at 70° C. for 2 h. The solvent is then removed on a rotary evaporator and the residue is purified by preparative HPLC (column: YMC GEL ODS-AQ S-5/15 μm; mobile phase gradient: acetonitrile/water 10:90→95:5). The product is then purified once more by HPLC (column: Waters Sunfire C 18 5 nm, 250 mm×20 mm; mobile phase gradient: water/ethanol 55:45→5:95; flow rate: 25 ml/min; temperature: 30° C.; detection: 210 nm).

Yield: 56 mg (14% of theory)

1H-NMR (400 MHz, DMSO-$d_6$): δ=8.07-7.87 (br. s, 2H), 8.03-7.98 (m, 2H), 7.48 (d, 2H), 7.37 (t, 2H), 7.10 (d, 2H), 5.40 (s, 2H), 4.91 (t, 1H), 4.08 (t, 2H), 3.74 (q, 2H), 2.49 (s, 3H).

LC-MS (method 14): $R_t$=1.18 min; MS (ESIpos): m/z=486 [M+H]+.

The examples listed in Table 14 are prepared analogously to Example 113 from the appropriate starting materials:
TABLE 14
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 114 | 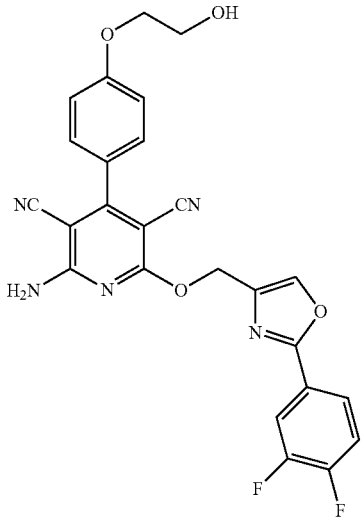 (29% of theory) | 2.33 min (9); m/z = 490 | 8.51 (s, 1H), 8.25-7.80 (br. s, 2H), 8.01 (dt, 1H), 7.90-7.82 (m, 1H), 7.62 (q, 1H), 7.48 (d, 2H), 7.11 (d, 2H), 5.41 (s, 2H), 4.93 (t, 1H), 4.08 (t, 2H), 3.23 (q, 2H). |
| 115 | 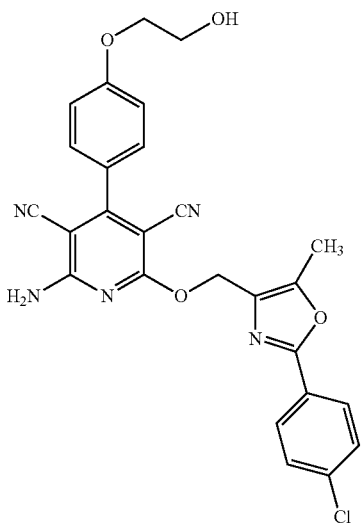 (16% of theory) | 1.26 min (14); m/z = 502 | 8.08-7.95 (br. s, 2H), 7.96 (d, 2H), 7.60 (d, 2H), 7.48 (d, 2H), 7.11 (d, 2H), 5.41 (s, 2H), 4.90 (t, 1H), 4.07 (t, 2H), 3.73 (q, 2H), 2.50 (s, 3H). |

Example 116

2-({[2-(4-Chlorophenyl)-1,3-oxazol-4-yl]methyl}sulfanyl)-4-[4-(2-hydroxyethoxy)phenyl]-6-(pyrrolidin-1-yl)pyridine-3,5-dicarbonitrile

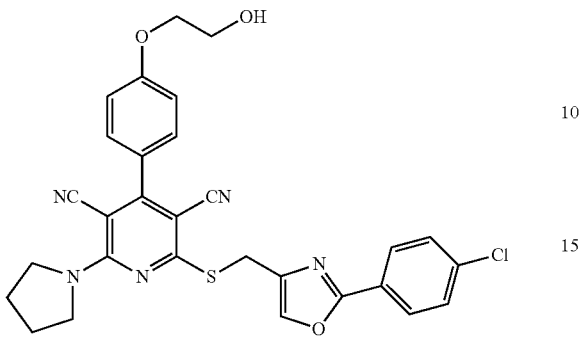

80 mg (0.15 mmol) of the compound from Example 123A are initially charged in 2 ml of dry THF, and 22 mg (0.31 mmol) of pyrrolidine are added. The reaction mixture is stirred at RT for 10 h. About 2 ml of water are then added, and the mixture is purified directly by preparative HPLC (column: YMC GEL ODS-AQ S-5/15 μm; mobile phase gradient: acetonitrile/water 10:90→95:5). After removal of the solvent on a rotary evaporator, the product was obtained as a white solid.

Yield: 26 mg (30% of theory)

$^1$H-NMR (400 MHz, DMSO-$d_6$): δ=8.20 (s, 1H), 7.97 (d, 2H), 7.61 (d, 2H), 7.49 (d, 2H), 7.11 (d, 2H), 4.91 (t, 1H), 4.51 (s, 2H), 4.09 (t, 2H), 3.91-3.81 (br. s, 4H), 3.74 (q, 2H), 2.02-1.91 (br. s, 4H).

LC-MS (method 3): $R_t$=3.02 min; MS (ESIpos): m/z=558 [M+H]$^+$.

The examples listed in Table 15 are prepared analogously to Example 116 from the appropriate starting materials:

TABLE 15

| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 117 | (37% of theory) | 2.53 min (3); m/z = 548 | 8.20 (s, 1H), 8.04-7.92 (m, 1H), 7.97 (d, 2H), 7.62 (d, 2H), 7.49 (d, 2H), 7.12 (d, 2H), 4.91 (t, 1H), 4.83 (t, 1H), 4.51 (s, 2H), 4.08 (t, 2H), 3.73 (q, 2H), 3.67-3.61 (m, 2H), 3.61-3.53 (m, 2H). |

TABLE 15-continued
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 118 | 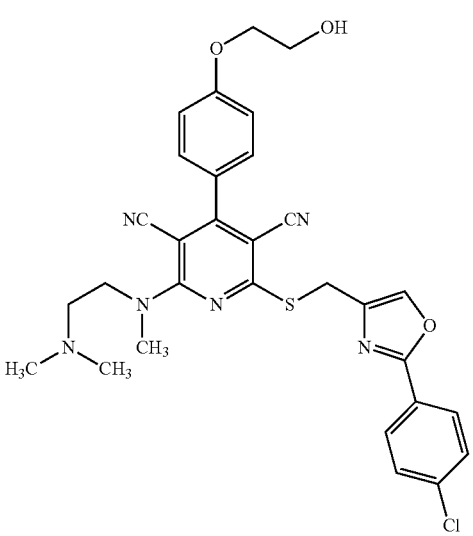 (30% of theory) | 1.75 min (3); m/z = 589 | 8.19 (s, 1H), 7.97 (d, 2H), 7.61 (d, 2H), 7.50 (d, 2H), 7.10 (d, 2H), 4.91 (t, 1H), 4.51 (s, 2H), 4.08 (t, 2H), 3.89 (t, 2H), 3.75 (q, 2H), 3.40 (s, 3H), 3.35-3.29 (m, 2H), 2.14 (s, 6H). |
| 119 | 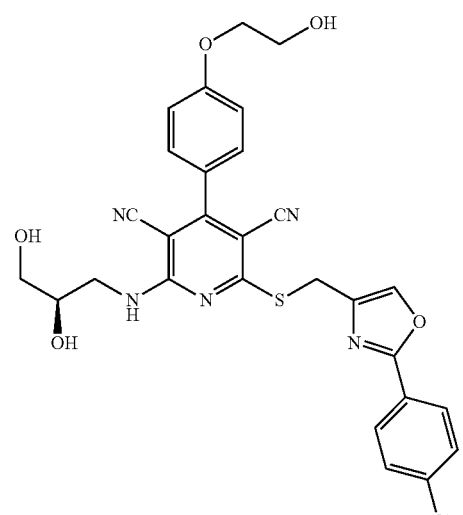 (34% of theory) | 2.36 min (3); m/z = 578 | 8.21 (s, 1H), 7.98 (d, 2H), 7.90 (t, 1H), 7.60 (d, 2H), 7.48 (d, 2H), 7.11 (d, 2H), 4.95 (d, 1H), 4.91 (t, 1H), 4.73 (t, 1H), 4.57 (d, 1H), 4.50 (d, 1H), 4.08 (t, 2H), 3.72-3.69 (m, 4H), 3.59-3.48 (m, 1H), 3.45-3.34 (m, 2H). |

The examples listed in Table 16 are prepared analogously to Example 48 from the appropriate starting materials:
TABLE 16
| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 120 | 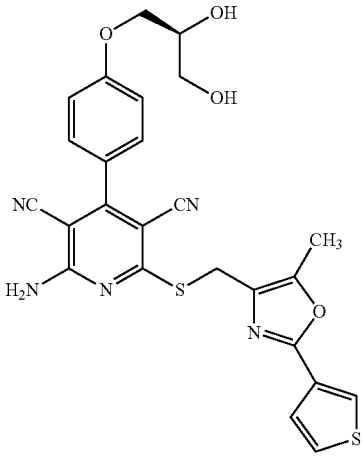 (79% of theory) | 2.25 min (3); m/z = 520 | 8.19-7.93 (br. s, 2H), 8.12 (d, 1H), 7.71 (dd, 1H), 7.53 (d, 1H), 7.48 (d, 2H), 7.10 (d, 2H), 5.00 (d, 1H), 4.70 (t, 1H), 4.49 (s, 2H), 4.09 (dd, 1H), 3.95 (dd, 1H), 3.87-3.78 (m, 1H), 3.47 (t, 2H), 2.45 (s, 3H). |
| 121 | 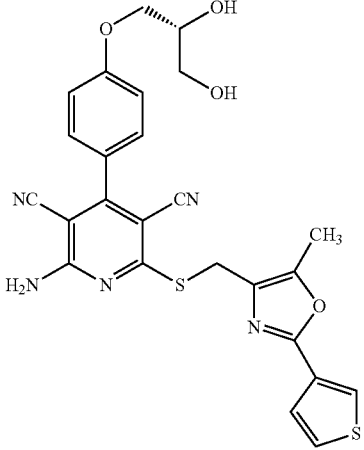 (74% of theory) | 2.25 min (3); m/z = 520 | 8.18-7.93 (br. s, 2H), 8.11 (d, 1H), 7.71 (dd, 1H), 7.52 (d, 1H), 7.48 (d, 2H), 7.11 (d, 2H), 5.01 (d, 1H), 4.70 (t, 1H), 4.49 (s, 2H), 4.09 (dd, 1H), 3.94 (dd, 1H), 3.85-3.78 (m, 1H), 3.46 (t, 2H), 2.44 (s, 3H). |

Example 122

2-({[2-(4-Chlorophenyl)-1,3-oxazol-4-yl]methyl}sulfanyl)-4-[3-fluoro-4-(2-hydroxyethoxy)phenyl]-6-[(2-hydroxyethyl)amino]pyridine-3,5-dicarbonitrile

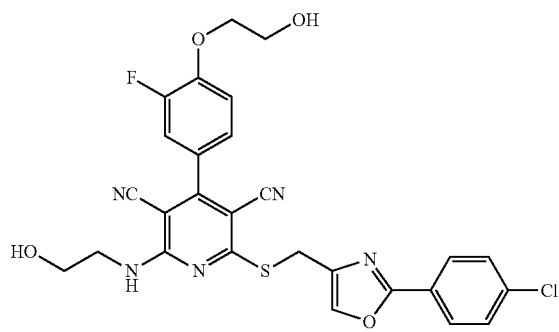 [SMILES: N#Cc1c(NCCO)nc(SCc2coc(-c3ccc(Cl)cc3)n2)c(C#N)c1-c1ccc(OCCO)c(F)c1]

25 mg (0.046 mmol) of 2-chloro-6-({[2-(4-chlorophenyl)-1,3-oxazol-4-yl]methyl}sulfanyl)-4-[3-fluoro-4-(2-hydroxyethoxy)phenyl]pyridine-3,5-dicarbonitrile (Example 125A) are initially charged in 1 ml of THF, 6 μl of 2-aminoethanol are added and the mixture is stirred at room temperature for 30 minutes. The reaction mixture is then purified directly by preparative HPLC (mobile phase gradient: acetonitrile/water 10:90→95:5). This gives 24 mg (94% of theory) of the target compound.

$^1$H-NMR (400 MHz, DMSO-$d_6$): δ=8.20 (s, 1H), 8.08 (t, 1H), 7.98 (d, 2H), 7.61 (d, 2H), 7.51 (dd, 1H), 7.39-7.31 (m, 2H), 4.51 (s, 2H), 4.16 (t, 2H), 3.76 (t, 2H), 3.67-3.62 (m, 2H), 3.58-3.55 (m, 2H).

LC-MS (method 3): $R_t$=2.52 min; MS (ESIpos): m/z=566 [M+H]$^+$.

Example 123

4-[({6-Amino-3,5-dicyano-4-[4-(2-hydroxyethoxy)phenyl]pyridin-2-yl}sulfanyl)methyl]-2-phenyl-1,3-oxazole-5-carboxylic acid

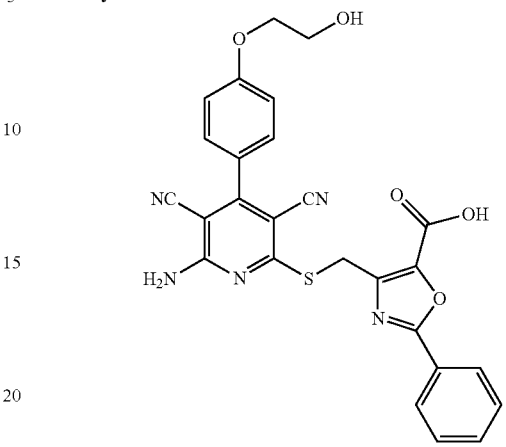

100 mg (0.190 mmol) of methyl 4-[({6-amino-3,5-dicyano-4-[4-(2-hydroxyethoxy)phenyl]pyridin-2-yl}sulfanyl)methyl]-2-phenyl-1,3-oxazole-5-carboxylate (Example 36) are initially charged in 6 ml THF, 379 μl (0.379 mmol) of 1 N aqueous lithium hydroxide solution are added and the mixture is stirred at room temperature for 30 minutes. The reaction mixture is then concentrated, water is added to the residue and the mixture is acidified with 1 N hydrochloric acid. The precipitated solid is filtered off and purified by preparative HPLC (mobile phase gradient: acetonitrile/water 10:90→95:5). This gives 23 mg (23% of theory) of the target compound.

$^1$H-NMR (400 MHz, DMSO-$d_6$): δ=8.03 (dd, 2H), 7.98-7.95 (m, 2H), 7.63-7.56 (m, 3H), 7.50 (d, 2H), 7.11 (d, 2H), 4.80 (s, 2H), 4.08 (t, 2H), 3.74 (t, 2H).

LC-MS (method 3): $R_t$=2.38 min; MS (ESIpos): m/z=514 [M+H]$^+$.

The examples listed in Table 17 are prepared analogously to Example 116 from the appropriate starting materials:

TABLE 17

| Example No. | Structure (Yield) | LC-MS: $R_t$ [min] (method); MS (ESI) m/z [M + H]$^+$ | $^1$H-NMR (DMSO-$d_6$): δ = |
|---|---|---|---|
| 124 | (67% of theory) | 2.81 min (3); m/z = 532 | 8.21 (t, 1H), 8.18 (s, 1H), 7.97 (d, 2H), 7.61 (d, 2H), 7.48 (d, 2H), 7.11 (d, 2H), 4.50 (s, 2H), 4.09 (t, 2H), 3.73 (t, 2H), 3.53 (q, 2H), 1.11 (t, 3H). |

TABLE 17-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 125 | 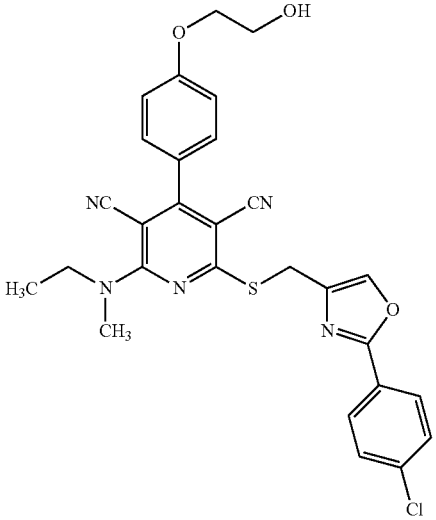<br>(72% of theory) | 2.87 min (3); m/z = 546 | 8.19 (s, 1H), 7.98 (d, 2H), 7.62 (d, 2H), 7.51 (d, 2H), 7.10 (d, 2H), 4.90 (br. s, 1H), 4.50 (s, 2H), 4.08 (t, 2H), 3.80 (q, 2H), 3.73 (t, 2H), 3.32 (s, 3H), 1.20 (t, 3H). |
| 126 | 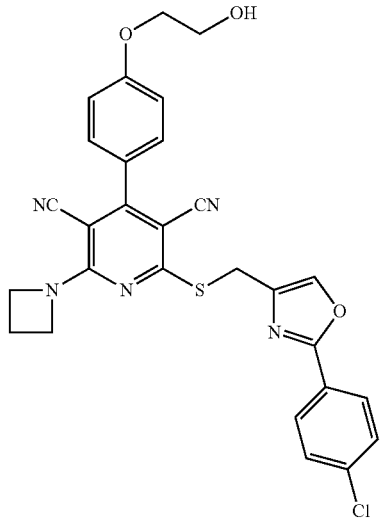<br>(40% of theory) | 2.39 min (7); m/z = 544 | 8.18 (s, 1H), 7.98 (d, 2H), 7.62 (d, 2H), 7.44 (d, 2H), 7.10 (d, 2H), 4.89 (br. s, 1H), 4.58-4.34 (m, 6H), 4.09 (t, 2H), 3.73 (t, 2H), 2.39 (quin, 2H). |

TABLE 17-continued
| Example No. | Structure (Yield) | LC-MS: $R_t$ [min] (method); MS (ESI): m/z [M + H]$^+$ | $^1$H-NMR (DMSO-$d_6$): δ = |
|---|---|---|---|
| 127 | 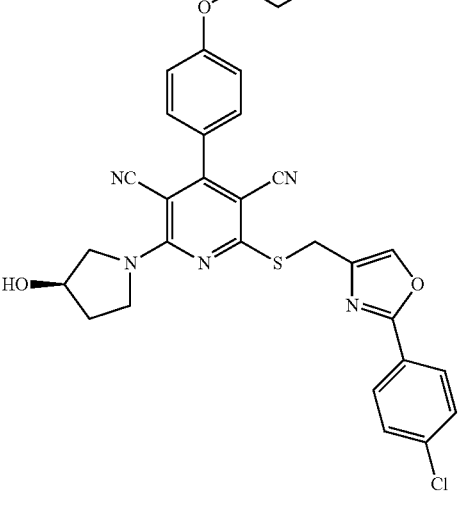 (84% of theory) | 2.07 min (7); m/z = 574 | 8.19 (s, 1H), 7.97 (d, 2H), 7.61 (d, 2H), 7.48 (d, 2H), 7.10 (d, 2H), 5.14 (d, 1H), 4.90 (t, 1H), 4.52 (s, 2H), 4.41 (br. s, 1H), 4.08 (t, 2H), 4.01-3.82 (m, 3H), 3.80-3.71 (m, 3H), 2.09-1.88 (m, 2H). |
| 128 | 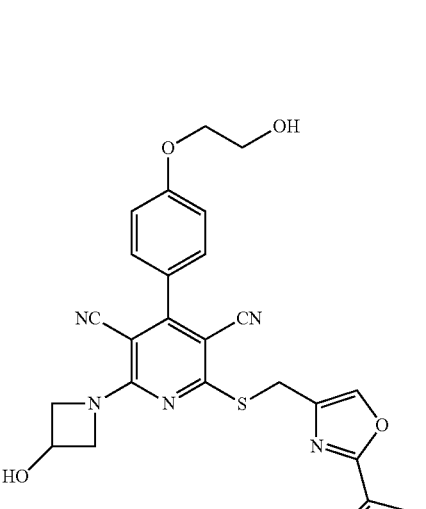 (52% of theory) | 2.06 min (7); m/z = 560 | 8.18 (s, 1H), 7.98 (d, 2H), 7.62 (d, 2H), 7.45 (d, 2H), 7.10 (d, 2H), 5.88 (d, 1H), 4.90 (t, 1H), 4.73-4.55 (m, 3H), 4.48 (s, 2H), 4.18 (d, 2H), 4.08 (t, 2H), 3.73 (q, 2H). |

TABLE 17-continued

| Example No. | Structure (Yield) | LC-MS: $R_t$ [min] (method); MS (ESI): m/z [M + H]$^+$ | $^1$H-NMR (DMSO-d$_6$): δ = |
|---|---|---|---|
| 129 | (65% of theory)* | 2.37 min (3); m/z = 532 | 8.38 (s, 1H), 8.09-7.97 (m, 3H), 7.62 (d, 2H), 7.46 (d, 2H), 7.10 (d, 2H), 5.50 (s, 2H), 4.91 (t, 1H), 4.86-4.80 (m, 1H), 4.08 (t, 2H), 3.73 (q, 2H), 3.64-3.57 (m, 4H). |
| 130 | (60% of theory)* | 2.43 min (3); m/z = 544 | 8.36 (s, 1H), 8.00 (d, 2H), 7.62 (d, 2H), 7.45 (d, 2H), 7.10 (d, 2H), 5.89 (d, 1H), 5.46 (s, 2H), 4.90 (t, 1H), 4.75-4.56 (m, 3H), 4.25-4.07 (m, 4H), 3.73 (q, 2H). |

*The reaction is carried out in DMF as solvent (instead of THF)

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (foetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$M to $3 \times 10^{-6}$M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357 (1998), 1-9).

Table 18 below lists the $EC_{50}$ values of representative working examples for the receptor stimulation on adenosine A1, A2a and A2b receptor subtypes:

TABLE 18

| Example No. | $EC_{50}$ A1 [nM] (1 µM forskolin) | $EC_{50}$ A2a [nM] | $EC_{50}$ A2b [nM] |
|---|---|---|---|
| 10 | 0.5 | 1130 | 922 |
| 11 | 0.3 | 703 | 845 |
| 31 | 0.9 | 467 | 315 |
| 48 | 0.3 | 138 | 4.4 |
| 49 | 0.4 | 300 | 100 |
| 50 | 0.4 | 3000 | 118 |
| 57 | 0.2 | 525 | 44 |
| 60 | 0.3 | 3000 | 236 |
| 61 | 0.7 | 439 | 221 |
| 66 | 0.9 | 575 | 370 |
| 80 | 0.8 | 461 | 89 |
| 81 | 0.3 | 64 | 20 |
| 93 | 8.9 | 522 | 336 |
| 95 | 0.5 | 3000 | 3000 |
| 101 | 0.4 | 72 | 226 |
| 106 | 0.3 | 318 | 48 |
| 110 | 0.3 | 497 | 95 |
| 114 | 0.2 | 1970 | 969 |
| 116 | 0.4 | 3000 | 698 |
| 117 | 0.2 | 1440 | 1090 |
| 119 | 0.3 | 1950 | 3000 |
| 122 | 4.1 | 3000 | 2250 |
| 126 | 0.5 | 684 | 78 |
| 127 | 0.4 | 984 | 283 |
| 128 | 0.1 | 1050 | 237 |
| 129 | 0.4 | 3000 | 3000 |
| 130 | 0.6 | 3000 | 245 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters. Blood pressure, heart rate and their changes are then recorded over a period of 24 hours.

B-4. Measurement of Blood Pressure and Heart Rate on Awake Marmosets

Various concentrations of the test substances are administered orally to awake marmosets which carry an internal transmitter capable of measuring both blood pressure and heart rate (telemetric monitoring of hemodynamic parameters). Blood pressure, heart rate and their changes are then recorded for a period of 6-24 hours.

B-5. Determination of Pharmacokinetic Parameters after Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC (area under the concentration-time curve), $C_{max}$ (maximum plasma concentration), $T_{1/2}$ (half-life) and CL (clearance) by means of a validated pharmacokinetic computer program.

B-6. Determination of the Solubility

Reagents Required:
PBS buffer pH 6.5: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1 N hydrochloric acid (for example from Merck, Art. No. 1.09057.1000) the pH is then adjusted to 6.5.

PEG/water solution (70:30 v/v): 70 ml of polyethylene glycol 400 (for example from Merck, Art. No. 8.17003.1000) and 30 ml of distilled water are homogenized in a 100 ml measuring flask.

PEG/PBS buffer pH 6.5 (20:80 v/v): 20 ml of polyethylene glycol 400 (for example from Merck, Art. No. 8.17003.1000) and 80 ml of PBS buffer pH 6.5 are homogenized in a 100 ml measuring flask.

Dimethyl sulfoxide (for example from Baker, Art. No. 7157.2500)

Distilled water.

Preparation of the Starting Solution (Original Solution):

At least 4 mg of the test substance are weighed accurately into a wide-necked 10 mm screw V vial (from Glastechnik Gräfenroda GmbH, Art. No. 8004-WM-H/V15µ) with fitting screw cap and septum, in a pipetting robot DMSO is added to a concentration of 50 mg/ml and the mixture is shaken for 10 minutes.

Preparation of the Calibration Solutions:

Preparation of the Starting Solution for Calibration Solutions (Stock Solution):

With the aid of a pipetting robot, 10 μl of the original solution are transferred into a microtiter plate and made up with DMSO to a concentration of 600 μg/ml. The sample is shaken until everything has gone into solution.

Calibration Solution 1 (20 μg/Ml):

1000 μl of DMSO are added to 34.4 μl of the stock solution, and the mixture is homogenized.

Calibration Solution 2 (2.5 μg/Ml):

700 μl of DMSO are added to 100 μl of calibration solution 1, and the mixture is homogenized.

Preparation of the Sample Solutions:

Sample Solution for Solubilities of Up to 5 g/Liter in PBS Buffer pH 6.5:

10 μl of the original solution are transferred into a microtiter plate, and 1000 μl of PBS buffer pH 6.5 are added.

Sample Solution for Solubilities of Up to 5 g/Liter in PEG/Water (70:30):

10 μl of the original solution are transferred into a microtiter plate, and 1000 μl of PEG/water (70:30) are added.

Sample Solution for Solubilities of Up to 5 g/Liter in PEG/PBS Buffer pH 6.5 (20:80):

10 μl of the original solution are transferred into a microtiter plate, and 1000 μl of PEG/PBS buffer pH 6.5 (20:80) are added.

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 μl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 μl of the supernatant are removed and diluted 1:5 and 1:100 with DMSO. From each dilution, a sample is transferred into a vessel suitable for HPLC analysis.

Analysis:

The samples are analysed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 ng/ml; 3) sample solution 1:5; 4) sample solution 1:100.

HPLC Method for Acids:

Agilent 1100 mit DAD (G1315A), quat. pump (G1311A), autosampler CTC HTS PAL, degasser (G1322A) and column thermostat (G1316A); column: Phenomenex Gemini C18, 50 mm×2 mm, 5μ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 mM 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5μ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

B-7. Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 μM. To this end, stock solutions of the substances at a concentration of 1-2 mM in acetonitrile are prepared and then pipetted at a dilution of 1:100 into the incubation mixture. The liver microsomes are incubated at 37° C. in 50 mM potassium phosphate buffer (pH 7.4) with and without NADPH-generating system consisting of 1 mM NADP$^+$, 10 mM glucose 6-phosphate and 1 unit of glucose 6-phosphate dehydrogenase. Primary hepatocytes are also incubated at 37° C. in suspension in Williams E medium. After an incubation time of 0-4 hours, the incubation mixtures are quenched with acetonitrile (final concentration about 30%) and the protein is centrifuged off at about 15 000×g. The samples quenched in this manner are either analyzed directly or stored at −20° C. until analysis.

Analysis is carried out using high-performance liquid chromatography with ultraviolet and mass-spectrometric detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

C. WORKING EXAMPLES OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:

The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400.20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

<img>Structure (I): a pyridine ring bearing NC groups at the 3,5-positions, with substituents including an $R^4R^5N$- group, an A-CH$_2$-(oxazole with $R^6$, $R^7$) group, and a 4-substituted phenyl group bearing $R^3$, with an OCH$_2$C($R^1$)($R^2$)OH substituent on the phenyl.</img> in which

A represents O or S, $R^1$ represents hydrogen or $(C_1$-$C_4)$-alkyl, $R^2$ represents hydrogen or $(C_1$-$C_4)$-alkyl which may be substituted by hydroxyl, $(C_1$-$C_4)$-alkoxy or up to three times by fluorine or $R^1$ and $R^2$ are attached to one another and together with the carbon atom to which they are attached form a cyclopropane or cyclobutane ring, $R^3$ represents hydrogen, halogen or $(C_1$-$C_4)$-alkyl, $R^4$ and $R^5$ together with the nitrogen atom to which they are attached form a pyrrolidino ring which may be mono- or disubstituted by identical or different substituents from the group consisting of $(C_1$-$C_4)$-alkyl, hydroxyl, oxo and $(C_1$-$C_4)$-alkoxy, and either (i)

$R^6$ represents $(C_6$-$C_{10})$-aryl which may be mono- to trisubstituted by identical or different substituents from the group consisting of halogen, nitro, cyano, $(C_1$-$C_4)$-alkyl, trifluoromethyl, hydroxyl, $(C_1$-$C_4)$-alkoxy, difluoromethoxy, trifluoromethoxy, mono-$(C_1$-$C_4)$-alkylaminocarbonyl, $(C_1$-$C_4)$-alkoxycarbonyl and carboxyl, and $R^7$ represents hydrogen, fluorine, chlorine, $(C_1$-$C_4)$-alkyl, trifluoromethyl, $(C_1$-$C_4)$-alkoxycarbonyl, carboxyl or phenyl, where $(C_1$-$C_4)$-alkyl may be substituted by hydroxyl or $(C_1$-$C_4)$-alkoxy and phenyl may be substituted by halogen, cyano, $(C_1$-$C_4)$-alkyl or trifluoromethyl, or (ii)

$R^6$ represents hydrogen or $(C_1$-$C_4)$-alkyl and $R^7$ represents phenyl which may be mono- or disubstituted by identical or different substituents from the group consisting of halogen, cyano, $(C_1$-$C_4)$-alkyl and trifluoromethyl, or a salt thereof.

2. The compound of claim 1 in which

A represents O or S, $R^1$ represents hydrogen or methyl, $R^2$ represents hydrogen, methyl, hydroxymethyl, methoxymethyl or trifluoromethyl, $R^3$ represents hydrogen, fluorine or methyl, $R^4$ and $R^5$ together with the nitrogen atom to which they are attached form a pyrrolidino ring which may be mono- or disubstituted by identical or different substituents from the group consisting of methyl, hydroxyl and/or methoxy, and either (i)

$R^6$ represents phenyl, which may be mono- to trisubstituted by identical or different substituents from the group consisting of fluorine, chlorine, cyano, $(C_1$-$C_4)$-alkyl, trifluoromethyl, $(C_1$-$C_4)$-alkoxy, trifluoromethoxy, mono-$(C_1$-$C_4)$-alkylaminocarbonyl, $(C_1$-$C_4)$-alkoxycarbonyl and carboxyl, and $R^7$ represents hydrogen, $(C_1$-$C_4)$-alkyl, trifluoromethyl, $(C_1$-$C_4)$-alkoxycarbonyl, carboxyl or phenyl which may be substituted by fluorine or chlorine, or (ii)

$R^6$ represents hydrogen and $R^7$ represents phenyl which may be mono- or disubstituted by identical or different substituents from the group consisting of fluorine, chlorine, cyano, methyl and trifluoromethyl, or a salt thereof.

3. The compound of claim 1 in which

A represents O or S, $R^1$ represents hydrogen or methyl, $R^2$ represents hydrogen, methyl, hydroxymethyl or trifluoromethyl, $R^3$ represents hydrogen or fluorine, $R^4$ and $R^5$ together with the nitrogen atom to which they are attached form a pyrrolidino ring, which may be substituted by hydroxyl, $R^6$ represents phenyl which may be mono- or disubstituted by identical or different substituents from the group consisting of fluorine, chlorine, methyl, trifluoromethyl, methoxy and carboxyl, and $R^7$ represents hydrogen, methyl, trifluoromethyl, methoxycarbonyl or carboxyl, or a salt thereof.

4. A process for preparing compounds of formula (I) as defined in claim 1 comprising:

reacting a compound of formula (II)

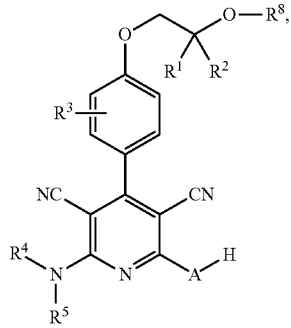

in which A, $R^1$, $R^2$, $R^3$, $R^4$ and $R^5$ have the meaning given in claim 1, and $R^8$ represents hydrogen or a temporary hydroxyl protective group in an inert solvent in the presence of a base with a compound of formula (III)

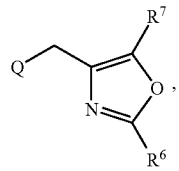

in which $R^6$ and $R^7$ have the meanings given in claim 1 and Q represents halogen, mesylate, tosylate or triflate, or alternatively, if A represents O, reacting a compound of formula (IV)

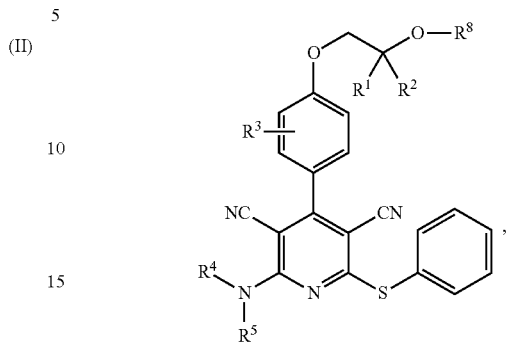

in which $R^1$, $R^2$, $R^3$, $R^4$, $R^5$ and $R^8$ each have the meanings given above in an inert solvent in the presence of a base with a compound of formula (V)

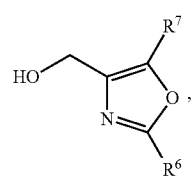

in which $R^6$ and $R^7$ have the meaning given in claim 1, removing any protective groups present, and optionally reacting the resulting compound of formula (I) with a base or acid to produce a salt thereof.

5. A pharmaceutical composition comprising a compound of claim 1 and one or more inert nontoxic pharmaceutically suitable auxiliaries.

\* \* \* \* \*